(12) United States Patent
Sharpless et al.

(10) Patent No.: US 8,158,347 B2
(45) Date of Patent: Apr. 17, 2012

(54) **DETERMINATION OF MOLECULAR AGE BY DETECTION OF *INK4A/ARF* EXPRESSION**

(75) Inventors: Norman E. Sharpless, Chapel Hill, NC (US); Krishnamurthy Janakiraman, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 981 days.

(21) Appl. No.: 11/663,667

(22) PCT Filed: Sep. 27, 2005

(86) PCT No.: PCT/US2005/034542
§ 371 (c)(1),
(2), (4) Date: Oct. 26, 2007

(87) PCT Pub. No.: WO2006/036943
PCT Pub. Date: Apr. 6, 2006

(65) Prior Publication Data
US 2008/0108062 A1    May 8, 2008

Related U.S. Application Data

(60) Provisional application No. 60/613,296, filed on Sep. 27, 2004.

(51) Int. Cl.
*C12Q 1/68* (2006.01)
(52) U.S. Cl. ........................................................ 435/6.1
(58) Field of Classification Search .................... None
See application file for complete search history.

(56) References Cited

U.S. PATENT DOCUMENTS

| | | | |
|---|---|---|---|
| 6,066,457 A | 5/2000 | Hampson et al. | |
| 6,287,775 B1 * | 9/2001 | O'Brien et al. | 435/6 |
| 2003/0099950 A1 | 5/2003 | Hanna | |
| 2003/0226159 A1 | 12/2003 | Bachoo et al. | |
| 2004/0014087 A1 | 1/2004 | Hodgson et al. | |
| 2004/0033490 A1 | 2/2004 | Laird et al. | |
| 2004/0048253 A1 | 3/2004 | Panzer et al. | |
| 2004/0054162 A1 | 3/2004 | Hanna | |
| 2004/0115629 A1 | 6/2004 | Panzer et al. | |

FOREIGN PATENT DOCUMENTS

WO    WO2006/036943    4/2006

OTHER PUBLICATIONS

Melek et al. (Kidney International, vol. 63 (2003), pp. 2134-2143).*
Brenner et al. (Oncogene. Jul. 16, 1998;17(2):199-205).*
Joosten et al. (Blood. Jul. 15, 2003;98(2):322-27).*
Zaucha et al. (Blood. Jul 15, 2003;98(2):322-27).*
Chimenti et al. (Circ Res. Oct. 3, 2003;93(7):604-13. Epub Sep. 4, 2003).*
Zindy et al. Oncogene. Jul. 10, 1997;15(2):203-11.*
Bea et al., BMI-1 Gene Amplification And Overexpression In Hematological Malignancies Occur Mainly in Mantle Cell Lymphomas. *Cancer Research*. vol. 61 pp. 2409-2412 (2001).
Collins, C.J., and Sedivy, J.M., Involvement of the INK4a/Arf gene locus in senescence. *Aging Cell*. vol. 2 pp. 145-150 (2003).
Jacobs et al., The Oncogene And Polycombgroup Gene BMI-1 Regulates Cell Proliferation And Senescence Through The INK4A Locus. *Nature*. vol. 397, No. 6715 pp. 164-168.
Krishnamurthy et al., Ink4a/Arf expression is a biomarker of aging. *The Journal of Clinical Investigation*. vol. 114, No. 9 pp. 1299-1307 (2004).
Notification Concerning Transmittal of International Preliminary Report on Patentability (Chapter I of the Patent Cooperation Treaty) corresponding to International Application No. PCT/US2005/034542 dated Mar. 19, 2009.
Notification of Transmittal of the International Search Report and the Written Opinion of the International Searching Authority, or the Declaration corresponding to International Application No. PCT/US2005/34542 dated May 19, 2008.
Satyanarayana, A. and Rudolph, K.L., p16 and ARF: activation of teenage proteins in old age. *The Journal of Clinical Investigation*. vol. 114, No. 9 pp. 1237-1240 (2004).
Schmitt et al., A Senescence Program Controlled by p53 and p16$^{INK4a}$ Contributes to the Outcome of Cancer Therapy. *Cell*. vol. 109. pp. 335-346 (2002).
Sharpless, N.E., and DePinho, R.A., Telomeres, stem cells, senescence, and cancer. *The Journal of Clinical Investigation*. vol. 113, No. 2 pp. 160-168 (2004).
Sharpless, N.E., and DePinho, R.A., The INK4A/ARF locus and its two gene products. *Current Opinion in Genetics and Development*. vol. 9 pp. 22-30 (1999).
Harman (1956) *J Gerontol* 11:298-300.
Harman (1961) *J Gerontol* 16:247-254.
Martin et al. (1970) *Lab Invest* 23:86-92.
Bardeesy et al., "Animal Models of Melanoma: Recent Advances and Future Prospects," Advances in Cancer Research. pp. 123-156 (2000).
Hart et al., "Cell adhesion receptor expression during melanoma progression and metastasis," Cancer and Metastasis Reviews. vol. 10 pp. 115-128 (1991). Kanavaros et al., "Immunohistochemical expression of p53, p21/waf1, Rb, p16, cyclin D1, p27, Ki67, cyclin A, cyclin B1, bcl2, bax and bak proteins and apoptotic index in normal thymus," Histology and Histopathology. vol. 16 pp. 1005-1012 (2001).
Muss et al., "Expression of p16INK4a after chemotherapy in older women with early stage breast cancer," Designing Clinical Trials for Older Patients: Nuts and Bolts. Jun. 2011 ASCO, Chicago, Illinois. Presented Jun. 4, 2011 [Abstract].
Van Leeuwen et al., "Attachment, spreading and migration of melanoma cells on vitronectin: The rôle of $\alpha_v\beta_3$ and $\alpha_v\beta_5$ integrins," Experimental Dermatology. vol. 5 pp. 308-315 (1996).
Alevizopoulos et al., "Cyclin E and c-Myc promote cell proliferation in the presence of p16$^{INK4a}$ and of hypophosphorylated retinoblastoma family proteins," The EMBO Journal. vol. 16, No. 17 pp. 5322-5333 (1997).

(Continued)

Primary Examiner — Christopher M. Babic
(74) Attorney, Agent, or Firm — Jenkins, Wilson, Taylor & Hunt, P.A.

(57) ABSTRACT

The presently disclosed subject matter provides methods for determining the molecular age of a tissue. Also provided are methods for employing a molecular age that has been determined for a tissue for assessing the appropriateness of various therapeutic applications for the tissue or a subject comprising the tissue.

18 Claims, 14 Drawing Sheets

OTHER PUBLICATIONS

Ang et al., "Human Papillomavirus and Survival of Patients with Oropharyngeal Cancer," The New England Journal of Medicine. vol. 363 pp. 24-35 (2010).

Balsam et al., "Haematopoietic stem cells adopt mature haematopoietic fates in ischaemic myocardium," Nature. vol. 428 pp. 668-673 (2004).

Bergmann et al., "Evidence for Cardiomyocyte Renewal in Humans," Science. vol. 324 pp. 98-102 (2009).

Campisi, J., and d'Adda di Fagagna, F., "Cellular senescence: when bad things happen to good cells," Nature Reviews. vol. 8 pp. 729-740 (2007).

Koppelstaetter et al., "Markers of cellular senescence in zero hour biopsies predict outcome in renal transplantation," Aging Cell. vol. 7 pp. 491-497 (2008).

Krimpenfort et al., "Loss of $p16^{Ink4a}$ confers susceptibility to metastatic melanoma in mice," Nature. vol. 413 pp. 83-86 (2001).

Lemster et al., "Induction of CD56 and TCR-Independent Activation of T Cells with Aging," The Journal of Immunology. vol. 180 pp. 1979-1990 (2008).

McGlynn et al., "Cellular senescence in pretransplant renal biopsies predicts postoperative organ function," Aging Cell. vol. 8 pp. 45-51 (2009).

Nakao et al., "Induction of p16 during immortalization by HPV 16 and 18 and not during malignant transformation," British Journal of Cancer. vol. 75, No. 10 pp. 1410-1416 (1997).

Shapiro et al., "Reciprocal Rb Inactivation and $p16^{INK4}$ Expression in Primary Lung Cancers and Cell Lines," Cancer Research. vol. 55 pp. 505-509 (1995).

Song et al., "Lifestyle impacts on the aging-associated expression of biomarkers of DNA damage and telomere dysfunction in human blood," Aging Cell. vol. 9 pp. 607-615 (2010).

Yamakoshi et al., "Real-time in vivo imaging of p16Ink4 reveals cross talk with p53," J. Cell Biol. vol. 186, No. 3 pp. 393-407 (2009).

Alani et al., "Id1 regulation of cellular senescence through transcriptional repression of p16/Ink4a," PNAS. vol. 98, No. 14 pp. 7812-7816 (2001).

Alcorta et al., "Involvement of the cyclin-dependent kinase inhibitor p16 (INK4a) in replicative senescence of normal human fibroblasts," PNAS. vol. 93 pp. 13742-13747 (1996).

Artandi, S.E., and DePinho, R.A., "A critical role for telomeres in suppressing and facilitating carcinogenesis," Current Opinion in Genetics and Development. vol. 10 pp. 39-46 (2000).

Artandi et al., "Telomere dysfunction promotes non-reciprocal translocations and epithelial cancers in mice," Nature. vol. 406 pp. 641-645 (2000).

Bates et al., "$p14^{ARF}$ links the tumour suppressors RB and p53," Nature. vol. 395 pp. 124-125 (1998).

Blake et al., "The Mouse Genome Database (MGD): expanding genetic and genomic resources for the laboratory mouse," Nucleic Acids Research. vol. 28, No. 1 pp. 108-111 (2000).

Bodnar et al., "Extension of Life-Span by Introduction of Telomerase into Normal Human Cells," Science. vol. 279 pp. 349-352 (1998).

Bonner-Weir et al., "Responses of Neonatal Rat Islets to Streptozotocin," Diabetes. vol. 30 pp. 64-69 (1981).

Bradl et al., "Malignant melanoma in transgenic mice," PNAS. vol. 88 pp. 164-168 (1991).

Campisi, "Cancer and Ageing: Rival Demons?" Nature Reviews. vol. 3 pp. 339-349 (2003).

Campisi et al., "Senescent Cells, Tumor Suppression, and Organismal Aging: Good Citizens, Bad Neighbors," Cell. vol. 120 pp. 513-522 (2005).

Carnero et al., "$p16^{INK4A}$ and $p19^{ARF}$ act in overlapping pathways in cellular immortalization," Nature Cell Biology. vol. 2 pp. 148-155 (2000).

Cheng et al., "Hematopoietic Stem Cell Quiescence Maintained by $p21^{cip1/waf1}$," Science. vol. 287 pp. 1804-1808 (2000).

Chin et al., "Cooperative effects of $INK4a$ and $ras$ in melanoma susceptibility in vivo," Genes & Development. vol. 11 pp. 2822-2834 (1997).

Chin et al., "Essential role for oncogenic Ras in tumour maintenance," Nature. vol. 400 pp. 468-472 (1999).

Chin et al., "Malignant melanoma: modern black plague and genetic black box," Genes & Development. vol. 12 pp. 3467-3481 (1998).

Chkhotua et al., "Increased expression of $p16^{(INK4a)}$ $p27^{(Kip1)}$ cyclin-dependent kinase inhibitor genes in aging human kidney and chronic allograft nephropathy," American Journal of Kidney Disease. vol. 41, No. 6 pp. 1303-1313 (2003).

Coschigano et al., "Assessment of Growth Parameters and Life Span by GHR/BP Gene-Disrupted Mice," Endocrinology. vol. 141, No. 7 pp. 2608-2613 (2000).

Danen et al., "Emergence of α5β1 fibronectin- and αvβ3 vitronectin-receptor expression in melanocytic tumour progression," Histopathology. vol. 24 pp. 249-256 (1994).

de Stanchina et al., "E1A signaling to p53 involves the $p19^{ARF}$ tumor suppressor," Genes & Development. vol. 12 pp. 2434-2442 (1998).

Deng et al., "Mice Lacking $p21^{CIP1/WAF1}$ Undergo Normal Development, but Are Defective in G1 Checkpoint Control," Cell. vol. 82 pp. 675-684 (1995).

Dickson et al., "Human Keratinocytes That Express hTERT and Also Bypass a $p16^{INK4a}$-Enforced Mechanism That Limits Life Span Become Immortal yet Retain Normal Growth and Differentiation Characteristics," Molecular and Cellular Biology. vol. 20, No. 4 pp. 1436-1447 (2000).

Donehower et al., "Mice deficient for p53 are developmentally normal but susceptible to spontaneous tumours," Nature. vol. 356 pp. 215-221 (1992).

Dor et al., "Adult pancreatic β-cells are formed by self-duplication rather than stem-cell differentiation," Nature. vol. 429 pp. 41-46 (2004).

Draper et al., "Second primary neoplasms in patients with retinoblastoma," Br. J. Cancer. vol. 53 pp. 661-671 (1986).

Dyson, "The regulation of E2F by pRB-family proteins," Genes & Development. vol. 12 pp. 2245-2262 (1998).

Eischen et al., "Disruption of the ARF-Mdm2-p53 tumor suppressor pathway in Myc-induced lymphomagenesis," Genes & Development. vol. 13 pp. 2658-2669 (1999).

Engwerda et al., "Aged T Cells are Hyporesponsive to Costimulation Mediated by CD28," Journal of Immunology. vol. 152 pp. 3740-3747 (1994).

Fåhraeus, R., and Lane, D.P., "The $p^{16INK4a}$ tumour suppressor protein inhibits $\alpha_v\beta_3$ integrin-mediated cell spreading on vitronectin by blocking PKC-dependnet localization of $\alpha_v\beta_3$ to focal contacts," The EMBO Journal. vol. 18, No. 8 pp. 2106-2118 (1999).

Fargnoli et al., "$CDKN2a/p16^{INK4a}$ Mutations and Lack of $p19^{ARF}$ Involvement in Familial Melanoma Kindreds," The Journal of Investigative Dermatology. vol. 111, No. 6 pp. 1202-1206 (1998).

Fernandes et al., "Differentiation of New Insulin-Producing Cells Is Induced by Injury in Adult Pancreatic Islets," Endocrinology. vol. 138, No. 4 pp. 1750-1762 (1997).

FitzGerald et al., "Prevalence of germ-lin mutations in p16, p19ARF, and CDK4 in familial melanoma: Analysis of a clinic-based population," PNAS. vol. 93 pp. 8541-8545 (1996).

Førenes et al., "TP53 allele loss, mutations and expression in malignant melanoma," Br. J. Cancer. vol. 69 pp. 253-259 (1994).

Frank et al., "DNA Ligase IV Deficiency in Mice Leads to Defective Neurogenesis and Embryonic Lethality via the p53 pathway," Molecular Cell. vol. 5 pp. 993-1002 (2000).

Franklin et al., "CDK inhibitors p18INK4c and p27Kip1 mediate two separate pathways to collaboratively suppress pituitary tumorigenesis," Genes & Development. vol. 12 pp. 2899-2911 (1998).

Gao et al., "Interplay of p53 and DNA-repair protein XRCC4 in tumorigenesis, genomic stability and development," Nature. vol. 404 pp. 897-900 (2000).

Gause et al., "Chromosomal and Genetic Alterations of 7,12-Dimethylbenz[a]anthracene-Induced Melanoma From TP-ras Transgenic Mice," Molecular Carcinogenesis, vol. 20 pp. 78-87 (1997).

Gil et al., "Polycomb CBX7 has a unifying role in cellular lifespan," Nature Cell Biology. vol. 6, No. 1 pp. 67-72 (2004).

Gilchrest et al., "The Pathogenesis of Melanoma Induced by Ultraviolet Radiation," The New England Journal of Medicine. vol. 340, No. 17 pp. 1341-1348 (1999).

Glendening et al., "Homozygous Loss of the $p15^{INK4B}$ Gene (and not the $p16^{INK4}$ Gene) during Tumor Progression in a Sporadic Melanoma Patient," Cancer Research. vol. 55 pp. 5531-5535 (1995).

Goldstein et al., "Increased Risk of Pancreatic Cancer in Melanoma-Prone Kindreds with $p16^{INK4}$ Mutations," The New England Journal of Medicine. vol. 333, No. 15, pp. 970-974 (1995).

Gu et al., "Endocrine/Exocrine Intermediate Cells in Streptozotocin-Treated Ins-IFN-γ Transgenic Mice," Pancreas. vol. 15, No. 3 pp. 246-250 (1997).

Guarente, L., and Kenyon, C., "Genetic pathways that regulate ageing in model organisms," Nature. vol. 408 pp. 255-262 (2000).

Ha et al., "Müllerian Inhibiting Substance Inhibits Ovarian Cell Growth through an Rb-independent Mechanism," The Journal of Biological Chemistry. vol. 275, No. 47 pp. 37101-37109 (2000).

Halvorsen et al., "Accelerated telomere shortening and senescence in human pancreatic islet cells stimulated to divide in vitro," Journal of Endocrinology. vol. 166 pp. 103-109 (2000).

Hara et al., "Regulation of $p16^{CDKN2}$ Expression and Its Implications for Cell Immortalization and Senescence," Molecular and Cellular Biology. vol. 16, No. 3 pp. 859-867 (1996).

Haupt et al., "Mdm2 promotes the rapid degradation of p53," Nature. vol. 387 pp. 296-299 (1997).

Herzog et al., "$Cdkn2a$ Encodes Functional Variation of $p16^{INK4a}$ but not $p19^{ARF}$, Which Confers Selection in Mouse Lung Tumorigenesis," Molecular Carcinogenesis. vol. 25 pp. 92-98 (1999).

Hino et al., "In vivo proliferation of differentiated pancreatic islet beta cells in transgenic mice expressing mutated cyclin-dependent kinase 4," Diabetologia. vol. 47 pp. 1819-1830 (2004).

Huot et al., "Biallelic Mutations in $p16^{INK4a}$ Confer Resistance to Ras- and Ets-Induced Senescence in Human Diploid Fibroblasts," Molecular and Cellular Biology. vol. 22, No. 23 pp. 8135-8143 (2002).

Hussussian et al., "Germline p16 mutations in familial melanoma," Nature Genetics. vol. 8 pp. 15-21 (1994).

Jacks et al., "Tumor spectrum analysis in p53-mutant mice," Current Biology. vol. 4, No. 1 pp. 1-7 (1994).

Jacobs et al., "Senescence bypass screen identifies *TBX2*, which represses *Cdkn2a* ($p19^{ARF}$) and is amplified in a subset of human breast cancers," Nature Genetics. vol. 26 pp. 291-299 (2000).

Kahn, "Type 2 Diabetes: When Insulin Secretion Fails to Compensate for Insulin Resistance," Cell. vol. 92 pp. 593-596 (1998).

Kajstura et al., "Telomere Shortening Is an in Vivo Marker of Myocyte Replication and Aging," American Journal of Pathology. vol. 156, No. 3 pp. 813-819 (2000).

Kamb et al., "A Cell Cycle Regulator Potentially Involved in Genesis of Many Tumor Types," Science. vol. 264, No. 5157 pp. 436-440 (1994).

Kamb et al., "Analysis of the p16 gene (*CDKN2*) as a candidate for the chromosome 9p melanoma susceptibility locus," Nature Genetics. vol. 8 pp. 22-26 (1994).

Kamijo et al., "Functional and physical interactions of the ARF tumor suppressor with p53 and Mdm2,"PNAS. vol. 95 pp. 8292-8297 (1998).

Kamijo et al., "Loss of the ARF Tumor Suppressor Reverses Premature Replicative Arrest but not Radiation Hypersensitivity Arising from Disabled Atm Function," Cancer Research. vol. 59 pp. 2464-2469 (1999).

Kamijo et al., "Tumor Spectrum in *ARF*-deficient Mice," Cancer Research. vol. 59 pp. 2217-2222 (1999).

Kamijo et al., "Tumor Suppression at the Mouse *INK4a* Locus Mediated by the Alternative Reading Fram Product p19*ARF*," Cell. vol. 91 pp. 649-659 (1997).

Kim, W.Y., and Sharpless, N.E., "The Regulation of INK4/ARF in Cancer and Aging," Cell. vol. 127 pp. 265-275 (2006).

Kiyono et al., "Both Rb/$p16^{INK4a}$ inactivation and telomerase activity are required to immortalize human epithelial cells," Nature. vol. 396 pp. 84-88 (1998).

Klein-Szanto et al., "Melanosis and associated tumors in transgenic mice," PNAS. vol. 88 pp. 169-173 (1991).

Koh et al., "Tumour-derived p16 alleles encoding proteins defective in cell-cycle inhibition," Nature. vol. 375 pp. 506-510 (1995).

Kranc et al., "Transcriptional Coactivator Cited2 Induced Bmi1 and Mel18 and Controls Fibroblast Proliferation via Ink4a/ARF," Molecular and Cellular Biology. vol. 23, No. 21 pp. 7658-7666 (2003).

Kubbutat et al., "Regulation of p53 stability to Mdm2," Nature. vol. 387 pp. 299-303 (1997).

Kushner et al., "Cyclins D2 and D1 Are Essential for Postnatal Pancreatic β-Cell Growth," Molecular and Cellular Biology. vol. 25, No. 9 pp. 3752-3762 (2005).

Lakso et al., "Efficient in vivo manipulation of mouse genomic sequences at the zygote stage," PNAS. vol. 93 pp. 5860-5865 (1996).

Land et al., "Tumorigenic conversion of primary embryo fibroblasts requires at least two cooperating oncogenes," Nature. vol. 304 pp. 596-602 (1983).

Larue et al., "Genetic predisposition of transgenic mouse melanocytes to melanoma results in malignant melanoma after exposure to a low ultraviolet B intensity nontumorigenic for normal melanocytes," PNAS. vol. 89 pp. 9534-9538 (1992).

Lee et al., "Insertional mutagenesis identifies a member of the *Wnt* gene family as a candidate oncogene in the mammary epithelium of *int-2/Fgf-3* transgenic mice," PNAS. vol. 92 pp. 2268-2272 (1995).

Lin et al., "Premature senescence involving p53 and p16 is activated in response to constitutive MEK/MAPK mitogenic signaling," Genes & Development. vol. 12 pp. 3008-3019 (1998).

Liu et al., "Expression of p16INK4a in peripheral blood T-cells is a biomarker of human aging," Aging Cell. vol. 8, No. 4 pp. 439-448 (2009).

Lübbe et al., "Absence of p53 Gene Mutations in Cutaneous Melanoma," The Journal of Investigative Dermatology. vol. 102, No. 5 pp. 819-821 (1994).

Lukas et al., "Retinoblastoma-protein-dependent cell-cycle inhibition by the tumour suppressor p16," Nature. vol. 375 pp. 503-506 (1995).

Malumbres et al., "Inactivation of the cyclin-dependnet kinase inhibitor $p15^{INK4b}$ by deletion and *de novo* methylation with independnet of $p16^{INK4a}$ alterations in murine primary T-cell lymphomas," Oncogene. vol. 14 pp. 1361-1370 (1997).

Mao et al., "A Novel $p16^{INK4A}$ Transcript," Cancer Research. vol. 55 pp. 2995-2997 (1995).

Markel et al., "Theoretical and empirical issues for marker-assisted breeding of congenic mouse strains," Nature Genetics. vol. 17 pp. 280-284 (1997).

Martín et al., "Genetic rescue of Cdk4 *null* mice restores pancreatic β-cell proliferation but not homeostatic cell number," Oncogene. vol. 22 pp. 5261-5269 (2003).

Marzo et al., "Pancreatic islets from cyclin-dependent kinase 4/R24C (Cdk4) knockin mice have significantly increased beta cell mass and are physiologically functional, indicating that Cdk4 is a potential target for pancreatic beta cell mass regeneration in Type 1 diabetes," Diabetologia. vol. 47 pp. 686-694 (2004).

Masoro, "Subfield History: Caloric Restriction, Slowing Aging, and Extending Life," Sci. SAGE KE 2003:RE2 (7 pages).

Melk et al., "Expression of $p^{16INK4a}$ and other cell cycle regulator and senescence associated genes in aging human kidney," Kidney International. vol. 65 pp. 510-520 (2004).

Miller, "Genetics of Increased Longevity and Retarded Aging in Mice," Handbook of the Biology of Aging, $5^{th}$ Edition. Chapter 14 pp. 369-395 (2001).

Moll et al., "Second Primary Tumors in Patients with Hereditary Retinoblastoma: A Register-Based Follow-Up Study," International Journal of Cancer. vol. 67 pp. 515-519 (1996).

Nairn et al., "A CDKN2-like polymorphism in Xiphophorus LG V is associated with UV-B-induced melanoma formation in platyfish-swordtail hybrids," PNAS. vol. 93 pp. 13042-13047 (1996).

Nielsen et al., "Immunohistochemical Survey of $p16^{INK4A}$ Expression in Norman Human Adult and Infant Tissues," Laboratory Investigation. vol. 79, No. 9 pp. 1137-1143 (1999).

Noble et al., "Association of extended in vitro proliferative potential with loss of $p16^{INK4}$ expression," Oncogene. vol. 13 pp. 1259-1268 (1996).

Ohtani et al., "Opposing effects of Ets and Id proteins on p16INK4a expression during cellular senescence," Nature. vol. 409 pp. 1067-1070 (2001).

Pagano et al., "Role of the Ubiquitin-Proteasome Pathway in Regulating Abundance of the Cyclin-Dependent Kinase Inhibitor p27," Science. vol. 269, No. 5224 pp. 682-685 (1995).
Palmero et al., "p19$^{ARF}$ links the tumour suppressor p53 to Ras," Nature. vol. 395 pp. 125-126 (1998).
Park et al., "Bmi1, stem cells, and senescence regulation," The Journal of Clinical Investigation. vol. 113, No. 2 pp. 175-179 (2004).
Paumelle et al., "Hepatocyte growth factor/scatter factor activates the ETS1 transcription factor by a RAS-RAF-MEK-ERK signaling pathway," Oncogene. vol. 21 pp. 2309-2319 (2002).
Pei et al., "Genetic Evidence for Functional Dependency of p18$Ink4C$ on $Cdk4$," Molecular and Cellular Biology. vol. 24, No. 15 pp. 6653-6664 (2004).
Pham et al., "Long-range disruption of gene expression by a selectable marker cassette," PNAS. vol. 93 pp. 13090-13095 (1996).
Phelps et al., "Coupled Transcriptional and Translational Control of Cyclin-Dependent Kinase Inhibitor p18$INK4c$ Expression during Myogenesis," Molecular and Cellular Biology. vol. 18, No. 4 pp. 2334-2343 (1998).
Plettenberg et al., "Human Melanocytes and Melanoma Cells Constitutively Express the $Bcl$-2 Proto-Oncogene in Situ and in Cell Culture," American Journal of Pathology. vol. 146, No. 3 pp. 651-659 (1995).
Pomerantz et al., "The $Ink4a$ Tumor Suppressor Gene Product, p19$^{Art}$, Interacts with MDM2 and Neutralizes MDM2's Inhibition of p53," Cell. vol. 92 pp. 713-723 (1998).
Powell et al., "Hyperpigmentation and Melanocytic Hyperplasia in Transgenic Mice Expressing the Human T24 Ha-$ras$ Gene Regulated by a Mouse Tyrosinase Promoter," Molecular Carcinogenesis. vol. 12 pp. 82-90 (1995).
Prowse, K.R., and Greider, C.W., "Developmental and tissue-specific regulation of mouse telomerase and telomere length," PNAS. vol. 92 pp. 4818-4822 (1995).
Quelle et al., "Alternative Reading Frames of the $INK4a$ Tumor Suppressor Gene Encode Two Unrelated Proteins Capable of Inducing Cell Cycle Arrest," Cell. vol. 83 pp. 993-1000 (1995).
Quelle et al., "Cancer-associated mutations at the INK4a locus cancel cell cycle arrest by p16$^{INK4a}$ but not by the alternative reading frame protein p19$^{ARF}$," PNAS. vol. 94 pp. 669-673 (1997).
Radfar et al., "p19$^{Art}$ induces p53-dependent apoptosis during Abelson virus-mediated pre-B cell transformation," PNAS. vol. 95 pp. 13194-13199 (1998).
Randle et al., "Differential effects of p19$^{Art}$ and p16$^{Ink4a}$ loss on senescence of murine bone marrow-derived preB cells and macrophages," PNAS. vol. 98, No. 17 pp. 9654-9659 (2001).
Rane et al., "Loss of Cdk4 expression causes insulin-deficient diabetes and Cdk4 activation results in β-islet cell hyperplasia," Nature Genetics. vol. 22 pp. 44-52 (1999).
Rheinwald et al., "A Two-Stage, p16$^{INK4a}$- and p53-Dependent Keratinocyte Senescence Mechanism That Limits Replicative Potential Independent of Telomere Status," Molecular and Cellular Biology. vol. 22, No. 14 pp. 5157-5172 (2002).
Riley et al., "The Diabetogenic Effects of Streptozotocin in Mice are Prolonged and Inversely Related to Age," Diabetes. vol. 30 pp. 718-723 (1981).
Robertson, K.D., and Jones, P.A., "The Human ARF Cell Cycle Regulatory Gene Promoter Is a CpG Island Which Can Be Silenced by DNA Methylation and Down-Regulated by Wild-Type p53," Molecular and Cellular Biology. vol. 18, No. 11 pp. 6457-6473 (1998).
Robles, S.J., and Adami, G.R., "Agents that cause DNA double strand breaks lead to p16$^{INK4a}$ enrichment and the premature senescence of normal fibroblasts," Oncogene. vol. 16 pp. 1113-1123 (1998).
Rudolph et al., "Longevity, Stress Response, and Cancer in Aging Telomerase-Deficient Mice," Cell. vol. 96 pp. 701-712 (1999).
Russo et al., "Structural basis for inhibition of the cyclin-dependnet kinase Cdk6 by the tumour suppressor p16$^{INK4a}$," Nature. vol. 395 pp. 237-243 (1998).
Schmitt et al., "$INK4a/ARF$ mutations accelerate lymphomagenesis and promote chemoresistance by disabling p53," Genes & Development. vol. 13 pp. 2670-2677 (1999).

Serrano et al., "A new regulatory motif in cell-cycle control causing specific inhibition of cyciln D/CDK4," Nature. vol. 366 pp. 704-707 (1993).
Serrano et al., "Oncogenic $ras$ Provokes Premature Cell Senescence Associated with Accumulation of p53 and p16$^{INK4a}$," Cell. vol. 88 pp. 593-602 (1997).
Serrano et al., "Role of the $INK4a$ Locus in Tumor Suppression and Cell Mortality," Cell. vol. 85 pp. 27-37 (1996).
Shapiro et al., "p16$^{INK4A}$ Participates in a $G_1$ Arrest Checkpoint in Response to DNA Damage," Molecular and Cellular Biology. vol. 18, No. 1 pp. 378-387 (1998).
Sharpless, N.E., and DePinho, R.A., "How stem cells age and why this makes us grow old," Nature. vol. 8 pp. 703-713 (2007).
Sharpless, N.E., and DePinho, R.A., "p53: Good Cop/Bad Cop," Cell. vol. 110 pp. 9-12 (2002).
Sharpless et al., "The differential impact of p16$^{INK4a}$ or p19$^{ARF}$ deficiency on cell growth and tumorigenesis," Oncogene. vol. 23 pp. 379-385 (2004).
Sherr, "Cancer Cell Cycles," Science. vol. 274, No. 5293 pp. 1672-1677 (1996).
Sherr, "The Pezcoller Lecture: Cancer Cell Cycles Revisited," Cancer Research. vol. 60 pp. 3689-3695 (2000).
Sherr, C.J., and DePinho, R.A., "Cellular Senescence: Mitotic Clock or Culture Shock?" Cell. vol. 102 pp. 407-410 (2000).
Sherr, C.J., and Roberts, J.M., "CDK inhibitors: positive and negative regulators of $G_1$-phase progression," Genes & Development. vol. 13 pp. 1501-1512 (1999).
Smith, J.R., and Whitney, R.G., "Intraclonal Variation in Proliferative Potential of Human Diploid Fibroblasts: Stochastic Mechanism for Cellular Aging," Science. vol. 207, No. 4426 pp. 82-84 (1980).
Stone et al., "Complex Structure and Regulation of the $P16$ ($MTS1$) Locus," Cancer Research. vol. 55 pp. 2988-2994 (1995).
Stott et al., "The alternative product from the human $CDKN2A$ locus, p14$^{ARF}$, participates in a regulatory feedback loop with p53 and MDM2," The EMBO Journal. vol. 17, No. 17 pp. 5001-5014 (1998).
Tanaka et al., "Induction of Ets-1 in Endothelial Cells During Reendothelialization After Denuding Injury," Journal of Cellular Physiology. vol. 176 pp. 235-244 (1998).
Traboulsi et al., "Cutaneous Malignant Melanoma in Survivors of Heritable Retinoblastoma," Arch. Ophtalmol. vol. 106 pp. 1059-1061 (1988).
Tsutsui et al., "Targeted Disruption of CDK4 Delays Cell Cycle Entry with Enhanced p27$^{Kip1}$ Activity," Molecular and Cellular Biology. vol. 19, No. 10 pp. 7011-7019 (1999).
Tyner et al., "p53 mutant mice that display early ageing-associated phenotypes," Nature. vol. 415 pp. 45-53 (2002).
Uchida, N., and Weissman, I.L., "Searching for Hematopoietic Stem Cells: Evidence That Thy-1.1$^{lo}$ Lin$^-$Sca-1+ Cells Are the Only Stem Cells in C57BL/Ka-Thy-1.1 Bone Marrow," J. Exp. Med. vol. 175 pp. 175-184 (1992).
van Lohuizen et al., "Identification of Cooperating Oncogenes in Eμ-$myc$ Transgenic Mice by Provirus Tagging," Cell. vol. 65 pp. 737-752 (1991).
Wakeland et al., "Speed congenics: a classic technique in the fast lane (relatively speaking)," Immunology Today. vol. 18, No. 10 pp. 472-477 (1997).
Wasylyk et al., "Conserved mechanisms of Ras regulation of evolutionary related transcription factors, Ets1 and Pointed P2," Oncogene. vol. 14 pp. 899-913 (1997).
Weber et al., "Nucleolar Arf sequesters Mdm2 and activates p53," Nature Cell Biology. vol. 1 pp. 20-27 (1999).
Wölfel et al., "A p16$^{INK4a}$-Insensitive CDK4 Mutant Targeted by Cytolytic T Lymphocytes in a Human Melanoma," Science. vol. 269, No. 5228 pp. 1281-1284 (1995).
Yoshimi et al., "Telomerase Activity of Normal Tissues and Neoplasms in Rat Colon Carcinogenesis Induced by Methylazoxymethanol Acetate and Its Difference From That of Human Colonic Tissues," Molecular Carcinogenesis. vol. 16 pp. 1-5 (1996).
Yu et al., "Life Span Study of SPF Fischer 344 Male Rats Fed $Ad$ $Libitum$ or Restricted Diets: Longevity, Growth, Lean Body Mass and Disease," Journal of Gastroenterology. vol. 37, No. 2 pp. 130-141 (1982).

Zhang et al., "ARF Promotes MDM2 Degradation and Stabilizes p53: ARF-INK4a Locus Deletion Impairs Both the Rb and p53 Tumor Suppression Pathways," Cell. vol. 92 pp. 725-734 (1998).

Zhang et al., "Cdkn2a, the cyclin-dependent kinase inhibitor encoding p16$^{INK4a}$ and p19$^{ARF}$ is a candidate for the plasmacytoma susceptibility locus, Pctr1," PNAS. vol. 95 pp. 2429-2434 (1998).

Zhang et al., "Mutations in Human $^{ARF}$ Exon 2 Disrupt Its Nucleolar Localization and Impair Its Ability to Block Nuclear Export of MDM2 and p53," Molecular Cell. vol. 3 pp. 579-591 (1999).

Zhu et al., "Modulation of the Expression of p16$^{INK4a}$ and p14$^{ARF}$ by hnRNP A1 and A2 RNA Binding Proteins: Implications for Cellular Senescence," Journal of Cellular Physiology. vol. 193 pp. 19-25 (2002).

Zhu et al., "Senescence of human fibroblasts induced by oncogenic Raf," Genes & Development. vol. 12 pp. 2997-3007 (1998).

Zindy et al., "INK4d-Deficient Mice Are Fertile Despite Testicular Atrophy," Molecular and Cellular Biology. vol. 20, No. 1 pp. 372-378 (2000).

Zindy et al., "Myc signaling via the ARF tumor suppressor regulates p53-dependnet apoptosis and immortalization," Genes & Development. vol. 12 pp. 2424-2433 (1998).

Zuo et al., "Germline mutations in the p16$^{INK4a}$ binding domain of CDK4 in familial melanoma," Nature Genetics. vol. 12 pp. 97-99 (1996).

Bartke et al., "Extending the lifespan of long-lived mice," Nature, vol. 414, p. 412 (2001).

Bulavin et al., "Inactivation of the Wip1 phosphatase inhibits mammary tumorigenesis through p38 MAPK—mediated activation of the p16$^{Ink4a}$-p19$^{Arf}$ pathway," Nat. Genet., vol. 36, pp. 343-350 (2004).

Dimri et al., "A biomarker that identifies senescent human cells in culture and in aging skin in vivo," Proc. Natl. Acad. Sci. U.S.A., vol. 92, pp. 9363-9367 (1995).

Genbank® Accession No. AAC08963.
Genbank® Accession No. AAD48924.
Genbank® Accession No. AAL76337.
Genbank® Accession No. AF044336.
Genbank® Accession No. AF115544.
Genbank® Accession No. AF474975.
Genbank® Accession No. L81167.
Genbank® Accession No. NM_007552.
Genbank® Accession No. NM_007669.
Genbank® Accession No. NM_007670.
Genbank® Accession No. NM_007671.
Genbank® Accession No. NM_008084.
Genbank® Accession No. NM_009875.
Genbank® Accession No. NM_009877.
Genbank® Accession No. NM_011808.
Genbank® Accession No. NM_012555.
Genbank® Accession No. NM_012797.
Genbank® Accession No. NM_013684.
Genbank® Accession No. NM_058195.
Genbank® Accession No. NM_080782.
Genbank® Accession No. NP_034007.
Genbank® Accession No. NP_478102.
Genbank® Accession No. P42771.
Genbank® Accession No. X03205.

Goldstein, "Replicative senescence: the human fibroblast comes of age," Science, vol. 249, pp. 1129-1133 (1990).

Goldstein et al., "Diabetes Mellitus and Aging: Diminished Plating Efficiency of Cultured Human Fibroblasts," Proc. Natl. Acad. Sci. U.S.A., vol. 64, pp. 155-160 (1969).

Ham & McKeehan, "Media and Growth Requirements," Meth. Enzymol., vol. 58, pp. 44-93 (1979).

Harley, "Telomere loss: mitotic clock or genetic time bomb?" Mutation Research, vol. 256, pp. 271-282 (1991).

Harley et al., "Telomeres shorten during ageing of human fibroblasts," Nature, vol. 345, pp. 458-460 (1990).

Hayflick & Moorehead, "The Serial Cultivation of Human Diploid Cell Strains," Exp. Cell Res., vol. 25, pp. 585-621 (1961).

Hayflick, "The Limited In Vitro Lifetime of Human Diploid Cell Strains," Exp. Cell Res., vol. 37, pp. 614-636 (1965).

Hayflick, "Aging, Longevity, and Immortality In Vitro," Exp. Gerontol., vol. 27, pp. 363-368 (1992).

Jacobs et al., "The oncogene and Polycombgroup gene bmi-1regulates cell proliferation and senescence through the ink4a locus," Nature, vol. 397, pp. 164-168 (1999).

Lessard & Sauvageau, "Bmi-1 determines the proliferative capacity of normal and leukaemic stem cells," Nature, vol. 423, pp. 255-260 (2003).

Leung et al., "Bmi1 is essential for cerebellar development and is overexpressed in human medulloblastomas," Nature 428, pp. 337-341 (2004).

Lewis et al., "The influence of INK4 proteins on growth and self-renewal kinetics of kinetics of hematopoietic progenitor cells," Blood, vol. 97, pp. 2604-2610 (2001).

Martin et al., "Clonal Selection, Attenuation and Differentiation in an In Vitro Model of Hyperplasia," Am. J. Pathol. vol. 74, pp. 137-154 (1974).

Melk et al., "Cell senescence in rat kidneys in vivo increases with growth and age despite lack of telomere shortening," Kidney Int., vol. 63, pp. 2134-2143 (2003).

Meng et al., "Ionizing Radiation and Busulfan Induce Premature Senescence in Murine Bone Marrow Hematopoietic Cells," Cancer Res., vol. 63, pp. 5414-5419 (2003).

Mikaelian et al., "Antibodies That Label Paraffin-Embedded Mouse Tissues: A Collaborative Endeavor," Toxicol. Pathol., vol. 32, pp. 181-191 (2004).

Miller et al., "Gene Expression Patterns in Calorically Restricted Mice: Partial Overlap with Long-Lived Mutant Mice," Mol. Endocrinol., vol. 16, pp. 2657-2666 (2002).

Molofsky et al., "Bmi-1 dependence distinguishes neural stem cell self-renewal from progenitor proliferation," Nature, vol. 425, pp. 962-967 (2003).

Ohno, "Strict Relationship Between Dialyzed Serum Concentration and Cellular Life Span In Vitro," Mech. Aging Dev., vol. 11, pp. 179-183 (1979).

Olovnikov, "A Theory of Marginotomy—The Incomplete Copying of Template Margin in Enzymic Synthesis of Polynucleotides and Biological Significance of the Phenomenon," J. Theoretical Biology, vol. 41, pp. 181-190 (1973).

Park et al., "Bmi-1 is required for maintenance of adult self-renewing haematopoietic stem cells," Nature, vol. 423, pp. 302-305 (2003).

Ruas & Peters, "The p16$^{INK4a}$/CDKN2A tumor suppressor and its relatives," Biochim. Biophys. Acta, vol. 1378, pp. F115-F177 (1998).

Sharpless et al., "Loss of p16$^{Ink4a}$ with retention of p19Arf predisposes mice to tumorigenesis," Nature, vol. 413, pp. 86-91 (2001).

Shay & Wright, "Quantitation of the Frequency of Immortalization of Normal Human Diploid Fibroblasts by SV40 Large T-Antigen," Exp. Cell Res., vol. 184, pp. 109-118 (1989).

Shay et al., "A Role for Both RB and p53 in the Regulation of Human Cellular Senescence," Exp. Cell Res., vol. 196, pp. 33-39 (1991).

Shay et al., "Re-Expression of Senescent Markers in Deinduced Reversibly Immortalized Cells," Exp. Gerontol., vol. 27, pp. 477-492 (1992).

Sun et al., "Growth retardation and premature aging phenotypes in mice with disruption of the SNF2-like gene, PASG," Genes Dev., vol. 8, pp. 1035-1046 (2004).

Turturro et al., "Growth curves and survival characteristics of the animals used in the Biomarkers of Aging Program," J. Gerontol., Series A, Biol. Sci. Med. Sci., vol. 54, pp. B492-B501 (1999).

* cited by examiner

DETERMINATION OF MOLECULAR AGE BY DETECTION OF INK4A/ARF EXPRESSION

CROSS REFERENCE TO RELATED APPLICATIONS

This application is based on and claims priority to U.S. Provisional Application Ser. No. 60/613,296, filed Sep. 27, 2004, the disclosure of which is herein incorporated by reference in its entirety.

GRANT STATEMENT

This work was supported by grants AG19899 and CA090679 from the National Institutes of Health. Thus, the U.S. government has certain rights in the presently disclosed subject matter.

TECHNICAL FIELD

The presently disclosed subject matter relates, in general, to methods for determining the molecular or physiologic age of a cell or tissue. More particularly, the presently disclosed subject matter relates to methods of determining the molecular or physiologic age of a cell or tissue by determining the level of expression of $p16^{INK4a}$, ARF, or both $p16^{INK4a}$ and ARF in the cell or tissue, the level of expression being indicative of the molecular or physiologic age of a cell or tissue.

BACKGROUND

Normal human somatic cells, such as fibroblasts, endothelial cells, and epithelial cells, are characterized by a finite capacity to divide in vitro, after which they cease proliferating even in the presence of adequate growth factors. Typically, such cells are limited to about 50-100 in vitro doublings, after which they cease to divide. This cessation of replication in vitro is generally referred to as cellular senescence. See e.g., Goldstein, 1990; Hayflick & Moorehead, 1961; Hayflick, 1965; Ohno, 1979; Ham & McKeehan, 1979. Furthermore, the replicative life span of cells grown in vitro is often inversely proportional to the in vivo age of the donor (Martin et al., 1970; Goldstein et al., 1969; Schneider & Mitsui, 1976).

Some cells are able to escape cellular senescence, thereby retaining or perhaps acquiring unlimited replicative capacity in vitro (Shay et al., 1991). Such cells are generally referred to as "immortalized" to reflect the ability to remain replicatively competent over hundreds or even thousands of passages in culture. The immortalization process appears to involve one or more mutagenic events or the aid of transforming viral oncoproteins, and even then the frequency of immortalization is only about $10^{-6}$ to $10^{-7}$ in human cells (Shay & Wright, 1989). Thus, with the exception of germ cells and perhaps certain stem cells, mammalian somatic cells are mortal and can only be maintained for relatively short periods in culture.

A variety of hypotheses have been proposed over the years to explain the causes of cellular senescence, and it is clear that senescence and can result from several independent stimuli such as cancer-causing mutations (oncogene activation), oxidative stress, artifacts of cell culture, and telomere shortening. It should be noted, however, that no consensus has been reached concerning the cause of cellular senescence in the whole organism as opposed to in vitro, nor is the role of cellular senescence in organismal aging clearly established.

One theory that relates in senescence and aging is referred to as the free radical theory. The free radical theory of aging suggests that free radicals damage DNA and other macromolecules resulting in critical losses of cell and/or tissue functions (Harman, 1956; Harman, 1961). The somatic mutation theories propose that the progressive accumulation of genetic damage to somatic cells by radiation and other environmental insults impairs cell function and that somatic cells because somatic cells lack the ability to repair the damage through recombination, they fail to proliferate indefinitely (Burnet, 1974; Hayflick, 1992).

Shay et al. describe a two-stage model for human cell mortality to explain the ability of Simian Virus 40 (SV40) T-antigen to immortalize human cells. This model likely explains a subset of the forms of cellular senescence, and is not mutually exclusive with other theories as senescence such as the free radical theory (that is, certain forms of DNA damage may alter telomere structure to induce senescence). See Shay et al., 1991 and Shay et al., 1992. The mortality stage 1 mechanism (M1) is the target of certain tumor virus proteins, and an independent mortality stage 2 mechanism (M2) produces crisis and prevents these tumor viruses from directly immortalizing human cells. These authors utilized T-antigen driven by a mouse mammary tumor virus promoter to cause reversible immortalization of cells. The Simian Virus 40 T-antigen is said to extend the replicative life span of human fibroblast by an additional 40-60%. The authors have established that the M1 mechanism is overcome by T-antigen binding to various cellular proteins (p53 and RB). The M2 mechanism then causes cessation of proliferation, even though the M1 mechanism is blocked. Immortality is achieved only when the M2 mortality mechanism is also disrupted. It is now known that both M1 and M2 result from alterations of telomere structure in some models of senescence in human cells.

Numerous publications have suggested that aspects of telomere length and replication are associated with cellular senescence. It has also been proposed that the finite replicative capacity of cells might reflect the work of a "clock" linked to DNA synthesis in the telomere (end part) of the chromosomes. In 1973, Olovnikov described the theory of marginotomy to explain the limitations of cell doubling potential in somatic cells. He stated that an:

informative oligonucleotide, built into DNA after a telogene and controlling synthesis of a repressor of differentiation, might serve as a means of counting mitosis performed in the course of morphogenesis. Marginotomic elimination of such an oligonucleotide would present an appropriate signal for the beginning of further differentiation. Lengthening of the telogene would increase the number of possible mitoses in differentiation.

Olovnikov, 1973. Harley et al. stated that the amount and length of telemetric DNA in human fibroblasts decreases as a function of serial passage during aging in vitro, and possibly in vivo, but do not know whether this loss of DNA has a causal role in senescence (Harley et al., 1990). They point out, however, that:

Tumour cells are also characterized by shortened telomeres and increased frequency of aneuploidy, including telomeric associations. If loss of telomeric DNA ultimately causes cell-cycle arrest in normal cells, the final steps in this process may be blocked in immortalized cells. Whereas normal cells with relatively long telomeres and a senescent phenotype may contain little or no telomerase activity, tumour cells with short telomeres may have significant telomerase activity. Telomerase may therefore be an effective target for anti-tumour drugs.

Thus, it appears that cellular senescence might correlate with telomere shortening over the life span of the mammal. In fact, Harley discusses observations allegedly showing that telomeres of human somatic cells act as a mitotic clock shortening with age both in vitro and in vivo in a replication dependent manner. He states:

> Telomerase activation may be a late, obligate event in immortalization since many transformed cells and tumour tissues have critically short telomeres. Thus, telomere length and telomerase activity appear to be markers of the replicative history and proliferative potential of cells; the intriguing possibility remains that telomere loss is a genetic time bomb and hence causally involved in cell senescence and immortalization . . .
>
> Despite apparently stable telomere length in various tumour tissues or transformed cell lines, this length was usually found to be shorter than those of the tissue of origin. These data suggest that telomerase becomes activated as a late event in cell transformation, and that cells could be viable (albeit genetically unstable) with short telomeres stably maintained by telomerase. If telomerase was constitutively present in a small fraction of normal cells, and these were the ones which survived crisis or became transformed, we would expect to find a greater frequency of transformed cells with long telomeres.

Harley, 1991 (Citations Omitted).

In the non-malignant cell, it appears that several signals such as telomere shortening and oxidative stress can provoke senescence. Nonetheless, while cellular aging and telomere shortening might generally correlate in vitro and/or in vivo, the observation that many tumor cells have critically shortened telomeres makes indicates that telomere length is not an absolute predictor of the molecular or physiologic age of a cell.

Thus, there is a long-felt and continuing need in the art for new methods for determining the molecular or physiologic age of a cell or tissue.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for determining the molecular age of a cell or tissue in a subject. In some embodiments, the methods comprise (a) providing a sample from the cell or tissue; (b) quantifying a level of expression of $p16^{INK4a}$, ARF, or both $p16^{INK4a}$ and ARF in the sample; and (c) comparing the level of expression of $p16^{INK4a}$, ARF, or both $p16^{INK4a}$ and ARF to a standard to thereby determine a molecular age of the cell or tissue.

The presently disclosed subject matter also provides methods for predicting a predisposition to disease progression in a cell or tissue in a subject. In some embodiments, the methods comprise (a) providing a sample from the cell or tissue; (b) quantifying a level of expression of $p16^{INK4a}$, ARF, or both $p16^{INK4a}$ and ARF in the sample; and (c) comparing the level of expression of $p16^{INK4a}$, ARF, or both $p16^{INK4a}$ and ARF to a standard to thereby predict a predisposition to disease progression in the cell or tissue in the subject. In some embodiments, the disease comprises a premorbid syndrome in the cell or tissue in the subject. In some embodiments, the premorbid syndrome is selected from the group consisting of HIV-associated illness, atherosclerosis, bone-marrow failure syndromes, congenital defects of DNA repair, renal insufficiency and cardiomyopathy.

The presently disclosed subject matter also provides methods for predicting a tendency to therapy-induced toxicity in a cell or tissue in a subject. In some embodiments, the methods comprise (a) providing a sample from the cell or tissue; (b) quantifying a level of expression of $p16^{INK4a}$, ARF, or both $p16^{INK4a}$ and ARF in the sample; and (c) comparing the level of expression quantified with a standard to thereby predict a tendency to therapy-induced toxicity in the cell or tissue in the subject.

The presently disclosed subject matter also provides methods for determining suitability of a subject for a cell or tissue donation. In some embodiments, the methods comprise (a) providing a sample from the cell or tissue; (b) quantifying a level of expression of $p16^{INK4a}$, ARF, or both $p16^{INK4a}$ and ARF in the sample; and (c) comparing the level of expression quantified with a standard to thereby determine suitability of a subject for donating the cell or tissue. In some embodiments, the cell or tissue donation is appropriate for a transplant selected from the group consisting of bone marrow transplant, solid organ transplant, and tissue graft transplant.

In some embodiments of the methods disclosed herein, the sample comprises a cell or tissue selected from the group consisting of an adrenal gland cell, a bone marrow cell, a cecum cell, a brain cortex cell, a duodenum cell, a heart cell, a kidney cell, a liver cell, a lung cell, a lymph node cell, an ovary cell, a pancreas cell, a spleen cell, a testis cell, and a uterus cell.

In some embodiments of the disclosed methods, the methods further comprise purifying a particular cell type from the tissue. In some embodiments, the particular cell type comprises a lymphocyte, a stem cell, a neural cell, and an islet cell.

In some embodiments of the disclosed methods, the standard comprises a quantification of a level of expression of $p16^{INK4a}$, ARF, or both $p16^{INK4a}$ and ARF in the cell or tissue in a population of same species individuals as the subject. In some embodiments of the disclosed methods, the standard comprises a quantification of a level of expression of $p16^{INK4a}$, ARF, or both $p16^{INK4a}$ and ARF in the cell or tissue in the subject at an earlier time. In some embodiments of the disclosed methods, the standard comprises a quantification of a level of expression of $p16^{INK4a}$, ARF, or both $p16^{INK4a}$ and ARF in a second sample isolated from a different tissue of the subject. In some embodiments, the cell or tissue and the at least one different tissue all comprise a cell selected from the group consisting of an adrenal gland cell, a bone marrow cell, a cecum cell, a brain cortex cell, a duodenum cell, a heart cell, a kidney cell, a liver cell, a lung cell, a lymph node cell, an ovary cell, a pancreas cell, a spleen cell, a testis cell, and a uterus cell.

In some embodiments of the disclosed methods, the quantifying employs quantitative real-time polymerase chain reaction analysis. In some embodiments of the disclosed methods, the quantifying a level further comprises determining an increased level of expression of $p16^{INK4a}$, ARF, or both $p16^{INK4a}$ and ARF, and the increased level of expression indicates increased molecular age of the tissue relative to the standard.

In some embodiments of the disclosed methods, the comparing is to a level of expression of $p16^{INK4a}$, ARF, or both $p16^{INK4a}$ and ARF in the target cell type in a population of same species individuals as the subject.

In some embodiments of the disclosed methods, the methods further comprise purifying a particular cell type from the tissue. In some embodiments, the particular cell type comprises a lymphocyte, a stem cell, a neural cell, and an islet cell. In some embodiments of the disclosed methods, the methods further comprise normalizing the level of expression quantified to a level of expression of a housekeeping gene.

The presently disclosed subject matter also provides methods for screening a presumptive anti-aging compound for an effect on a physiologic age of a cell. In some embodiments, the methods comprise (a) providing the presumptive anti-aging compound to the cell; and (b) comparing expression of $p16^{INK4a}$, ARF, or both $p16^{INK4a}$ and ARF in the cell before and after the providing step, wherein the providing modulates the expression of $p16^{INK4a}$, ARF, or both $p16^{INK4a}$ and ARF in the cell. In some embodiments, the cell is present in an animal and the presumptive anti-aging compound is provided to the animal. In some embodiments, the presumptive anti-aging compound is provided to the animal systemically or locally to the cell. In some embodiments, the cell is an in vitro cultured cell.

The disclosed methods can be applied to subjects of any species including but not limited to mammals. In some embodiments of the disclosed methods, the subject is a human.

The presently disclosed subject matter also provides kits for performing the disclosed methods. In some embodiments, the kits comprise (a) a primer pair specific for a $p16^{INK4a}$ gene or a ARF gene; and (b) a set of instructions for employing the primer pair for determining a level of expression of the $p16^{INK4a}$ gene or the ARF gene. In some embodiments, the primer pair comprises nucleotide sequences as set forth in at least two of SEQ ID NOs: 13-24, 28-33, and 34-39. In some embodiments, the primer pair is specific for a human $p16^{INK4a}$ gene or a human ARF gene. In some embodiments, the kit comprises at least two primer pairs, and wherein at least one primer pair is specific for a $p16^{INK4a}$ gene and at least one primer pair is specific for an ARF gene. In some embodiments, the primer pair comprises a first primer and a second primer, and the first primer, the second primer, or both the first and second primer comprise a detectable label. In some embodiments, the detectable label is a fluorescent label. In some embodiments, the kit further comprises a primer pair specific for a control gene. In some embodiments, the control gene is selected from the group consisting of an 18S rRNA gene, a glucose-6-phosphate dehydrogenase gene, a phosphoglycerate kinase 1 gene, a β-actin gene, an elongation factor-1 gene, an elongation factor-2 gene, and a beta-2-microglobulin gene. In some embodiments, the kit further comprises a probe for detecting a polymerase chain reaction product produced using the primer pair.

Accordingly, it is an object of the presently disclosed subject matter to provide a method for determining the molecular or physiologic age of a cell, tissue, or organ. This and other objects are achieved in whole or in part by the presently disclosed subject matter.

An object of the presently disclosed subject matter having been stated above, other objects and advantages will become apparent to those of ordinary skill in the art after a study of the following Description of the presently disclosed subject matter, Figures and non-limiting Examples.

BRIEF DESCRIPTION OF THE DRAWINGS

FIG. 1A depicts relative expression of the ratios ($\log_2$ scale) of the expression of cell cycle inhibitors in old (26 months) to young (2.5 months) mice from 15 tissues (left to right per group: adrenal, bone marrow, cecum, cortex, duodenum, heart, kidney, liver, lung, lymph node, ovary, pancreas, spleen, testis, and uterus, with the final bar depicting the geometric mean of these tissues) ±SEM. Each estimate represents the mean of 8-32 quantitative RT-PCR reactions on independent RNA samples derived from 4-6 mice. *:Minimum estimate of old/young ratio.

FIG. 1B depicts absolute copy numbers of $p16^{INK4a}$ and ARF mRNA molecules (log 10 scale) per 90 ng total RNA RT-PCR from 15 tissues of young (2.5 months) and old (26 months) mice ±SEM. For each group, the first bar depicts $p16^{INK4a}$ young, the second bar depicts ARF young, the third bar depicts $p16^{INK4a}$ old, and the second bar depicts ARF old. Murine embryo fibroblasts (MEFs) at early (P4) and late (P7) passage are shown for comparison. #: Maximum estimated expression is indicated, as expression was below the level of detection.

FIG. 2A depicts immunoperoxidase staining performed on paraffin-embedded sections of germ-line $p16^{INK4a}$-deficient (KO), WT young (3.5 months), and WT old (25 months) murine tissues using an anti-$p16^{INK4a}$ antibody. Positively staining cells demonstrate both nuclear and cytoplasmic expression. GC: germinal center.

FIG. 2B depicts relative expression ratios (old/young, log2 scale) of $p16^{INK4a}$ in specific compartments (average purity >94% for all fractions) of bone marrow (lin$^-$, 2%; lin$^+$, 97%), spleen (B220$^+$, 48%; Mac1$^+$, 9%; B220$^-$ Mac1$^-$, 22%), and lymph node. Asterisks indicate that $p16^{INK4a}$ expression was undetectable in these cell populations from young mice, and therefore a minimum estimate of the fold increase is shown.

FIG. 3A depicts the relative expression ratios (old/young, $\log_2$ scale) of cell cycle inhibitors in 7 tissues derived from old (28 months) and young (3 months) AL or CR F344 rats. The relative ratios are graphed ±SEM. Each estimate represents the mean of 8-16 quantitative PCR reactions on independent RNA samples derived from 4 rats.

FIG. 3B depicts immunoperoxidase staining on paraffin-embedded kidney sections from young, old AL, and old CR F344 rats using an anti-$p16^{INK4a}$ antibody. G: glomeruli seen in cortical sections.

FIG. 3C depicts SA-β-gal staining in AL and CR mouse and rat kidney. C: renal cortex; M: renal medulla. Thin tissue slices were stained for mice, as opposed to small tissue wedges for rats. SA-β-gal activity is predominantly restricted to the renal cortex.

FIG. 3D depicts relative expression ratios (old/young, log2 scale) of Ets-1 in kidneys derived from AL and CR rats and mice. Results from the kidneys from AL and CR mice with and without GHR deficiency are also shown. Each estimate represents the mean of 8-32 quantitative RT-PCR reactions on independent RNA samples derived from 8 mice or 4 rats.

FIG. 6A depicts a scatter plot (log2 scale, both axes) of the ratios (old/young) of p16$^{INK4a}$ expression versus the expression ratios (old/young) of ARF, Ets-1, and Id1 seen in the corresponding tissue (n=22-70 data pairs per gene from up to 15 tissues in both mouse and rat). Each ratio represents a mean value of multiple measurements per tissue as described in Example 3 and the Materials and Methods for Examples 1-3. A best-fit line determined by linear regression is shown for each data series, with Pearson correlation coefficient and 2-tailed P value. No significant correlation was seen between ARF and Ets-1, or between ARF or p16$^{INK4a}$ and Bmi-1.

FIG. 6B depicts relationships and covariances among aging, senescence, and expression levels of Ets-1, ARF, and p16$^{INK4a}$. Arrows show known or inferred transcriptional relationships, and numbers indicate the covariances ($r^2$) for the linked elements as determined in FIG. 6A. As p16$^{INK4a}$ and ARF do not regulate one another, it seems reasonable to assume that an unknown co-regulator (X) modulates the expression of both transcripts with aging, explaining their strong correlation ($r^2$=48%). Furthermore, as ARF and Ets-1 do not covary, X and Ets-1 must be independent X need not represent a single transcription factor: it might represent the combined activity of several genes (e.g., the PcG family members) or genes that affect other transcript properties, such as message stability. This model suggests that the majority (87%) of the variance in p16$^{INK4a}$ expression with aging in the analyzed tissues can be attributed to the activity of X and Ets-1.

FIG. 10a presents Kaplan Meier survival curves of C57Bl/6 mice of indicated genotypes post STZ (given on day 0) of 5-9 week old mice. N=23 p16$^{INK4a}$ +/+ and +/− mice, and 11 p16$^{INK4a}$ −/− mice. Indicated p-values determined by log-rank test.

FIG. 10b presents Kaplan Meier survival curves post STZ of 9-15 week old mice. N=21 p16$^{INK4a}$ +/+ and +/−mice, and 10 p16$^{INK4a}$ −/− mice.

FIG. 10c presents Kaplan Meier survival curves post STZ of 20-28 week old mice. N=8 p16$^{INK4a}$ +/+ and +/−mice, and 7 p16−/− mice.

FIG. 10d is a graph showing animal weight normalized to pre-treatment weight post-STZ of long-term (>100 days) surviving mice. All long-term surviving improved hyperglycemia and began to regain weight within 55 days post-STZ, regardless of genotype. Results are shown +/− standard error of the mean (SEM).

BRIEF DESCRIPTION OF THE SEQUENCE LISTING

Figure 1:
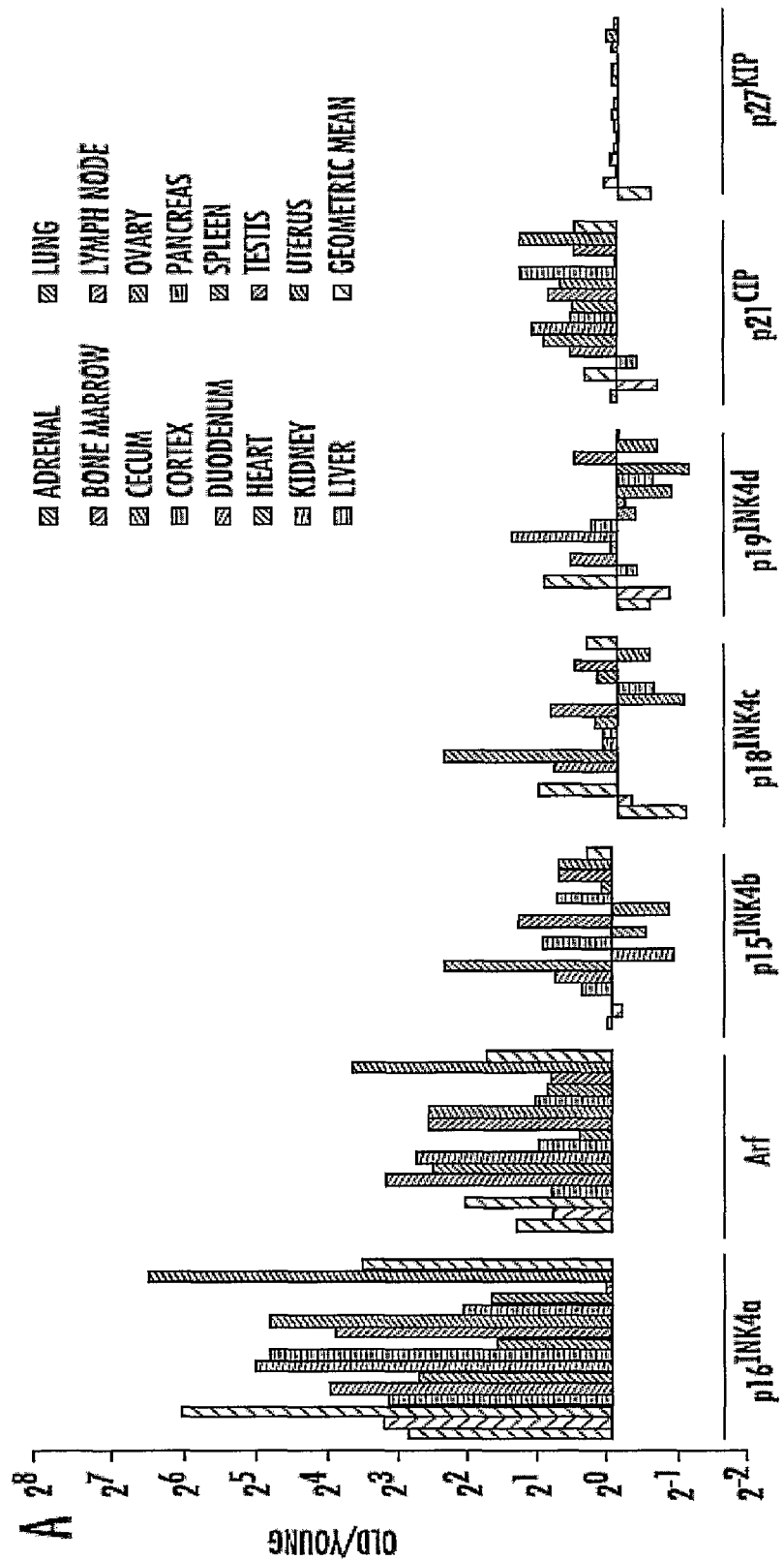
FIGS. 1A and 1B depict increased expression of the Ink4a/ARF locus with aging in representative tissues.
Figure 1:
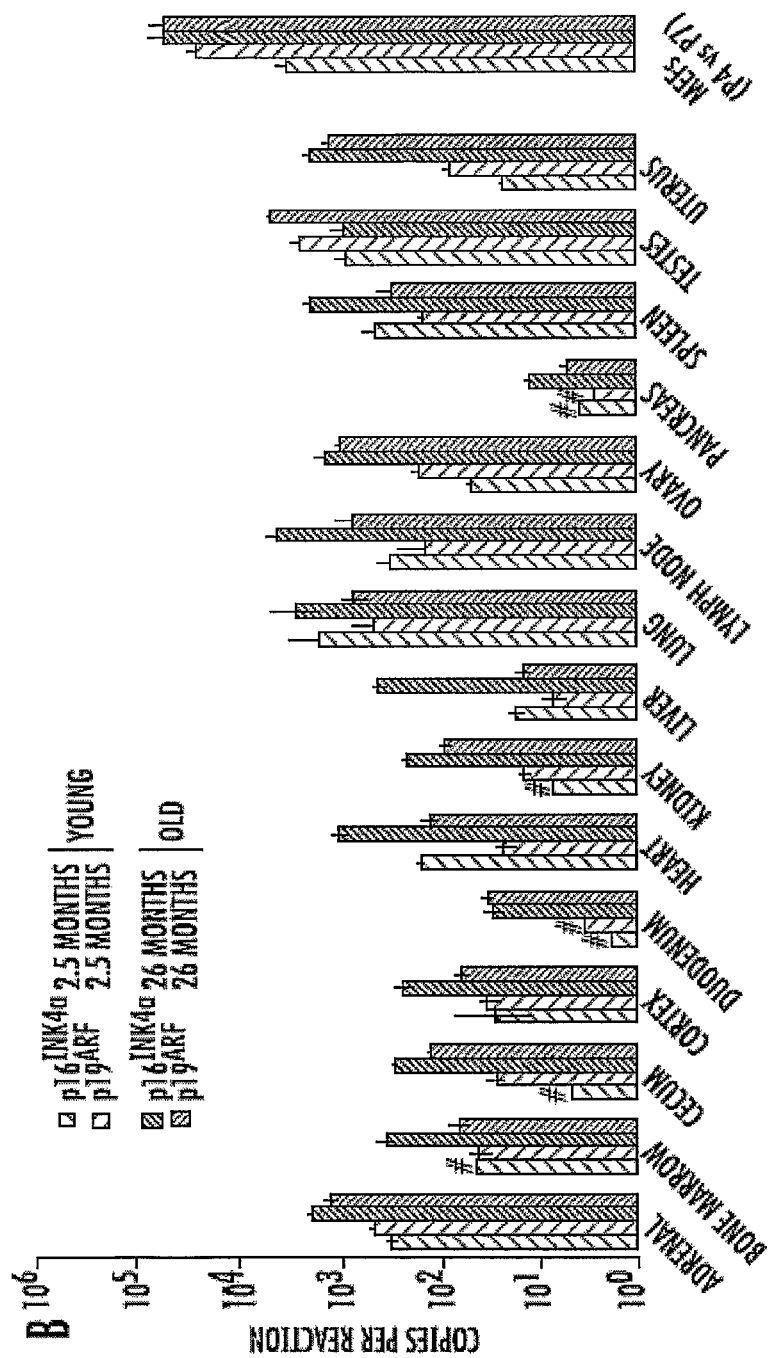

The Sequence Listing discloses, inter alia, the nucleic acid and amino acid sequences of various genes relevant to the practice of the presently disclosed subject matter. It is understood that the sequences presented herein represent only a subset of the sequences that can be employed in the practice of the presently disclosed subject matter, and that other sequences including, but not limited to the nucleic acid and amino acid sequences of INK4a and ARF genes from other species can also be employed.

SEQ ID NOs: 1 and 2 are nucleic acid and amino acid sequences, respectively, of a human p16$^{INK4a}$ gene product, and correspond to GENBANK® Accession Nos. AF115544 and P42771, respectively. Bases 1-351 make up the open reading from of AF115544 presented in SEQ ID NO: 3.

SEQ ID NOs: 3 and 4 are nucleic acid and amino acid sequences, respectively, of a human p14$^{ARF}$ gene product, and correspond to GENBANK® Accession Nos. NM_058195 and NP_478102, respectively. Bases 38-559 make up the open reading from of NM_0581995 presented in SEQ ID NO: 3.

SEQ ID NOs: 5 and 6 are nucleic acid and amino acid sequences, respectively, of a mouse p16$^{INK4a}$ gene product, and correspond to GENBANK® Accession Nos. AF044336 and AAC08963, respectively. Bases 82-588 make up the open reading frame of AF044336 presented in SEQ ID NO: 5.

SEQ ID NOs: 7 and 8 are nucleic acid and amino acid sequences, respectively, of a mouse ARF gene product, and correspond to GENBANK® Accession Nos. NM_009877 and NP_034007, respectively.

SEQ ID NOs: 9 and 10 are nucleic acid and amino acid sequences, respectively, of a rat p16$^{INK4a}$ gene product, and correspond to GENBANK® Accession Nos. L81167 and AAD48924, respectively. Bases 47-526 make up the open reading frame of L81167 presented in SEQ ID NO: 9.

SEQ ID NOs: 11 and 12 are nucleic acid and amino acid sequences, respectively, of a rat ARF gene product, and correspond to GENBANK® Accession Nos. AF474975 and AAL76337, respectively. Bases 24-506 make up the open reading frame of AF474975 presented in SEQ ID NO: 11.

SEQ ID NOs: 13 and 14 are the nucleotide sequences of a forward and reverse primer, respectively, that were used in quantitative RT-PCR assays of mouse p16$^{INK4a}$. SEQ ID NO: 15 is the nucleotide sequence of a probe that can be used to detect the product of the RT-PCR reaction using the forward and reverse primers of SEQ ID NOs: 13 and 14.

SEQ ID NOs: 16 and 17 are the nucleotide sequences of alternative forward and reverse primers, respectively, that were used in quantitative RT-PCR assays of mouse p16$^{INK4a}$. SEQ ID NO: 18 is the nucleotide sequence of a probe that can be used to detect the product of the RT-PCR reaction using the forward and reverse primers of SEQ ID NOs: 16 and 17.

SEQ ID NOs: 19 and 20 are the nucleotide sequences of a forward and reverse primer, respectively, that were used in quantitative RT-PCR assays of mouse ARF. SEQ ID NO: 21 is the nucleotide sequence of a probe that can be used to detect the product of the RT-PCR reaction using the forward and reverse primers of SEQ ID NOs: 19 and 20.

SEQ ID NOs: 22 and 23 are the nucleotide sequences of a forward and reverse primer, respectively, that were used in quantitative RT-PCR assays of mouse ARF. SEQ ID NO: 24 is the nucleotide sequence of a probe that can be used to detect the product of the RT-PCR reaction using the forward and reverse primers of SEQ ID NOs: 22 and 23.

SEQ ID NOs: 25 and 26 are the nucleotide sequences of a forward and reverse primer, respectively, that were used in quantitative RT-PCR assays of mouse Bmi-1. SEQ ID NO: 27 is the nucleotide sequence of a probe that can be used to detect the product of the RT-PCR reaction using the forward and reverse primers of SEQ ID NOs: 25 and 26.

SEQ ID NOs: 28 and 29 are the nucleotide sequences of a forward and reverse primer, respectively, that were used in quantitative RT-PCR assays of rat p16$^{INK4a}$. SEQ ID NO: 30 is the nucleotide sequence of a probe that can be used to detect the product of the RT-PCR reaction using the forward and reverse primers of SEQ ID NOs: 28 and 29.

SEQ ID NOs: 31 and 32 are the nucleotide sequences of a forward and reverse primer, respectively, that were used in quantitative RT-PCR assays of rat ARF. SEQ ID NO: 33 is the nucleotide sequence of a probe that can be used to detect the product of the RT-PCR reaction using the forward and reverse primers of SEQ ID NOs: 31 and 32.

SEQ ID NOs: 34 and 35 are the nucleotide sequences of alternative forward and reverse primers, respectively, that were used in quantitative RT-PCR assays of human p16$^{INK4a}$. SEQ ID NO: 36 is the nucleotide sequence of a probe that can be used to detect the product of the RT-PCR reaction using the forward and reverse primers of SEQ ID NOs: 34 and 35.

SEQ ID NOs: 37 and 38 are the nucleotide sequences of a forward and reverse primer, respectively, that were used in quantitative RT-PCR assays of human ARF. SEQ ID NO: 39 is the nucleotide sequence of a probe that can be used to detect the product of the RT-PCR reaction using the forward and reverse primers of SEQ ID NOs: 37 and 38.

DETAILED DESCRIPTION

The presently disclosed subject matter provides methods for determining the molecular age of a tissue in a subject. The determination of molecular age can be utilized for aiding decision making related to various medical interventions, including, but not limited to facilitating the forecasting of disease progression (e.g., in premorbid syndromes such as renal insufficiency and cardiomyopathy); providing a surrogate marker for efficacy of anti-aging therapeutics; predicting therapy-induced toxicity (e.g., from noxious therapies such as chemo- or radiotherapy and surgery that require tissue regeneration and repair); and determining donor suitability for bone marrow, solid organ, and tissue allografts donations.

In some embodiments of the presently disclosed subject matter, combinations of three pairs of primers can be employed: one pair that interrogates p16$^{INK4a}$ only, one pair that interrogate ARF only, and one pair that interrogates both p16$^{INK4a}$ and ARF simultaneously. Optionally, each primer pair is also coupled to an internal fluorescently labeled hybridization probe.

I. Definitions

For convenience, certain terms employed in the specification, examples, and appended claims are collected here. While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, the articles "a", "an", and "the" are used herein to refer to one or to more than one (i.e., to at least one) of the grammatical object of the article. By way of example, "a cell" refers to one cell or more than one cell.

As used herein, the term "about", when referring to a value or to an amount of mass, weight, time, volume, concentration, or percentage is meant to encompass variations of in some embodiments ±20% or ±10%, in some embodiments ±5%, in some embodiments ±1%, in some embodiments ±0.5%, and in some embodiments ±0.1% from the specified amount, as such variations are appropriate to practice the presently disclosed subject matter. Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "gene" refers to a nucleic acid that encodes an RNA, for example, nucleic acid sequences including, but not limited to, structural genes encoding a polypeptide. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation from one or more existing sequences.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA synthesis, processing, and transport, as well as polypeptide synthesis, transport, and post-translational modification of polypeptides. Additionally, processes that affect protein-protein interactions within the cell can also affect gene expression as defined herein.

In some embodiments, the phrase "gene expression" refers to a subset of these processes. As such, "gene expression" refers in some embodiments to transcription of a gene in a cell type or tissue. Thus, the phrase "expression level" can refer to a steady state level of an RNA molecule in a cell, the RNA molecule being a transcription product of a gene. Expression levels can be expressed in whatever terms are convenient, and include, but are not limited to absolute and relative measures. For example, an expression level can be expressed as the number of transcripts per cell. Alternatively or in addition, an expression level in a first cell can be stated as a relative amount versus a second cell (e.g., a fold enhancement or fold reduction), wherein the first cell and the second cell are the same cell type from different subjects, different cell types in the same subject, or the same cell type in the same subject but assayed at different times (e.g., before and after a given treatment, at different chronological time points, etc.).

As disclosed herein, the expression level of the $p16^{INK4a}$ gene and/or the expression level of the ARF gene can be used to determine the molecular age of the cell, tissue, organ, or component cells thereof, expressing the gene(s). As used herein, the phrases "molecular age" and "physiologic age" are used interchangeably to refer to a proximity of the cell, tissue, organ, or component cells thereof, to replicative senescence. In some embodiments, the phrases "molecular age" and "physiologic age" are used interchangeably to refer to a proximity of the cell, tissue, organ, or component cells thereof, to replicative senescence in an in vivo setting. Thus, a cell that expresses higher levels of the $p16^{INK4a}$ gene and/or the expression level of the ARF gene is closer to replicative senescence than another cell of the same cell type from the same subject or from other subjects of the same species. As such, the determination of the expression level of the $p16^{INK4a}$ gene and/or the expression level of the ARF gene can be used to provide an estimate of the capacity of the cell to divide further. Disclosed herein are applications for which an estimate of the remaining capacity of a cell to divide can be relevant.

As used herein, the term "modulate" refers to an increase, decrease, or other alteration of any, or all, chemical and biological activities or properties of a biochemical entity, e.g., a wild-type or mutant nucleic acid molecule. For example, the term "modulate" can refer to a change in the expression level of a gene or a level of an RNA molecule or equivalent RNA molecules encoding one or more proteins or protein subunits; or to an activity of one or more proteins or protein subunits that is upregulated or downregulated, such that expression, level, or activity is greater than or less than that observed in the absence of the modulator. For example, the term "modulate" can mean "inhibit" or "suppress", but the use of the word "modulate" is not limited to this definition.

As used herein, the terms "inhibit", "suppress", "downregulate", and grammatical variants thereof are used interchangeably and refer to an activity whereby gene expression or a level of an RNA encoding one or more gene products is reduced below that observed in the absence of a modulator. In some embodiments, inhibition results in a decrease in the steady state expression level of an RNA molecule. In some embodiments, inhibition results in an expression level of a target gene that is below that level observed in the absence of a modulator. In some embodiments, inhibition of gene expression is associated with an enhanced rate of degradation of the mRNA encoded by the gene (for example, by siRNA-mediated inhibition of gene expression).

The term "modulation" as used herein refers to both upregulation (i.e., activation or stimulation) and downregulation (i.e., inhibition or suppression) of a response. Thus, the term "modulation", when used in reference to a functional property or biological activity or process (e.g., enzyme activity or receptor binding), refers to the capacity to upregulate (e.g., activate or stimulate), downregulate (e.g., inhibit or suppress), or otherwise change a quality of such property, activity, or process. In certain instances, such regulation can be contingent on the occurrence of a specific event, such as activation of a signal transduction pathway, and/or can be manifest only in particular cell types.

The term "modulator" refers to a polypeptide, nucleic acid, macromolecule, complex, molecule, small molecule, compound, species, or the like (naturally occurring or non-naturally occurring), or an extract made from biological materials such as bacteria, plants, fungi, or animal cells or tissues, that can be capable of causing modulation. Modulators can be evaluated for potential activity as inhibitors or activators (directly or indirectly) of a functional property, biological activity or process, or a combination thereof (e.g., agonist, partial antagonist, partial agonist, inverse agonist, antagonist, antimicrobial agents, inhibitors of microbial infection or proliferation, and the like), by inclusion in assays. In such assays, many modulators can be screened at one time. The activity of a modulator can be known, unknown, or partially known.

Modulators can be either selective or non-selective. As used herein, the term "selective" when used in the context of a modulator (e.g. an inhibitor) refers to a measurable or otherwise biologically relevant difference in the way the modulator interacts with one molecule (e.g. a target RNA of interest) versus another similar but not identical molecule (e.g. an RNA derived from a member of the same gene family as the target RNA of interest).

It must be understood that for a modulator to be considered a selective modulator, the nature of its interaction with a target need entirely exclude its interaction with other molecules related to the target (e.g. transcripts from family members other than the target itself). Stated another way, the term selective modulator is not intended to be limited to those molecules that only bind to mRNA transcripts from a gene of interest and not to those of related family members. The term is also intended to include modulators that can interact with transcripts from genes of interest and from related family members, but for which it is possible to design conditions under which the differential interactions with the targets versus the family members has a biologically relevant outcome. Such conditions can include, but are not limited to differences in the degree of sequence identity between the modulator and the family members, and the use of the modulator in a specific tissue or cell type that expresses some but not all family members. Under the latter set of conditions, a modulator might be considered selective to a given target in a given tissue if it interacts with that target to cause a biologically relevant effect despite the fact that in another tissue that expresses additional family members the modulator and the target would not interact to cause a biological effect at all because the modulator would be "soaked out" of the tissue by the presence of other family members.

When a selective modulator is identified, the modulator binds to one molecule (for example an mRNA transcript of a gene of interest or a polypeptide derived therefrom) in a manner that is different (for example, stronger) from the way it binds to another molecule (for example, an mRNA transcript of a gene related to the gene of interest). As used herein, the modulator is said to display "selective binding" or "preferential binding" to the molecule to which it binds more strongly as compared to some other possible molecule to which the modulator might bind.

As used herein, the terms "nucleic acid" and "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., α-enantiomeric forms of naturally occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids", which comprise naturally occurring or modified nucleic acid bases attached to a polyamide backbone. Nucleic acids can be either single stranded or double stranded.

The term "operatively linked", when describing the relationship between two nucleic acid regions, refers to a juxtaposition wherein the regions are in a relationship permitting them to function in their intended manner. For example, a control sequence "operatively linked" to a coding sequence can be ligated in such a way that expression of the coding sequence is achieved under conditions compatible with the control sequences, such as when the appropriate molecules (e.g., inducers and polymerases) are bound to the control or regulatory sequence(s). Thus, in some embodiments, the phrase "operatively linked" refers to a promoter connected to a coding sequence in such a way that the transcription of that coding sequence is controlled and regulated by that promoter. Techniques for operatively linking a promoter to a coding sequence are well known in the art; the precise orientation and location relative to a coding sequence of interest is dependent, inter alia, upon the specific nature of the promoter.

Thus, the term "operatively linked" can refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operatively linked. Techniques for operatively linking a promoter region to a nucleotide sequence are known in the art.

The term "operatively linked" can also refer to a transcription termination sequence that is connected to a nucleotide sequence in such a way that termination of transcription of that nucleotide sequence is controlled by that transcription termination sequence.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide", and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. Further, fragments can include a sub-fragment of a specific region, which sub-fragment retains a function of the region from which it is derived.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. In one example, a p-value less than or equal to 0.05, in some embodiments less than 0.01, in some embodiments less than 0.005, and in some embodiments less than 0.001, are regarded as significant.

II. Genes and Gene Analysis

The presently disclosed methods take advantage of the observation disclosed herein that the expression of the $p16^{INK4a}$ and ARF genes increases as cells age. As used herein, the term "$p16^{INK4a}$" refers to a gene (when italicized) or a gene product (when in normal typeface) of the p16 tumor suppressor. This gene is alternatively referred to as the Cdkn2a gene or the INK4a gene. The human gene corresponds to GENBANK® Accession No. AF115544. Other species, including several mammalian species, have a homolog of $p16^{INK4a}$, the nucleotide and amino acid sequences of several of which are also present in the GENBANK® database.

The $p16^{INK4a}$ gene is located in the INK4a/ARF locus (also referred to as the Cdkn2a locus or the Cdkn2a/ARF locus), which maps to human chromosome 9p21. Another gene, referred to herein alternatively as ARF or $p19^{ARF}$, also maps to this locus and encodes a second tumor suppressor. It is the product of an Alternative Reading Frame of the INK4a/ARF locus. The human gene corresponds to GENBANK® Accession No. P42771. Whereas the murine and rat polypeptides are estimated to have a molecular weight of 19 kilodaltons (kDa), the human polypeptide is estimated to have a molecular weight of 14 kDa. Thus, the human polypeptide is sometimes referred to as $p14^{ARF}$. Nonetheless, the product of the Alternative Reading Frame of the INK4a/ARF locus is referred to herein as ARF or $p19^{ARF}$, or in the case of a protein, ARF or $p19^{ARF}$, even when the product is a human product.

As disclosed herein, $p16^{INK4a}$ and ARF are principal mediators of cellular senescence. To study the links between senescence and aging in vivo, Ink4a/ARF expression in rodent models of aging was examined. Disclosed herein is the discovery that expression of $p16^{INK4a}$ and ARF markedly increases in almost all rodent tissues with advancing age, while little or no change in the expression of other related cell cycle inhibitors was observed. The increase in expression is restricted to well-defined compartments within each organ studied such as the pancreatic islet, hematopoietic and neural stem cells, certain endothelia, thymic epithelium, certain classes of lymphocytes, and anterior pituitary. The increase with aging occurs in both epithelial and stromal cells of diverse lineages. The age-associated increase in expression of $p16^{INK4a}$ and ARF is attenuated in the kidney, ovary, and heart by caloric restriction, and this decrease correlates with diminished expression of an in vivo marker of senescence, as well as decreased pathology of those organs. Additionally, while it is not desired to be bound by a particular theory of operation, it appears the age-related increase in Ink4a/ARF expression can be attributed at least in part to the expression of Ets-1, a known $p16^{INK4a}$ transcriptional activator, as well as unknown Ink4a/ARF co-regulatory molecules. These data suggest that expression of the Ink4a/ARF tumor suppressor locus is a robust biomarker, and further an effector, of mammalian aging.

The expression of the $p16^{INK4a}$ and of the ARF genes also increase when cells are exposed to environmental and/or artificial insults, as these agents can lead to premature aging of cells and tissues. Such insults include various natural and non-natural mutagens including, but not limited to ultraviolet radiation, airborne mutagens, and chemical mutagens. Other exemplary insults include, but are not limited to chemotherapeutic agents and therapeutic radiation.

II.A. Biological Samples

The presently claimed subject matter provides methods that can be used to detect the expression level of a gene in a biological sample. The term "biological sample" as used herein refers to a sample that comprises a biomolecule that permits the expression level of a gene to be determined. Representative biomolecules include, but are not limited to total RNA, mRNA, and polypeptides. As such, a biological sample can comprise a cell or a group of cells. Any cell or group of cells (e.g., a tissue or tissue fragment) can be used with the methods of the presently claimed subject matter. Also encompassed within the phrase "biological sample" are biomolecules that are derived from a cell or group of cells that permit gene expression levels to be determined, e.g. nucleic acids and polypeptides.

The expression level of the gene can be determined using molecular biology techniques that are well known in the art. For example, if the expression level is to be determined by analyzing RNA isolated from the biological sample, techniques for determining the expression level include, but are not limited to Northern blotting, quantitative PCR (e.g., real time quantitative PCR and/or real time quantitative RT-PCR), and the use of nucleic acid arrays and microarrays. In some embodiments, expression levels are determined by real time quantitative PCR employing specific PCR primers for the $p16^{INK4a}$, ARF, or both the $p16^{INK4a}$ and the ARF genes.

Alternatively, gene expression can be determined by analyzing protein levels in a biological sample using antibodies. Representative antibody-based techniques include, but are not limited to immunoprecipitation, Western blotting, and the use of immunoaffinity columns.

The term "subject" as used herein refers to any vertebrate species. The methods of the presently claimed subject matter are particularly useful in the diagnosis of warm-blooded vertebrates. Thus, the presently claimed subject matter concerns mammals. More particularly contemplated is the diagnosis of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the diagnosis of autoimmune disease in livestock, including, but not limited to domesticated swine (pigs and hogs), ruminants, horses, poultry, and the like.

II.B. Nucleic Acid Isolation

Methods for nucleic acid isolation can comprise simultaneous isolation of total nucleic acid, or separate and/or sequential isolation of individual nucleic acid types (e.g., genomic DNA, cDNA, organelle DNA, genomic RNA, mRNA, polyA$^+$ RNA, rRNA, tRNA) followed by optional combination of multiple nucleic acid types into a single sample.

When total RNA or purified mRNA is selected as a biological sample, the disclosed method enables an assessment of a level of gene expression. For example, detecting a level of gene expression in a biological sample can comprise determination of the abundance of a given mRNA species in the biological sample.

Nucleic acids that are used for subsequent amplification and labeling can be analytically pure as determined by spectrophotometric measurements or by visual inspection following electrophoretic resolution. The nucleic acid sample can be free of contaminants such as polysaccharides, proteins, and inhibitors of enzyme reactions. When an RNA sample is intended for use as probe, it can be free of nuclease contamination. Contaminants and inhibitors can be removed or substantially reduced using resins for DNA extraction (e.g., CHELEX™ 100 from BioRad Laboratories, Hercules, Calif., United States of America) or by standard phenol extraction and ethanol precipitation. Isolated nucleic acids can optionally be fragmented by restriction enzyme digestion or shearing prior to amplification.

II.C. PCR Amplification of Nucleic Acids

The terms "template nucleic acid" and "target nucleic acid" as used herein each refers to nucleic acids isolated from a biological sample as described herein above. The terms "template nucleic acid pool", "template pool", "target nucleic acid pool", and "target pool" each refers to an amplified sample of "template nucleic acid". Thus, a target pool comprises amplicons generated by performing an amplification reaction using primer pairs specific for the template nucleic acid.

The term "target-specific primer" refers to a primer that hybridizes selectively and predictably to a target sequence, for example a target sequence present in an RNA transcript derived from a $p16^{INK4a}$ gene or a ARF gene. A target-specific primer can be selected or synthesized to be complementary to known nucleotide sequences of target nucleic acids.

The term "primer" as used herein refers to a contiguous sequence comprising in some embodiments about 6 or more nucleotides, in some embodiments about 10-20 nucleotides (e.g. 15-mer), and in some embodiments about 20-30 nucleotides (e.g. a 22-mer). Primers used to perform the method of the presently disclosed subject matter encompass oligonucleotides of sufficient length and appropriate sequence so as to provide initiation of polymerization on a nucleic acid molecule.

II.D. Quantitative PCR

In some embodiments of the presently disclosed subject matter, the abundance of specific mRNA species present in a biological sample (for example, mRNA extracted from a cell or tissue of interest) is assessed by quantitative PCR. Standard molecular biological techniques are used in conjunction with specific PCR primers to quantitatively amplify those mRNA molecules corresponding to the genes of interest. Methods for designing specific PCR primers and for performing quantitative amplification of nucleic acids including mRNA are well known in the art. See e.g., Heid et al., 1996; Sambrook & Russell, 2001; Joyce, 2002; Vandesompele et al., 2002.

In some embodiments, a technique for determining expression level includes the use of the TAQMAN® Real-time Quantitative PCR System (Applied Biosystems, Foster City, Calif., United States of America). Specific primers for genes of interest (e.g., $p16^{INK4a}$ and ARF) are employed for determining expression levels of these genes. In some embodiments, the expression level of one or more housekeeping genes (e.g., 18S rRNA) are also determined in order to normalize a determined expression level.

The products of the Quantitative PCR employed in the TAQMAN® Real-time Quantitative PCR System can be detected using a probe oligonucleotide that hybridizes to the PCR product. Typically, this probe oligonucleotide is labeled at the 5' and/or 3' ends with one or more detectable labels. In some embodiments, the 5' end is labeled with a fluorescent label and the 3' end is labeled with a fluorescence quencher. In some embodiments, the 5' end is labeled with tetrachloro-6-carboxyfluorescein (TET™; Applera Corp., Norwalk, Conn., United States of America) and/or 6-FAM™ (Applera Corp.) and the 3' end includes a tetramethylrhodamine (TAMRA™; Applera Corp.), NFQ, and/or MGB quencher.

Other methodologies for determining gene expression levels can also be employed, including but not limited to Amplified Antisense RNA (aaRNA) and Global RNA Amplification (Van Gelder et al., 1990; Wang et al., 2000; U.S. Pat. No. 6,066,457 to Hampson et al.). In accordance with the methods of the presently disclosed subject matter, any one of the above-mentioned PCR techniques or related techniques can be employed to perform the step of amplifying the nucleic acid sample. In addition, such methods can be optimized for amplification of a particular subset of nucleic acid (e.g., specific mRNA molecules versus total mRNA), and representative optimization criteria and related guidance can be found in the art. See Williams, 1989; Linz et al., 1990; Cha & Thilly, 1993; McPherson et al., 1995; Roux, 1995; Robertson & Walsh-Weller, 1998.

III. Applications

III.A. Determining Molecular or Physiologic Age of a Cell or Tissue

The presently disclosed subject matter provides methods for determining the molecular age of a cell or tissue in a subject. In some embodiments, the methods comprise (a) providing a sample from the cell or tissue; (b) quantifying a level of expression of $p16^{INK4a}$, ARF, or both $p16^{INK4a}$ and ARF in the sample; and (c) comparing the level of expression of $p16^{INK4a}$, ARF, or both $p16^{INK4a}$ and ARF to a standard to thereby determine a molecular age of the cell or tissue.

As disclosed herein, as cells age and approach senescence, the expression level of the $p16^{INK4a}$ and/or ARF genes increases dramatically. This increase can be quantitated and used to determine the molecular or physiologic age of cells and tissues. Typically and because different cells and tissues can increase $p16^{INK4a}$ and/or ARF expression at different rates in a subject, the molecular age of a cell or tissue need not correlate with chronological age of the subject.

To determine a molecular age of a cell or tissue, the expression of $p16^{INK4a}$ and/or ARF is quantified and compared to a standard. Various standards can be employed, including, but not limited to a quantification of a level of expression of $p16^{INK4a}$, ARF, or both $p16^{INK4a}$ and ARF in the cell or tissue in a population of same species individuals as the subject; a quantification of a level of expression of $p16^{INK4a}$, ARF, or both $p16^{INK4a}$ and ARF in the cell or tissue in the subject at an earlier time; and/or a quantification of a level of expression of $p16^{INK4a}$, ARF, or both $p16^{INK4a}$ and ARF in a second sample isolated from at least one different tissue of the subject.

Thus, the level of expression of $p16^{INK4a}$, ARF, or both $p16^{INK4a}$ and ARF in a cell of tissue of a subject is compared to a level of expression of $p16^{INK4a}$, ARF, or both $p16^{INK4a}$ and ARF in a population, in the same cell or tissue of the subject at a different time point (e.g., before versus after undergoing a particular therapy), or ir a different cell or tissue of the subject at the same time point. As a result, the molecular age of the cell or tissue can be determined to be "older" or "younger" than a particular reference standard (for example, when the second or third of the above referenced standards are employed), or can be placed along a continuum (for example, when expression data in the same cell type or tissue from a large population of non-related individuals of the same species is employed). In the latter case, the molecular age can be expressed as a percentile, quartile, etc., of the population in order to provide a relative measure of molecular age of the cell or tissue in the subject.

III.B. Predicting Disease Progression

In some embodiments, the presently disclosed subject matter provides a method for predicting a predisposition to disease progression in a cell or tissue in a subject. In some embodiments, the methods comprise (a) providing a sample from the cell or tissue; (b) quantifying a level of expression of $p16^{INK4a}$, ARF, or both $p16^{INK4a}$ and ARF; and (c) comparing the level of expression of $p16^{INK4a}$, ARF, or both $p16^{INK4a}$ and ARF to a standard to thereby predict a predisposition to disease progression in the cell or tissue in the subject.

Certain medical conditions are associated with a gain and/or a loss of the ability of a given cell type to undergo replicative division. One example are the islets of the pancreas in diabetes. Another particular example of the former is the progression from a pre-neoplastic state to a neoplastic state in some types of cancer. The methods disclosed herein can be used to predict and/or determine when a subject's premorbid disease is progressing to a more aggressive disease by quantifying a level of expression of $p16^{INK4a}$, ARF, or both $p16^{INK4a}$ and ARF in the relevant cell type of the subject and comparing it to, for example, disease free, healthy age-matched controls. Additional premorbid diseases that can be monitored for disease progression include, but are not limited renal insufficiency, HIV-associated illness (e.g., progression to a low $CD4^+$ T-cell count), atherosclerosis, bone-marrow failure syndromes (e.g., myelodysplasia), congenital defects of DNA repair, and cardiomyopathy.

Alternatively or in addition, a level of expression of $p16^{INK4a}$, ARF, or both $p16^{INK4a}$ and ARF in the relevant cell type of the subject can be tracked over time to indicate whether the cell type is approaching replicative senescence, maintaining its current state, or, in the case where the level of expression of $p16^{INK4a}$, ARF, or both $p16^{INK4a}$ and ARF in the relevant cell type goes down, losing its normal control over replication and division.

In any of these cases, a change (or a lack of change) in an expression level of $p16^{INK4a}$, ARF, or both $p16^{INK4a}$ and ARF can provide the physician with information related to the state of the disease and the effectiveness of therapeutics, if any, being used to treat the disease.

III.C. Predicting Future Toxicity of Treatments

The presently disclosed subject matter also provides methods for predicting a tendency to therapy-induced toxicity in a cell or tissue in a subject. In some embodiments, the method comprises (a) providing a sample from the cell or tissue; (b) quantifying a level of expression of $p16^{INK4a}$, ARF, or both $p16^{INK4a}$ and ARF in the sample; and (c) comparing the level of expression quantified with a standard to thereby predict a tendency to therapy-induced toxicity in the cell or tissue in the subject.

As is known in the medical art, certain treatments, including but not limited to chemotherapy and radiotherapy, can be toxic to normal cells in the subject receiving the treatment. For example, chemotherapy and radiotherapy are known to negatively affect certain blood cell lineages such as red blood cells, platelets, and granulocytes. In order for the subject to survive these treatments and gain a benefit therefrom, it is necessary for these blood cell types to be replenished after the treatment is completed. While certain therapeutics can assist in reconstituting the blood cell compartment (e.g., erythropoietin and granulocyte colony stimulating factor), these therapeutics rely on stem cells and other blood cell precursors present in the bone marrow and elsewhere to achieve this reconstitution.

The therapy itself, however, as well as other conditions present in the patient, can damage these and other cells necessary for the recovery of the patient. This damage can include, for example, environmental and genetic insults like those disclosed herein that upregulate or otherwise result in accumulation of $p16^{INK4a}$ and ARF in the relevant stem cell/precursor pool. As disclosed herein, the accumulation of $p16^{INK4a}$ and ARF in cells restricts the capacity of these cells to divide. When the capacity of cells that are necessary to replenish the blood cell compartment is compromised, the ability of the subject to withstand further treatments and/or future treatments is similarly compromised.

Thus, determining the molecular age of precursor/stem cell populations in a subject can give the physician information relevant to the assessment of whether a specific patient would be more likely to develop toxicity associated with the contemplated treatment. This information could then be used to evaluate whether such treatment is advisable, and/or whether additional supportive treatments should be considered.

III.D. Determining Donor Suitability

The presently disclosed subject matter also provides methods for determining suitability of a subject for a cell or tissue donation. In some embodiments, the method comprises (a) providing a sample from the cell or tissue; (b) quantifying a level of expression of $p16^{INK4a}$, ARF, or both $p16^{INK4a}$ and ARF in the sample; and (c) comparing the level of expression quantified with a standard to thereby determine suitability of a subject for donating the cell or tissue. In some embodiments, the cell or tissue donation is appropriate for a transplant selected from the group consisting of bone marrow transplant, solid organ transplant, and tissue graft transplant.

In order to effectively transplant a subject (e.g., a recipient or the donor himself or herself when the donor is also the recipient), the transplanted tissue must successfully engraft the recipient. In some embodiments, the ability to engraft a recipient can correlate with the replicative potential of the graft. Thus, the molecular age of the cells that comprise the graft can be relevant to the decision making associated with the transplant.

Information concerning the molecular age of the cells that comprise the graft can be relevant to likelihood of success of the transplant far several reasons. First, in the case where certain cells of the graft must have a high capacity to divide (e.g., a bone marrow transplant), the molecular age with correlate with the replicative capacity of the tissue. Bone marrow cells with a relatively lower molecular age would thus be expected to have a higher replicative capacity, and would thus be expected to serve as a better graft than cells with a higher molecular age and associated more restricted replicative capacity.

In some embodiments, the tissue to be donated is a solid organ. For example, the method could be employed to determine the optimal donor for a patient with multiple potential living-related donors. The organ to be donated (e.g., a kidney) could be tested in potential donors to determine the most physiologically young organ for donation. Alternatively, physiologic age could be determined on organs harvested from donors in a persistent vegetative state. The organs of interest would be biopsied and tested prior to transplantation to determine donor suitability.

In some embodiments, the tissue to be donated is intended for use as a tissue graft. Typically, the tissue and/or cells isolated from the tissue are grown for some time in vitro in order to produce the final graft to be introduced into the recipient. Given that tissues and/or cells with a lower molecular age would have a greater replicative capacity than tissues and/or cells with a higher molecular age, knowledge of the molecular age of such tissues and/or cells can inform the physician as to appropriate donors for such tissues and/or cells. For example, in those cases where multiple potential donors are available, the physician can include the molecular ages of the various donors in the decision making concerning which donor to select.

III.E. Kits

Also provided herein are kits for carrying out any of the methods disclosed herein. The kits can comprise suitable buffers, containers, and/or other materials, reagents, sets of instructions, etc. for carrying out the methods. Additionally, primers as disclosed herein can be include in the kits, primer pairs specific for a $p16^{INK4a}$ gene or a ARF gene or sequence shared by both $p16^{INK4a}$ and ARF genes.

In some embodiments the primer pair comprises at least nucleotide sequences as set forth in at least two of SEQ ID NOs: 13-18 or SEQ ID NOs: 22-27. In some embodiments the primer pair is specific for a human $p16^{INK4a}$ gene or a human ARF gene. In some embodiments the kit comprises at least two primer pairs, and wherein at least one primer pair is specific for the $p16^{INK4a}$ gene and at least one primer pair is specific for the ARF gene.

In some embodiments the primer pair comprises a first primer and a second primer, and the first primer, the second primer, or both the first and second primer comprise a detectable label. In some embodiments the detectable label is a fluorescent label.

In some embodiments the kit comprises a primer pair specific for a control gene. Optionally, the control gene is selected from the group including but not limited to an 18S rRNA gene, a glucose-6-phosphate dehydrogenase gene, a phosphoglycerate kinase 1 gene, a β-actin gene, an elongation factor-1 gene, an elongation factor-2 gene, and a beta-2-microglobulin gene.

In some embodiments the kit comprises a probe for detecting a polymerase chain reaction product produced using the primer pair.

III.F. Determining Effectiveness of Anti-aging Therapeutics

The presently disclosed subject matter also provides methods for screening a presumptive anti-aging compound for an effect on a physiologic age of a cell. In some embodiments, the method comprises (a) providing the presumptive anti-aging compound to the cell; and (b) comparing expression of $p16^{INK4a}$, ARF, or both $p16^{INK4a}$ and ARF in the cell before and after the providing step, wherein the providing modulates the expression of $p16^{INK4a}$, ARF, or both $p16^{INK4a}$ and ARF in the cell.

In some embodiments, the cell is present in an animal and the presumptive anti-aging compound is provided to the animal. In some embodiments, the presumptive anti-aging compound is provided to the animal systemically or locally to the cell. In such embodiments, a relevant target cell population is identified in the animal, and a baseline level of expression of $p16^{INK4a}$, ARF, or both $p16^{INK4a}$ and ARF is determined prior to administering the presumptive anti-aging compound to the animal. Standard techniques can be employed for administering test compounds to animals and the techniques disclosed herein can be used for assessing changes in the molecular age of the target cell population resulting from the administration. When these changes are compared to changes seen in appropriate controls (e.g., age-matched animals of the same species that do not receive the presumptive anti-aging compound), the effectiveness of the compound as an anti-aging treatment can be assessed.

Alternatively or in addition, the cell is an in vitro cultured cell. For example, murine embryonic fibroblasts (MEFs) accumulate $p16^{INK4a}$ and ARF in culture. Presumptive anti-aging compounds can be administered to MEFs in vitro, and the effects of such compounds on $p16^{INK4a}$ and ARF expression can be determined. Compounds that inhibit or decrease the rate of accumulation of $p16^{INK4a}$ and/or ARF can then be tested in animals to determine whether they have anti-aging activity in vivo.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for Examples 1-3

Animals. All animals were housed and treated in accordance with protocols approved by the institutional care and use committee for animal research at the University of North Carolina at Chapel Hill. All murine analyses were performed in C57BL/6 mice unless otherwise mentioned. For cell sorting experiments, 22- to 25-month-old mice of mixed genetic background (C57BL/6×NIH Black Swiss; from Yue Xiong, University of North Carolina, Chapel Hill, N.C., United States of America) were analyzed. Old (21 months) and young (5 months) GHR KO and WT (CR and AL) mice of mixed genetic background (derived from Ola-BALB/c, C57BL/6, and C3H; courtesy of John Kopchick, Ohio University, Athens, Ohio, United States of America) were analyzed. CR for this murine cohort was done as described in Miller et al., 2002. Aged rodents were obtained from the aged-rodent colonies of the National Institute on Aging (see Turturro et al., 1999; see also the "Scientific Resources" section of the website of the National Institute on Aging of the National Institutes of Health) and euthanized, and organs were harvested as described below. For murine studies, old (25-26 months) and young (2.5-3.5 months) C57BL/6 mice (3 males and 3 females) were analyzed. For CR experiments, old (28 months) and young (3 months) F344 AL rats (2 old and 2 young males, 2 old and 2 young females) were obtained, as well as old (28 months) CR littermates (2 males and 2 females).

Animals were euthanized by $CO_2$ inhalation, and organs were harvested. Organs were grossly dissected free of contaminating tissue (e.g., adipose) and then snap-frozen. RNA was harvested from a matched portion of the organ (e.g., the superior half of the kidney) in all instances to assure that results did not differ because of organ composition. For RNA analysis, tissues were collected after cardiac perfusion with RNALATER® (Ambion Inc., Austin, Tex., United States of America) or after snap-freezing in liquid nitrogen. For IHC and H&E staining, organs were harvested and fixed as described below, and then stored in 70% ethanol until paraffin embedding.

Quantitative real-time PCR. Total RNA was extracted from tissues, serially passaged murine embryo fibroblasts (each passage corresponding to 3 days in vitro), or sorted cell samples using a QIAGEN RNEASY® RNA isolation kit according to the manufacturer's (Qiagen Inc., Valencia, Calif., United States of America) instructions. Transcription into cDNA was done in a 20 µl volume using oligo-$dT_{(12-18)}$ or random hexamer and IMPROM-II™ reverse transcriptase (Promega Corp., Madison, Wis., United States of America) according to the manufacturer's instructions. All PCR reactions were carried out in a final volume of 20 µl and were performed in duplicate for each cDNA sample in the ABI PRISM® 7700 Sequence Detection System (Applied Biosystems, Foster City, Calif., United States of America) according to the manufacturer's protocol. All experiments were done on organs from at least 2 different animals in each group (old vs. young, CR vs. AL).

Sequence-specific primers and probe were designed using PRIMER EXPRESS® software (Applied Biosystems) for the indicated genes (Table 1). Oligonucleotide primers and probes were synthesized by MWG-BIOTECH Inc. of High Point, N.C., United States of America. All primer sets were designed to span an intron. Pre-developed assays were purchased from Applied Biosystems for the additionally listed murine and rat genes (Table 1). The reaction mix consisted of Universal Master Mix, No AMPERASE® UNG (Applied Biosystems), 0.25 µM fluorogenic probe, 0.9 µM of each specific forward and reverse primer, and 9 µl of diluted cDNA (equivalent to ~90 ng total RNA). Amplifications were done under standard conditions.

The number of PCR cycles needed to reach the fluorescence threshold was determined in duplicate for each cDNA, averaged, and then normalized to at least 1 reference gene (18S RNA, GAPDH, and/or TATA-binding protein (TBP) to yield the cycle number at which fluorescence threshold was reached (Ct). The ratio of expression in old versus young tissues (old/young) was determined as 2-[Ct(old)−Ct(young)]; therefore, $\log_2$(old/young)=Ct(old)−Ct(young). Ratios were log-transformed for calculations of SE and Pearson correlation coefficients using Prism software (GraphPad Software Inc., San Diego, Calif., United States of America). For absolute quantification of transcript copy number for $p16^{INK4a}$, $p15^{INK4b}$, ARF, $p21^{CIP}$, $p18^{INK4c}$, and $p19^{INK4d}$, the fragment of interest was cloned and a standard curve generated with serial 4-fold dilutions. For all assays tested, the PCR reaction was linear over the range studied (19-40 cycles of amplification). If Ct was not reached by 40 cycles, expression was considered below the limit of detection. All RT-PCR reactions gave a single band when analyzed by gel electrophoresis, and all reactions used a fluorochrome-labeled internal probe to enhance sensitivity and specificity.

TABLE 1

List of Primers and Probes Employed for TAQMAN® Real-time Quantitative PCR

| Gene | Forward Primer | Reverse Primer | Probe Sequence[1] | Ref. Sequence[2] |
|---|---|---|---|---|
| Mouse | | | | |
| $p16^{INK4a}$ | CCCAACGCCCCGAACT (SEQ ID NO: 13) or | GCAGAAGAGCTGCTACGTGAA (SEQ ID NO: 14) or | TTCGGTCGTACCCCGATTCAGGTG (SEQ ID NO: 15) or | AF044336 |
| | CGGTCGTACCCCGATTCAG (SEQ ID NO: 16) | GCACCGTAGTTGAGCAGAAGAG (SEQ ID NO: 17) | AACGTTGCCCATCATCA (SEQ ID NO: 18) | |
| ARF | TGAGGCTAGAGAGGATCTTGAGA (SEQ ID NO: 19) or | GCAGAAGAGCTGCTACGTGAA (SEQ ID NO: 20) or | CCGCACCGGAATCCTGGAC (SEQ ID NO: 21) or | NM_009877 |
| | TGAGGCTAGAGAGGATCTTGAGAAG (SEQ ID NO: 22) | GTGAACGTTGCCCATCATCATC (SEQ ID NO: 23) | ACCTGGTCCAGGATTC (SEQ ID NO: 24) | |
| Bmi-1 | AGAAGAGATTTTTATGCAGCTCA (SEQ ID NO: 25) | CAACTTCTCCTCGGTCTTCA (SEQ ID NO: 26) | AGCTGATGCTGCCAATGGCTCCA (SEQ ID NO: 27) | NM_007552 |
| | ABI Assay ID[3] | | | |
| $p15^{INK4b}$ | Mm00483241_m1 | | | NM_007670 |
| $p18^{INK4c}$ | Mm00483243_m1 | | | NM_007671 |
| $p19^{INK4d}$ | Mm00486943_m1 | | | NM_009878 |
| $p21^{CIP}$ | Mm00432448_m1 | | | NM_007669 |
| $p27^{KIP}$ | Mm00438167_g1 | | | NM_009875 |
| Ets-1 | Mm00468970_m1 | | | NM_011808 |
| TBP | Mm00446973_m1 | | | NM_013684 |
| 18S rRNA | 4333760F | | | X03205 |
| GAPDH | Mm99999915_g1 | | | NM_008084 |
| Rat | | | | |
| $p16^{INK4a}$ | ACCAAACGCCCCGAACA (SEQ ID NO: 28) | GAGAGCTGCCACTTTGACGT (SEQ ID NO: 29) | TCGGTCGTACCCCGATACAGGTGA (SEQ ID NO: 30) | L81167 |
| ARF | GAGGGCCGCAGCCACAT (SEQ ID NO: 31) | CACCATAGGAGAGCAGGAGAGCT (SEQ ID NO: 32) | CGTTGCCCATCATCATCACCTGGT (SEQ ID NO: 33) | AF474975 |
| | ABI assay ID[3] | | | |
| $p21^{CIP}$ | Rn00589996_m1 | | | NM_080782 |
| Ets-1 | Rn00561167_m1 | | | NM_012555 |
| Id1 | Rn00562985_s1 | | | NM_012797 |
| 18S rRNA | 4333760F | | | X03205 |
| Human | | | | |
| $p16^{INK4a}$ | CCAACGCACCGAATAGTTAGC (SEQ ID NO: 34) | GCGCTGCCCATCATCATG (SEQ ID NO: 35) | CCTGGATCGGCCTCCGAC (SEQ ID NO: 36) | AF115544 |

TABLE 1-continued

List of Primers and Probes Employed for TAQMAN ®
Real-time Quantitative PCR

| Gene | Forward Primer | Reverse Primer | Probe Sequence[1] | Ref. Sequence[2] |
|---|---|---|---|---|
| ARF | CTGAGGAGCCAGCGTC TAG (SEQ ID NO: 37) | CCCATCATCATGACCTGGTC TTCTA (SEQ ID NO: 38) | CAGCAGCCGCTTCC (SEQ ID NO: 39) | NM_058195 |

[1]Probes can be labeled at the 5' end with a dye (e.g., TET ™ and/or 6-FAM ™) and at the 3' end with a fluorescence quencher (e.g., TAMRA ™, MGB, and/or NFQ)
[2]Accession No. in the GENBANK ® database
[3]Assay ID No. from the Applied Biosystems TAQMAN ® Gene Expression Array (Mouse or Rat, as appropriate). It should be noted, however, that primers can also be designed as desired from the sequence information found in the corresponding GENBANK ® Accession No.

Cell sorting of bone marrow, lymph node, thymus, and spleen. Tissues from 5- and 22-month old mice (n=2 per age) were disaggregated and sorted. For bone marrow, lineage-negative and lineage-positive fractions were collected using a lineage cell depletion kit with an AUTOMACS™ Separator (Miltenyi Biotec Inc., Auburn, Calif., United States of America) according to the manufacturer's protocol. Stromal and cell components for lymph node, thymus, and spleen were prepared by pressing between frosted glass slides, followed by washing with PBS containing 10% FCS. Splenocytes were then further analyzed after red blood cell lysis by staining with anti-B220 (CALTAG™ Laboratories Inc., Burlingame, Calif., United States of America) and anti-CD11b (Mac1; Caltag Laboratories Inc.) mAbs for 30 minutes on ice followed by washing. Cells were sorted by MOFLO® (Dako-Cytomation California Inc., Carpinteria, Calif., United States of America) to B220$^+$, Mac1$^+$, and B220$^-$Mac1$^-$ populations (purity >94%) at the University of North Carolina FACS Core facility.

IHC and SA-β-gal staining. To determine optimal IHC staining conditions for p16$^{INK4a}$, tissues were harvested from age-matched littermate p16$^{INK4a+/+}$ and p16$^{INK4a-/-}$ mice and analyzed. After empiric testing of several fixatives as described in Mikaelian et al. (2004) Toxicol Pathol 32:181-191, Fekete's acid alcohol solution (61% ETOH, 4.3% glacial acetic acid, and 3.5% formalin) was determined to be optimal for p16$^{INK4a}$ IHC staining in mouse and rat tissues using a commercially available antibody and kit (IMMU-NOCRUZ™ HRP kit with F-12 antibody, sc-1661; Santa Cruz Biotechnology Inc., Santa Cruz, Calif., United States of America). Five-micron paraffin sections were cut and underwent steam citrate antigen retrieval, hybridization per the manufacturer's protocols, and hematoxylin counterstaining. Sections were examined by an observer blinded to animal age, diet, and genotype. SA-β-gal staining was performed as described in Dimri et al., 1995; Jacobs et al., 1999; and Melk et al., 2003. Briefly, thin sections (<2 mm) of harvested organs were fixed at room temperature for 15 minutes in 0.5% glutaraldehyde/PBS (pH 6.0). After fixation, organ slices were washed twice in PBS (pH 6.0), stained overnight at 37° C. in SA-β-gal buffer (1 mg/ml X-gal, 5 mM potassium ferricyanide, 5 mM potassium ferrocyanide, and 1 mM MgCl2 in PBS, pH 6.0), and photographed with a high-resolution CCD camera (LighTools Research, Encinitas, Calif., United States of America).

Example 1

Expression of Ink4a/ARF In Vivo

The expression of cyclin-dependent kinase inhibitor (CDKI) family members, which are principal regulators of the mammalian cell cycle, was determined. CDKIs inhibit the kinase activity of Cdk2, Cdk4, and Cdk6, thereby inhibiting phosphorylation of their target protein Rb and eliciting G1 arrest. Eighteen quantitative real-time PCR strategies (see Table 1) were used to assay CDKI expression in tissues from old and young syngeneic adult rodents (see FIGS. 1A and 1B). The expression of ARF, a cell cycle inhibitor through its regulation of p53 stability was studied, because ARF is coregulated with p16$^{INK4a}$ (see FIGS. 1A and 1B). A marked increase (3-fold or greater) in the expression of p16$^{INK4a}$ was seen in 26 of 27 organs analyzed from 15 murine and 12 rat tissues. Particularly large (>30-fold) increases in relative terms of the ratio of RNA expression in old versus young tissues (old/young ratio) were seen in the murine cecum, kidney, ovary, and uterus (FIG. 1A; $\log_2$ scale), while the highest expression in absolute terms was seen in lung, lymph node, adrenal, and uterus from aged animals (FIG. 1B; $\log_{10}$ scale). The geometric mean of the old/young ratios among the 15 murine tissues analyzed was 9.7 (i.e., the average tissue demonstrated an approximately 10-fold increase in the expression of p16$^{INK4a}$ with aging). This value is likely an underestimate of the true average fold increase, because in tissues such as the pancreas and bone marrow (FIG. 1A), p16$^{INK4a}$ expression was below the level of detection in young animals. Therefore, in these tissues, only a minimum estimate of the fold increase in expression in these tissues could be determined.

Similarly, ARF expression increased several fold in most of the tissues examined, particularly heart, duodenum, kidney, and uterus (see FIGS. 1A and 1B). The geometric mean of the ARF old/young ratios was a 3.5-fold increase, while the next highest cell cycle inhibitor, p21$^{CIP}$, demonstrated only a 1.4-fold average increase. These data do not exclude a specific role for another CDKI in a particular tissue; for example, p15$^{INK4b}$ showed an approximately 5-fold increase in expression in the heart with aging. Likewise, the disclosed data do not exclude the possibility that certain of the CDKIs (e.g., p18$^{INK4c}$ or p27$^{KIP}$ are regulated predominantly in a posttranscriptional manner with aging. Nonetheless, Ink4a/ARF upregulation appears to be a strong correlate to organismal aging across many tissue types, and this marked and widespread upregulation is unique among the major in vivo inhibitors of the mammalian cell cycle.

In terms of absolute transcript number and protein expression, the expression of p16$^{INK4a}$ and ARF was considerably lower in tissues from aged mice than in primary cultures of murine embryo fibroblasts (FIG. 1E), even at passage 4 (less than 14 days in vitro). This observation emphasizes that the act of culture itself potently induces the Ink4a/ARF locus but also suggests that in vivo Ink4a/ARF expression increases only in a relatively small subset of cells within a given tissue (e.g., the β cells of the pancreas; see FIG. 2A). To determine in which organ compartments the expression of Ink4a/ARF increased, additional lines of analysis were performed including immunohistochemistry (IHC) and mRNA quantification in purified populations of sorted cells (see FIGS. 2A and 2B; additional data not shown). Using these approaches, the compartmental expression of p16INK4a and/or ARF in selected tissues from aging rodents was determined (summarized in Table 1).

Discussion of Example 1

The presently disclosed observations led to several conclusions. First, there was a good correlation in most tissues between mRNA expression and protein expression. An exception, however, was the lung, where RNA expression of p16$^{INK4a}$ even from young mice was higher in absolute terms than in several tissues from old mice (FIG. 1B) yet protein expression was not detected by IHC or immunoprecipitation-western analysis (the latter data not shown). This result could be attributable to either translational regulation of p16$^{INK4a}$ or decreased protein stability in this tissue. Furthermore, p16$^{INK4a}$ expression was detected in a variety of cell types, including lining epithelium (e.g., of the renal cortex), mesenchyme (of the uterus), lymphocytes (in the spleen and lymph nodes), and specialized endocrine secretory tissues (e.g., pancreatic islet and adrenal; see FIGS. 2A and 2B, and Table 1). For example, in the uterus, there was marked expression of p16$^{INK4a}$ in the stroma of aged mice, but less so by IHC in the uterine epithelium. In the kidney, a marked increase in expression was noted in the cortical tubules, with detectable, but significantly less, expression in the medulla and glomeruli. In the spleen, increased expression of p16$^{INK4a}$ in both the stromal (red pulp) and lymphocyte (white pulp) compartments was noted, although this was higher in stroma (see FIGS. 2A and 2B). In aggregate, these data suggest that the expression of p16$^{INK4a}$ mRNA and protein increases in cells of varied histogenetic origins with aging. These results indicate that expression of the Ink4a/ARF locus can be induced in many if not most cell types in vivo, as well as by the locus's role in the suppression of a wide variety of cancer types (see e.g., Ruas & Peters (1998) Biochim Biophys Acta 1378: F115-F177.

Figure 2:
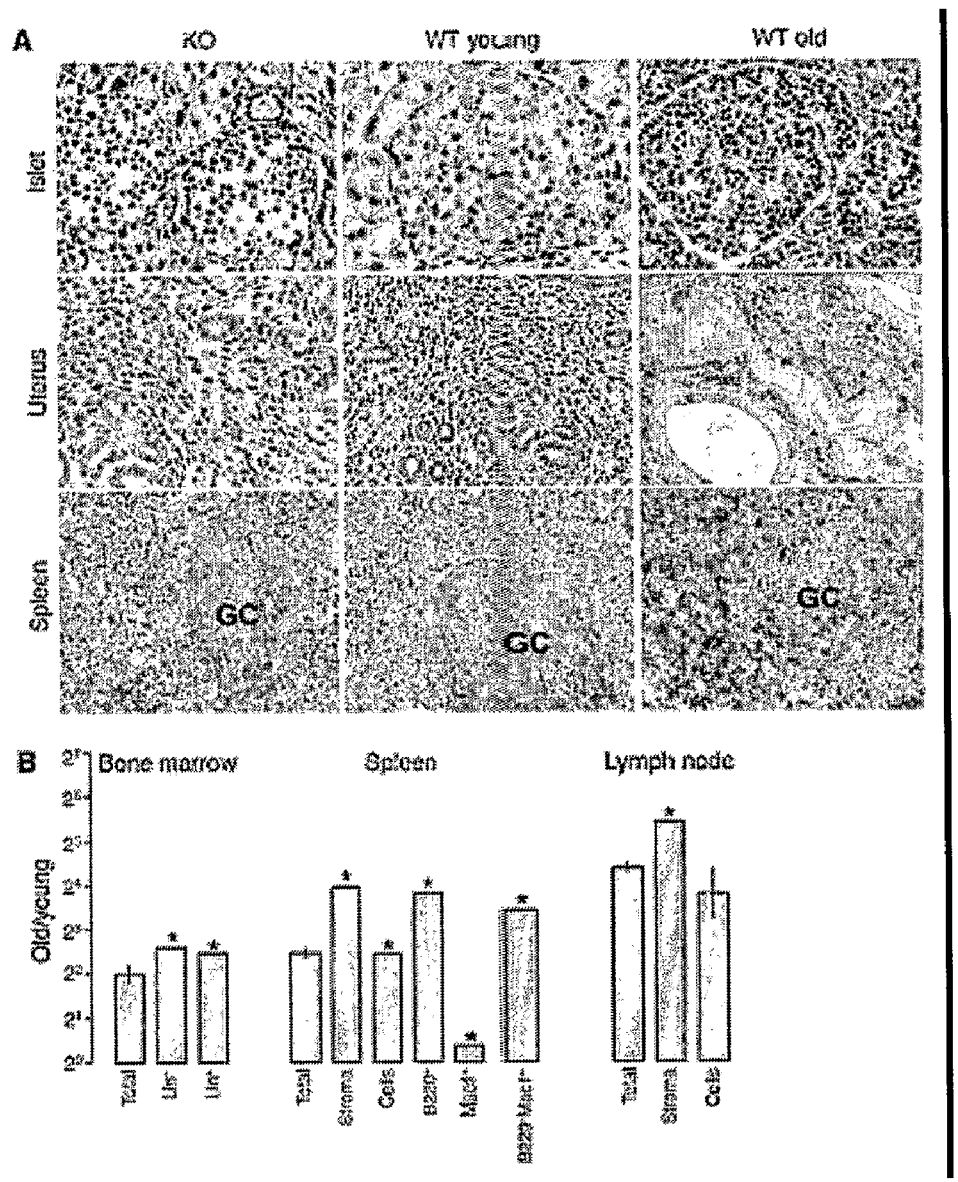
FIGS. 2A and 2B depict $p16^{INK4a}$ expression in specific compartments by immunohistochemistry and cell purification.

To permit quantification of the compartmental expression of p16$^{INK4a}$, hematopoietic organs were harvested and specific cell types purified (FIG. 2B). Expression of p16$^{INK4a}$ increased with aging in both the stromal and the cellular (predominantly T cell) compartments of lymph nodes, but to a greater degree in the stroma (42-fold vs. 13-fold). Similarly, both the stromal and the cellular compartments of the spleen showed increased expression of p16$^{INK4a}$ with aging (15-fold vs. 5-fold). Among the splenic cellular elements, the predominant increases were seen in lymphocytes (B220$^+$, 48% of total splenic cells) and cells that did not express B lymphocyte or myeloid markers (double negative for Mac1 and B220, 22% of cells), whereas little increase was seen in the myeloid compartment (Mac1$^+$, 9% of cells). Lastly, we compared the expression of p16$^{INK4a}$ and ARF in lineage-negative (2%) versus lineage-positive (98%) bone marrow cells. In this compartment, the principal increase in expression was in lineage-negative cells, which are enriched for hematopoietic stem and progenitor cells (HSPCs). This finding is consistent with the reported role of Ink4a/ARF expression in HSPCs and early committed progenitors from adult mice (Park et al. (2003) Nature 423:302-305). Therefore, Ink4a can be expressed in several cell types of hematopoietic organs, including stromal elements, lymphocytes, and progenitor cells.

Example 2

Caloric Restriction Retards p16INK4a Accumulation

Figure 3:
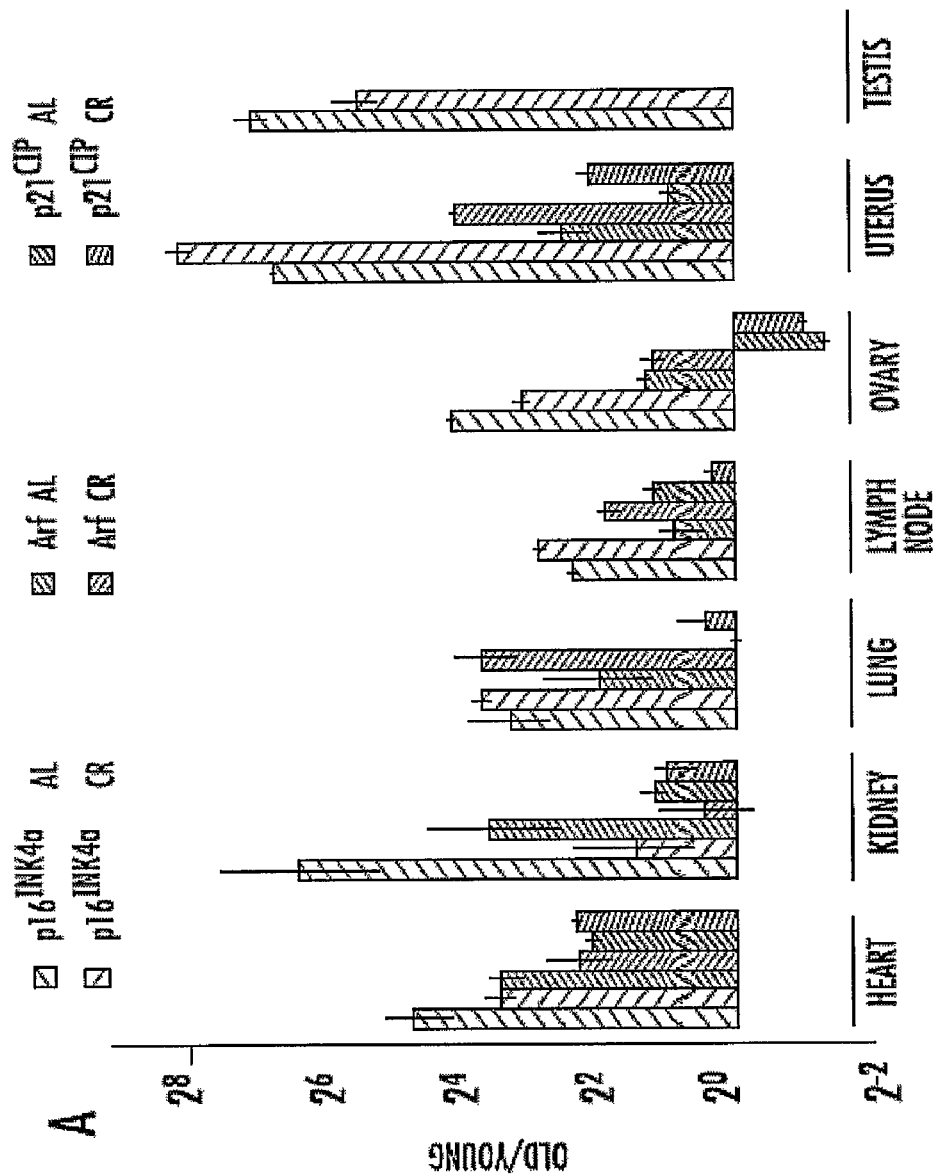
FIGS. 3A-3D depict the effects of caloric restriction and GHR deficiency on gene expression and aging.
Figure 3:
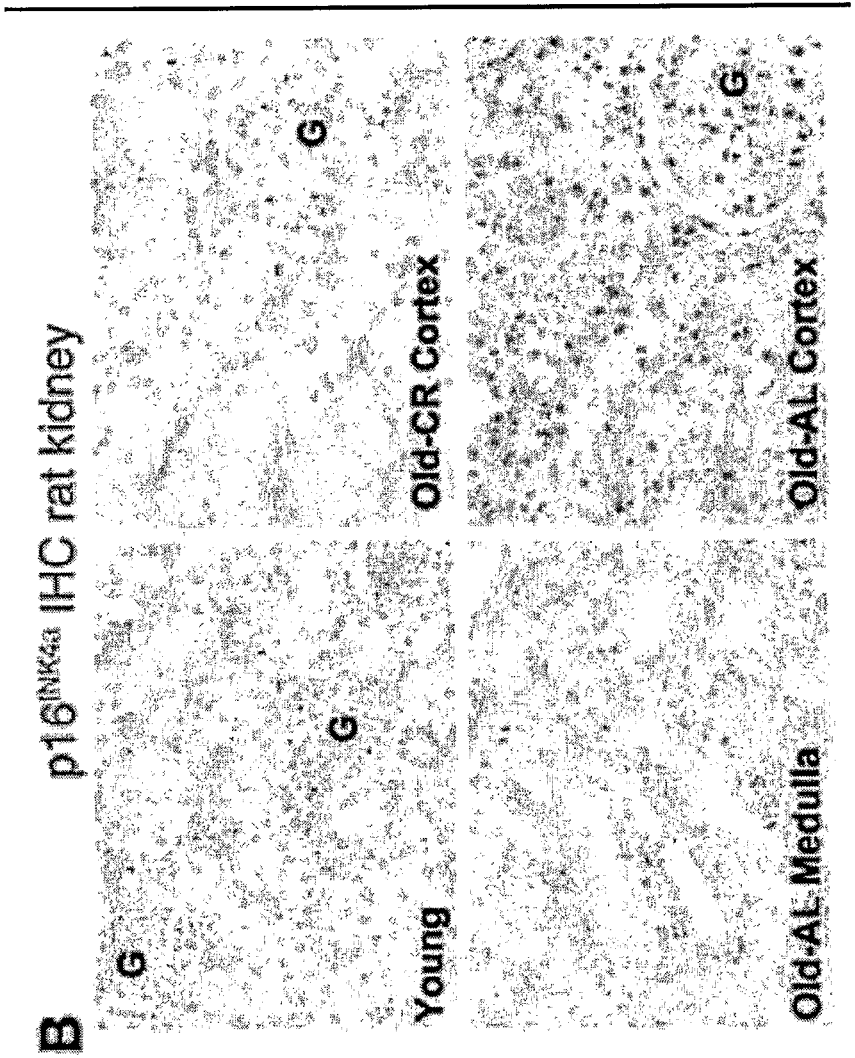
Figure 3:
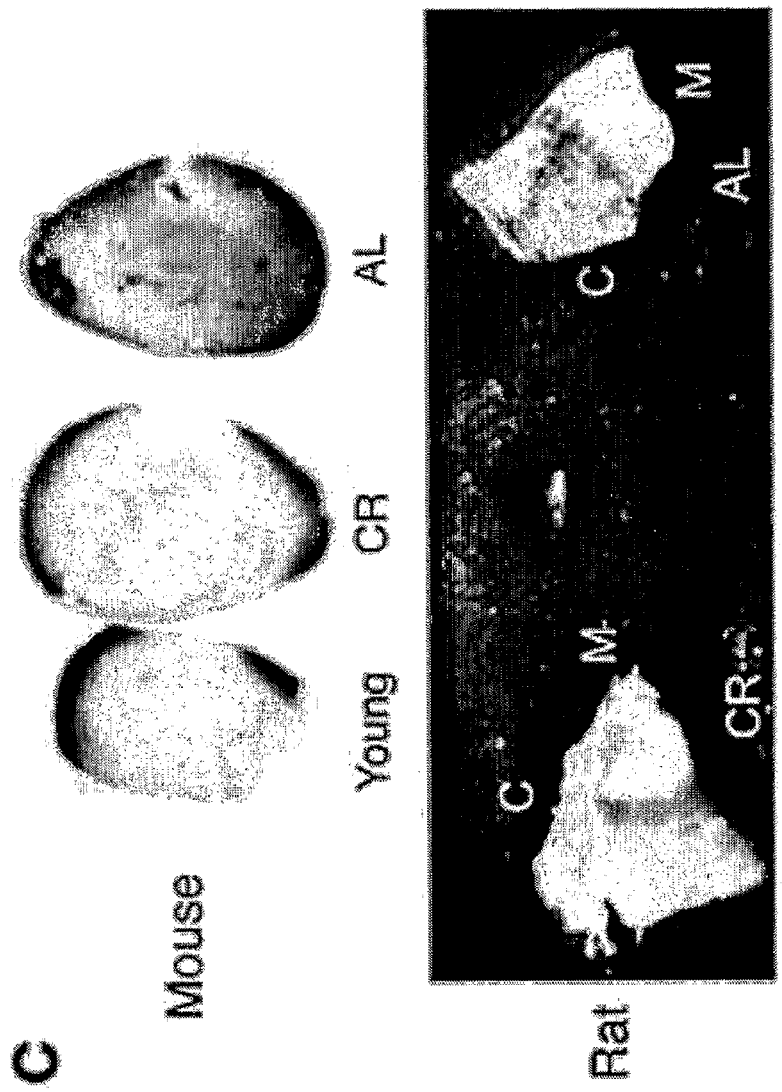
Figure 3:
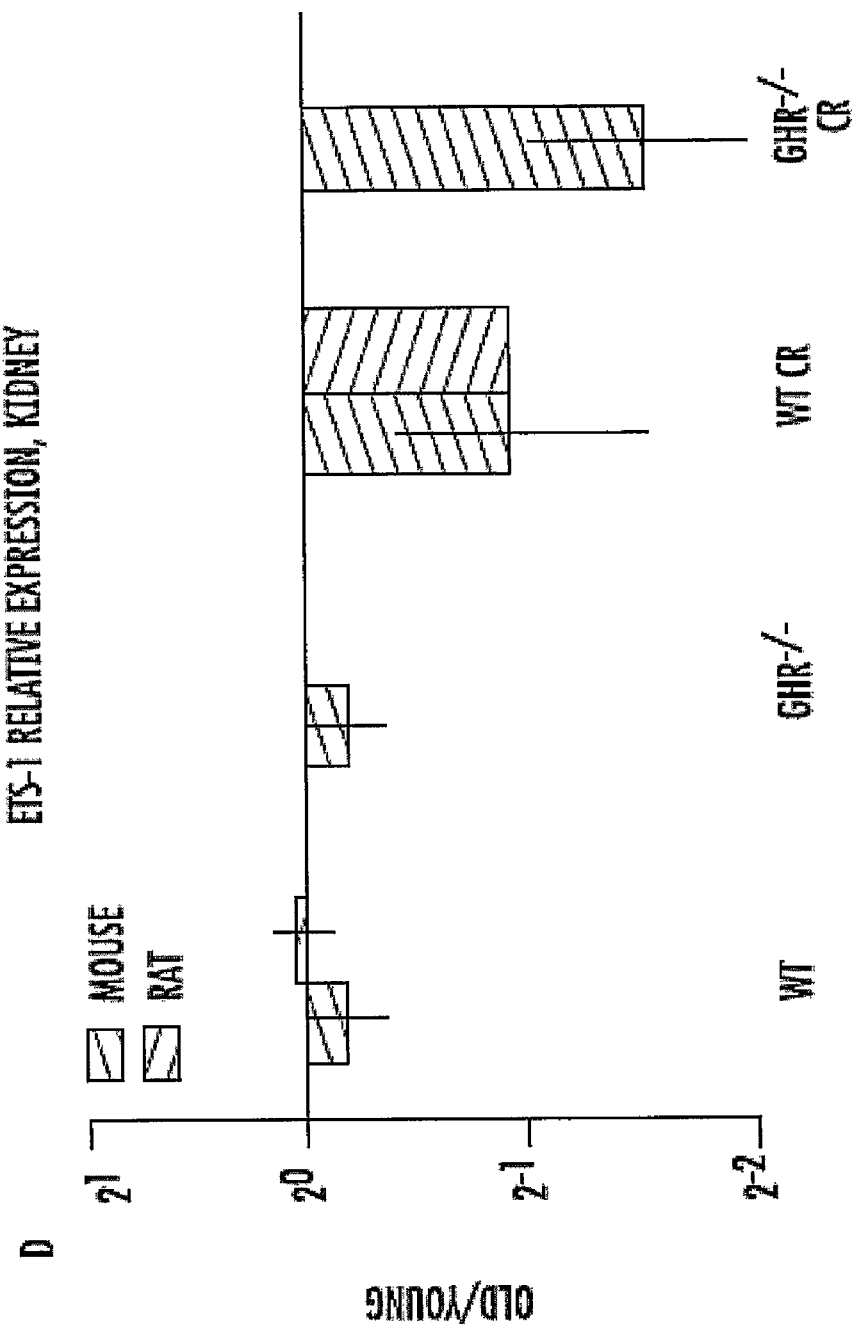

Caloric restriction (CR) retards aging in many species, but the molecular effectors of this are unknown. To examine the effects of CR on p16$^{INK4a}$ expression, total RNA was harvested from organs from calorically restricted (CR) and ad libitum-fed (AL) Fischer 344 (F344) rats. Ink4a/ARF expression increased with aging in 12 different tissues from AL rats (representative data shown in FIG. 3A). There was excellent concordance in the fold increase of Ink4a/ARF and p21$^{CIP}$ expression between mouse and rat tissues from AL animals, except in the testis. In murine testis, no increase in p16$^{INK4a}$ was seen (see FIGS. 1A and 1B), whereas in rat testis, a greater than 135-fold increase in p16$^{INK4a}$ expression was noted (FIG. 3A). A histologic examination of rat testis from old AL males, however, demonstrated marked involvement with Leydig cell tumor, which occurs spontaneously in the majority of AL F344 rats greater than 24 months of age, and which highly expresses p16$^{INK4a}$. Increases in ARF expression similar in magnitude to those in the mouse were also noted across this panel of tissues, as were more modest increases in P21$^{CIP}$ (FIG. 3A). Therefore, mice and rats appear to age similarly with respect to Ink4a/ARF expression.

When compared with tissues from AL animals, several, but not all, tissues from CR animals showed marked reductions in the age-induced increase of Ink4a/ARF expression. A 2- to 16-fold attenuation in the age-induced expression of p16$^{INK4a}$ was seen in adrenal, heart, kidney, ovary, and testis; but CR did not attenuate Ink4a/ARF expression in the lung, lymph node, spleen, and liver (FIG. 3A). Unexpectedly, in the uterus, CR appeared to induce a significant increase in Ink4a/ARF expression with aging. Aged CR males demonstrated greatly reduced Leydig cell hyperplasia compared with AL animals. Correspondingly, this decreased tumor burden correlated with a marked reduction in the age-induced increase in p16$^{INK4a}$ expression (135-fold in AL rats vs. 58-fold in CR rats). Therefore, the decrease in p16$^{INK4a}$ expression with CR in aged rat testis likely results from an anti-neoplastic effect of CR. In contrast, the marked decrease in p16$^{INK4a}$ expression in the cortical tubules of the kidney (FIG. 3B) from CR animals correlated with decreased nephritis, a chronic disease seen with nearly complete penetrance in aged F344 rats and a principal limit to the longevity of this strain. Therefore, in both of these tissues, the decrease in Ink4a/ARF expression occurred in concert with a CR-induced reduction of a disease state, suggesting that increased Ink4a/ARF expression in some circumstances might predispose to organ pathology, presaging organ failure and death. These observations also predict that tissue-specific increases in Ink4a/ARF expression with aging likely will vary among mammals (and even across inbred strains of rodents) to reflect specific predispositions to disease resulting from unshared genetics and/or environmental exposures. The relationship of Ink4a/ARF expression with other aging models was also tested. Several single-gene mutations that decrease IGF-1 extend longevity, through a mechanism that appears at least partially distinct from CR.

Figure 4:
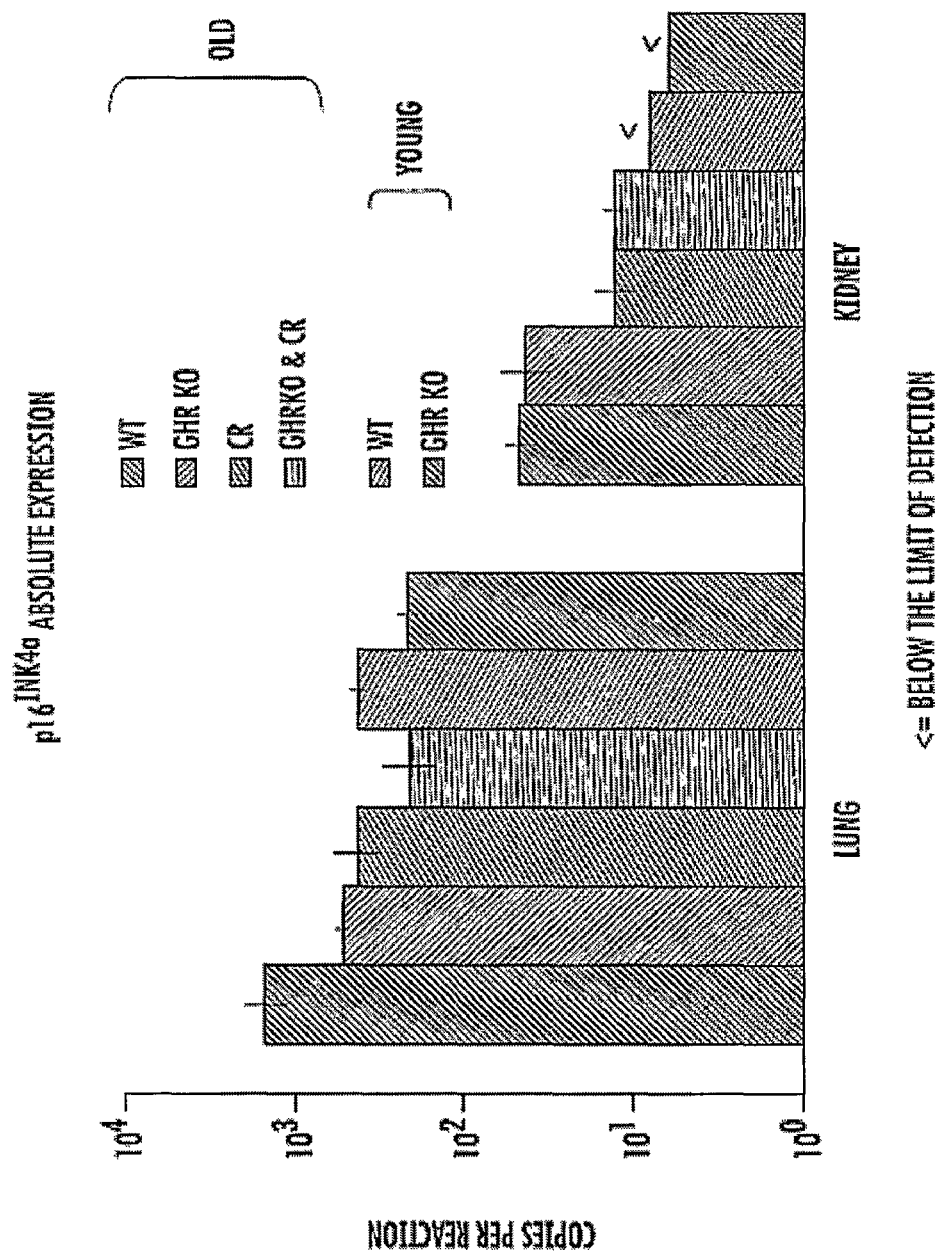
FIG. 4 depicts the effects of caloric restriction (CR) and growth hormone receptor (GHR) deficiency on $p16^{INK4a}$ expression with aging. The absolute copy number ($\log_{10}$ scale) of $p16^{INK4a}$ mRNA molecules per 90 ng total RNA RT-PCR from lung and kidney of young (5 months) and old (21 months) GHR$^{+/+}$ and GHR$^{-/-}$ mice with or without caloric restriction is presented +/−SEM. Each estimate represents the mean of 8-16 quantitative RT-PCR reactions on independent RNA samples derived from organs of 22 mice.

Ink4a/ARF expression in both lung and kidney from old and young growth hormone receptor+/+(GHR$^{+/+}$) and GHR$^{-/-}$ mice that had been fed ad libitum or CR diets was also tested. The age-induced expression of Ink4a/ARF in mice from this cohort of mixed genetic background was more heterogeneous than in either the inbred F344 rat or the C57BL/6 mouse cohort (FIG. 4). Nonetheless, in accord with observations in the rat, CR significantly reduced p16$^{INK4a}$ and ARF expression in the murine kidney (FIG. 4). GHR deficiency, however, had no effect on p16$^{INK4a}$ or ARF expression in the kidney, although modest reductions in p16$^{INK4a}$ and ARF expression were noted in the lung from GHR-deficient animals (FIG. 4). These results confirm in another species the effect of CR on Ink4a/ARF expression in the kidney and also suggest that GHR deficiency and CR enhance longevity by molecularly distinct mechanisms in distinct tissues.

Furthermore, the functional significance of Ink4a/ARF expression in aging mammals was also determined. A well-described in vivo marker of senescence, senescence-associated β-galactosidase (SA-β-gal) expression, a high-pH galactosidase activity detectable in senescent cells and tissues, was employed. This assay was limited in most tissues (e.g., liver and spleen) because of high background activity but was interpretable in both murine and rat kidney (FIG. 3C). A significant increase in SA-β-gal activity was detected in aging kidney from AL mice and rats (FIG. 3C) and was predominantly restricted to the renal cortex, a pattern of expression that overlapped with p16$^{INK4a}$ expression. This increase in SA-β-gal activity was, like the increase in p16$^{INK4a}$ expression, abolished by CR, which suggests that Ink4a/ARF-induced senescence is induced in the renal cortex as a result of increased metabolism.

Example 3

Figure 5:
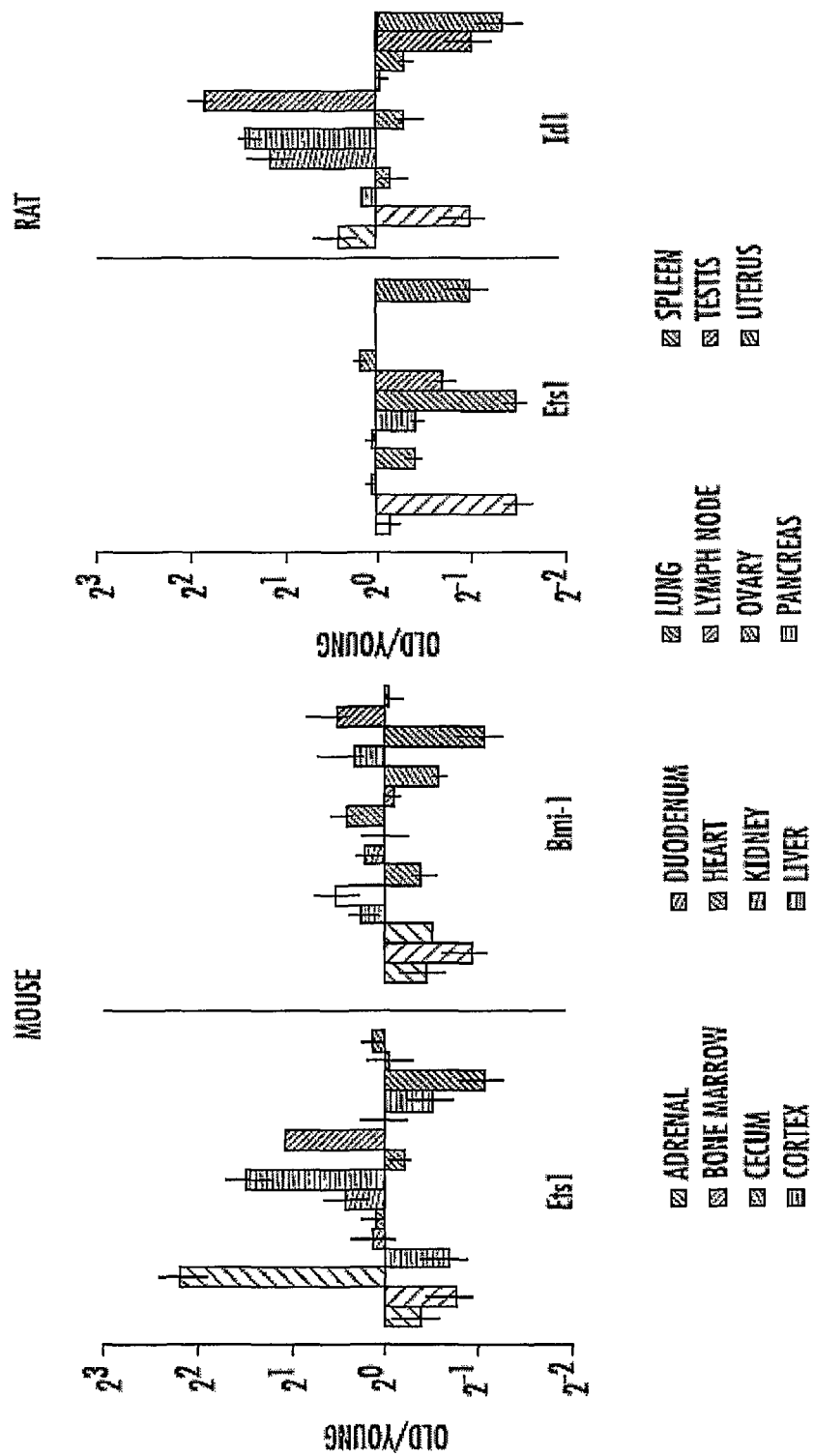
FIG. 5 depicts the expression of regulators of p16$^{INK4a}$ with aging. The left panel depicts the ratios of the expression of p16$^{INK4a}$ regulators Ets-1 and Bmi-1 in (Old (26 months)/Young (2.5 months)) mice from 15 tissues, and is presented +/−SEM. Each estimate represents the mean of 4-8 quantitative RT-PCR reactions on independent RNA samples derived from 4-6 mice. The right panel depicts the ratios of the expression of the p16$^{INK4a}$ regulators Ets-1 and Id1 from 12 tissues derived from (Old (28 months)/Young (3 months)) ad libitum fed (AL) or calorically restricted (CR) F344 rats, and is presented +/−SEM. Each estimate represents the mean of 4-8 quantitative RT-PCR reactions on independent RNA samples derived from 4 rats.

Ets-1 and a Common Ink4a/ARF Regulator Modulate p16$^{INK4a}$ Expression with Aging In an effort to determine the factors responsible for the marked accumulation of Ink4a/ARF with aging, the expression of 3 principal regulators of Ink4a/ARF expression, Ets-1, an activator of p16$^{INK4a}$; Id1, a transcriptional repressor of p16$^{INK4a}$; and Bmi-1, a repressor of the Ink4a/ARF locus; was determined (FIG. 5). The expression of these genes was determined across multiple tissues from young and old mice and/or rats, with and without CR. Pearson correlation coefficients of the log-transformed old/young ratios of all genes across the tissue types analyzed were calculated. As expected, a high correlation was found between p16$^{INK4a}$ and ARF expression (r=0.75, P<0.0001) and a modest correlation between ARF and p21$^{CIP}$ (r=0.37, P=0.03), but no significant correlation between p16$^{INK4a}$ and p21$^{CIP}$ was found. These results are consistent with the known transcriptional relationships of these genes; in particular, several proteins have been identified that coordinately regulate the expression of both Ink4a/ARF products, and ARF regulates p53 activity, which in turn induces p21$^{CIP}$ expression. Unexpectedly, a high correlation between p18$^{INK4c}$ and p19$^{INK4d}$ (r=0.68, P=0.002) was found, which suggests that these genes are regulated by common or related transcriptional elements. Although these homologous INK4s are concomitantly expressed in many tissues, the inventor is not aware of previous data showing coordinated expression in vivo.

Figure 6:
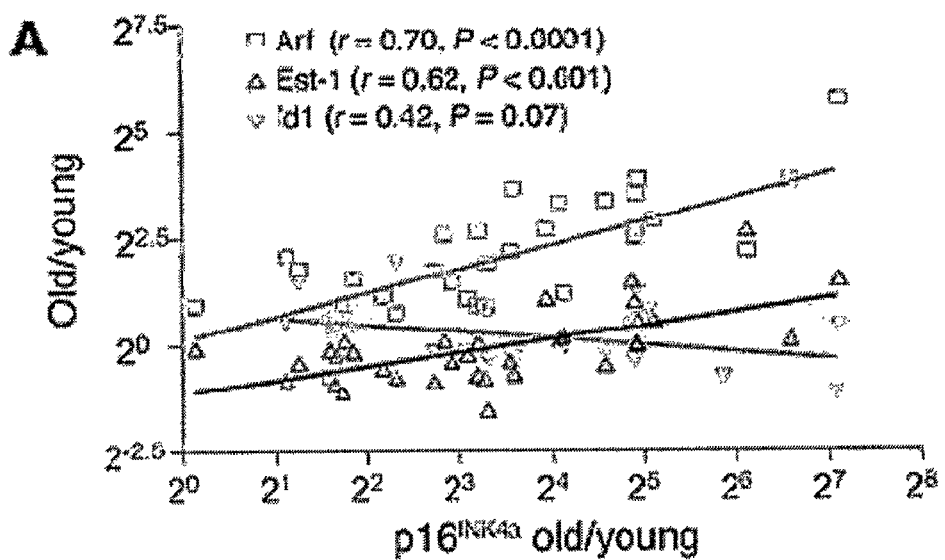
FIGS. 6A and 6B depict a strong correlation of p16$^{INK4a}$ expression increases with aging with ARF and Ets-1 expression.
Figure 6:
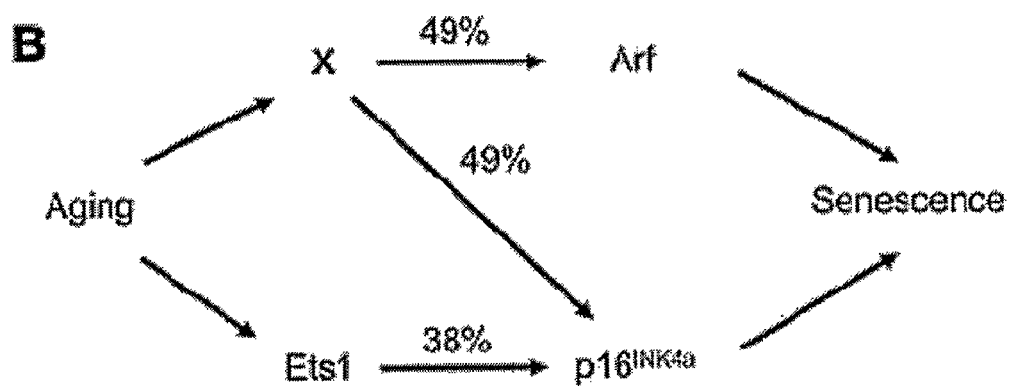

The expression of Ink4a/ARF regulators was next considered (FIG. 5). A weak negative correlation was found between the expression of Id1 and that of p16$^{INK4a}$ (r=−0.40, P=0.07), consistent with Id1's known role as a transcriptional repressor of p16$^{INK4}$. No significant correlation was seen between Bmi-1 expression and that of either p16$^{INK4a}$ or ARF. However, a strong correlation was noted between p16$^{INK4a}$ and Ets-1 (r=0.62, P<0.001; FIG. 6A), but not between ARF and Ets-1 (r=0.15, P=0.40). This observation is consistent with the finding that Ets-1 induces the expression of p16$^{INK4a}$, but not ARF, in cultured cells and suggests that a significant component of the in vivo variance in p16$^{INK4a}$ expression with aging (r$^2$=0.38) results from transcriptional activation by Ets-1 (FIG. 6B). Moreover, a reduction in Ets-1 expression was seen in the kidney of CR rats and mice (FIG. 3D), which suggests that increased metabolism is upstream of Ets-1 activation in the aging kidney. Similarly, the strong correlation between p16$^{INK4a}$ and ARF also suggests that an unknown co-regulator(s) of p16$^{INK4a}$ and ARF exerts a powerful effect (r$^2$=0.49) on the expression of both Ink4a/ARF products with aging, and that this co-regulator(s) must be independent of Ets-1 (as ARF and Ets-1 are not correlated). Therefore, the in vivo expression of p16$^{INK4a}$ in aging appears to reflect almost equally a p16$^{INK4a}$-Specific effect that correlates with Ets-1 expression, and an independent, Ink4a/ARF co-regulatory effect.

Discussion of Examples 1-3

Figure 10:
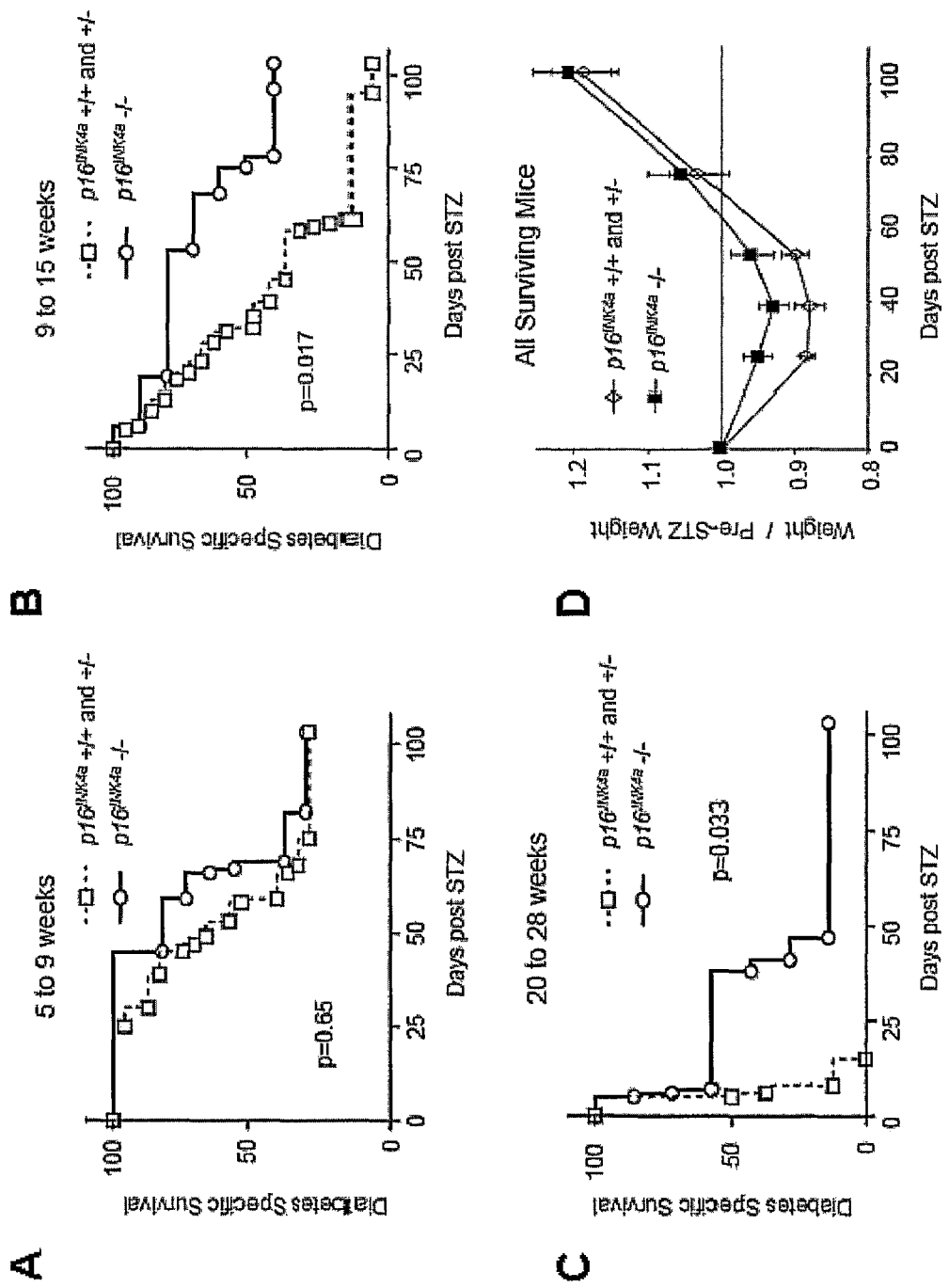
FIGS. 10a-10d show the influence of p16$^{INK4a}$ expression on STZ regeneration, an islet specific toxin. These data indicate that p16$^{INK4a}$ expression not only correlates with aging in this tissue, but plays a causal role in aging of this tissue.

In accordance with the presently disclosed subject matter it is observed that in vivo senescence, induced by Ink4a/ARF expression, plays a causal role in the aging of certain tissue types. First, as disclosed herein, Ink4a/ARF expression is not only tightly linked with aging but is influenced by CR and correlates with SA-β-gal expression. These results suggest that p16$^{INK4a}$ and/or ARF expression is not merely a biomarker, but also an effector, of aging, presumably by limiting the self-renewal capacity of disparate tissues including at least lymphoid organs, bone marrow, and brain. Additional evidence for this comes from the data in the pancreatic islet. Here, mice lacking p16$^{INK4a}$ showed decreased rate of aging in this compartment. Also, these mice demonstrated enhanced regenerative capacity of this tissue after treatment with an islet specific toxin (streptozotocin; see FIG. 10).

As disclosed herein, a significant attenuation of age-induced Ink4a/ARF expression by CR was detected in several tissues, but particularly in the kidney, where the effect was nearly complete. The reduction in Ink4a/ARF expression correlated with decreased nephritis in aged F344 rats, a major limit of longevity in this strain. Therefore, while it is not desired to be bound by a particular theory of operation, it is suggested that Ink4a/ARF expression limits the ability of aged kidney to self-repair, resulting in organ failure and death. The analysis of tissue from GHR-deficient animals disclosed herein demonstrated that GHR loss was not seen to affect p16$^{INK4a}$ expression in the aging kidney (FIG. 4). It is possible that reductions in IGF-1 similarly retard the increase in Ink4a/ARF expression in other tissues; this would explain the ability of CR to extend the longevity of IGF-1-deficient animals (Bartke et al., 2001). Alternatively, IGF-1 deficiency might work through a distinct, Ink4a/ARF-independent mechanism to retard aging. As rodents have large telomeres and promiscuously express telomerase, the signal that induces Ink4a/ARF-mediated senescence in the kidney and other organs is not likely to be telomere-based.

As disclosed herein, however, there is a strong correlation between Ets-1 expression and p16$^{INK4a}$ expression with aging across 27 different tissues from 2 species, with and without CR. Given that Ets-1 is a direct transcriptional activator of p16$^{INK4a}$ in vitro, these data suggest that Ets-1 is a principal determinant of p16$^{INK4a}$ expression with aging in vivo. Ets-1, in turn, is regulated by a variety of stress-related signals and, in particular, MAPK activity. These observations are consistent with the model (FIG. 6B) that presently unidentified stresses activate Ets-1 via MAPK pathways to induce a p16$^{INK4a}$-mediated senescence in aging organisms.

By statistical methods, the existence of an unknown co-regulatory factor(s) that is distinct from Ets-1 and that modulates the expression of both p16$^{INK4a}$ and ARF with aging was inferred. A candidate is the Polycomb group (PcG) protein Bmi-1, which has been shown to regulate p16$^{INK4a}$ and ARF expression in stem cells in vivo (Lessard & Sauvageau, 2003; Molofsky et al., 2003; Park et al., 2003; Leung et al., 2004). A negative correlation between Bmi-1 expression and either p16$^{INK4a}$ or ARF was not detected in most aging tissues. Therefore, while it is not desired to be bound by a particular theory of operation, transcription of Bmi-1 is not likely to be a predominant regulatory mechanism of Ink4a/ARF expression in vivo across multiple tissue types, but this analysis does not exclude a specific role for Bmi-1 in a particular tissue. Along these lines, greater than 2-fold decreases in Bmi-1 expression with aging was detected in spleen and bone marrow (FIG. 5), which suggests that perhaps Bmi-1-containing PcG complexes play a role in repressing Ink4a/ARF expression in hematopoietic tissues. Likewise, it is possible that related Ink4a/ARF-repressing PcG family members such as Cbx7 or Mel18 subsume the function of Bmi-1 in other tissues; that PcG complex activity is regulated post-transcriptionally; and/or that unidentified non-PcG molecules are important co-regulators of Ink4a/ARF.

A molecular biomarker of physiologic, as opposed to chronologic, age is needed in clinical medicine. While other molecular markers of aging have been suggested, the analysis of INK4a/ARF expression disclosed herein is believed to be particularly useful in this regard, for several reasons. First, the change in p16$^{INK4a}$ expression with aging is large—over 10-fold in many tissues—and relatively simple to measure by either immunohistochemical methods or quantitative real-time PCR analysis. For example, there is a clinically validated, commercially available kit (DakoCytomation Inc., Carpinteria. Calif., United States of America) for use in the detection of p16$^{INK4a}$ expression, and many anatomic pathologists are already comfortable with the interpretation of p16$^{INK4a}$ IHC. Moreover, the results presented herein demonstrate that Ink4a/ARF can be expressed in many cell types in response to age-induced stresses, and that Ink4a/ARF expression changes in at least a subcompartment of the majority of mammalian organs with aging. For this reason, p16$^{INK4a}$ and/or ARF expression can be a particularly robust marker of aging, useful for the study of many cell types in disparate organs. Lastly, given the causal role of p16$^{INK4a}$ and/or ARF in aging, expression of INK4a/ARF should be a stronger correlate of aging than expression of other genes for which expression is merely epiphenomenal.

Thus, disclosed herein are the observations that INK4a/ARF expression correlates with tissue aging and alterations in disease progression in the rodent kidney and testis, and that reduced expression of the locus correlates with response to an anti-aging therapy, caloric restriction. Therefore, the presently disclosed subject matter indicates that the measurement of INK4a/ARF expression can similarly be of clinical benefit in the determination of human physiologic age.

Example 4

INK4a/ARF Expression in Lymphocytes from Healthy Human Donors

Figure 7:
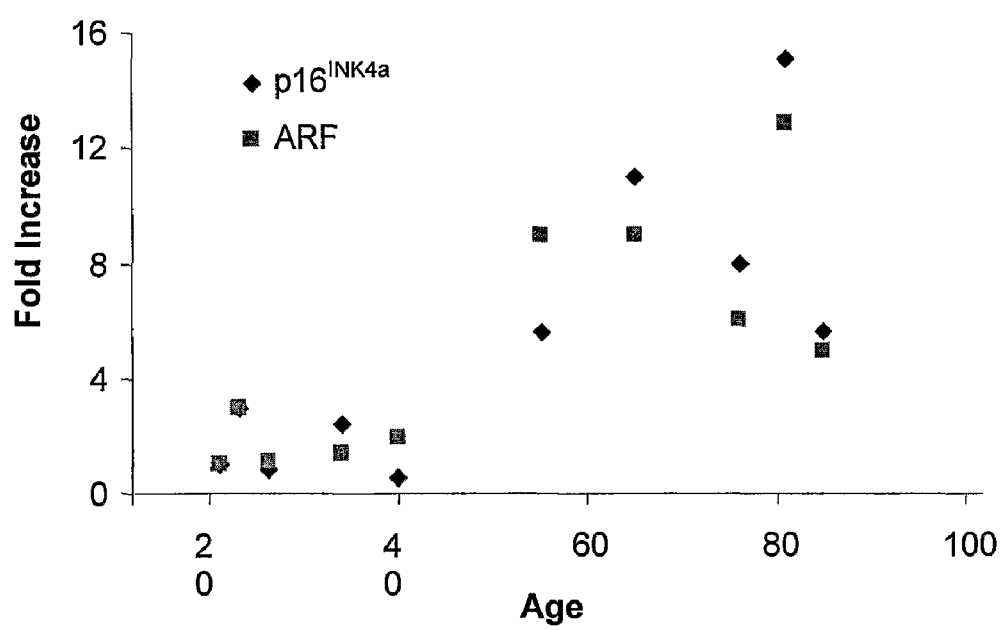
FIG. 7 is a plot showing INK4a/ARF expression vs. patient age in lymphocytes from healthy human donors. p16$^{INK4a}$ expression=diamonds; ARF expression=squares.

FIG. 7 is a plot showing INK4a/ARF expression in lymphocytes from healthy human donors, evaluated in accordance with the methods disclosed herein. p16$^{INK4a}$ expression=diamonds; ARF expression=squares. The plot shows age in years on the x-axis and fold increase in expression on the y-axis,

Example 5

INK4a/ARF Expression in Islets from Pancreas

To define the compartmental expression of p16$^{INK4a}$ within the adult pancreas, and quantitate the increase in pancreatic p16$^{INK4a}$ expression with aging, islets were separate from exocrine pancreas through gradient centrifugation. Total RNA was then harvested from purified islets and exocrine pancreas from old and young adult mice for TAQMAN® analysis (FIG. 8) as described herein.

Using this approach, significant p16$^{INK4a}$ islet expression even in young animals was observed, which increased greater than five fold with modest aging (to 15 months). Expression of p16$^{INK4a}$ was significantly enriched in purified islets with >50-fold higher expression in this compartment than in the exocrine pancreas. ARF expression closely mirrored that of p16$^{INK4a}$, with a similar degree of age-induced increase in enrichment in the endocrine pancreas. Remarkably, both products of the INK4a/Arf locus were significantly more enriched in the islet than Pdx-1, which is thought to be relatively specific to the islet of adult mice. A close homolog of p16$^{INK4a}$, p18$^{INK4c}$, was significantly expressed in total pancreas; but this expression was not enriched in purified islets, and did not change with aging. These data demonstrate that INK4a/Arf expression in the islet is comparable to that seen in other highly-expressing tissues such as spleen or lung and sharply increases with aging.

Figure 8:
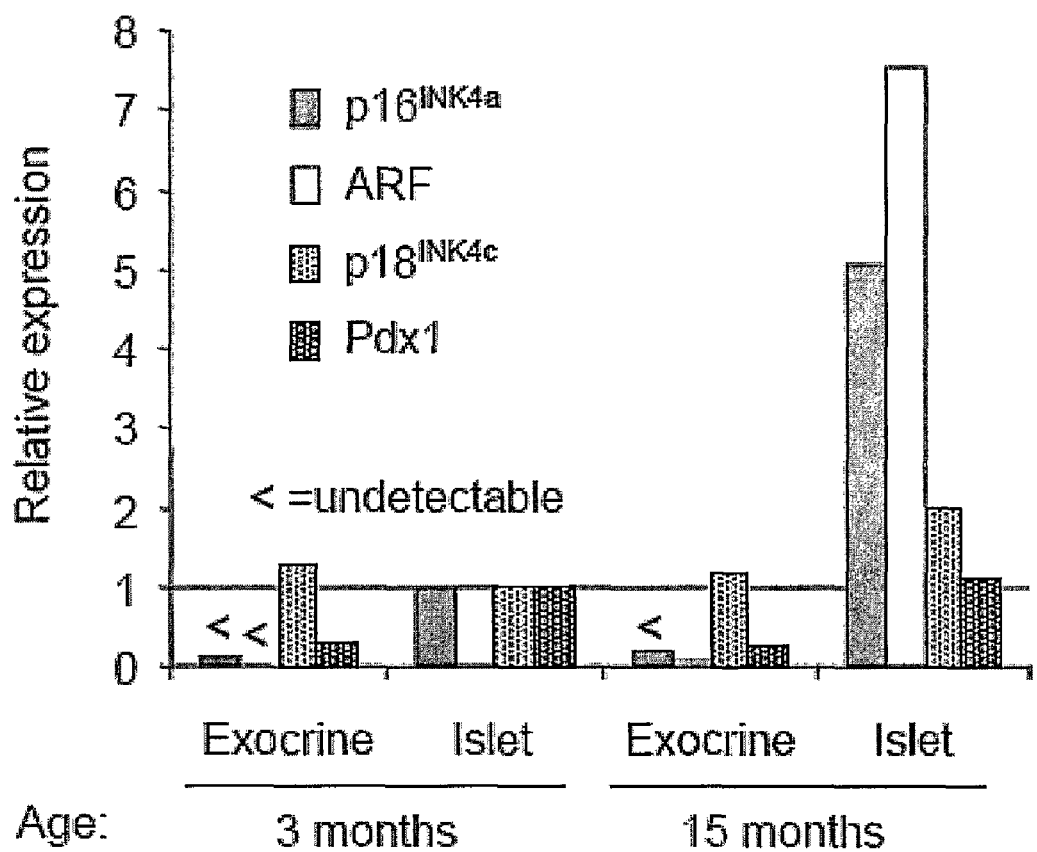
FIG. 8 is a bar graph depicting relative gene expression in exocrine pancreas and pancreatic islets in 3 month old mice and 15 month old mice. p16$^{INK4a}$=gray bar; ARF=white bar; p18=white bar with black stippling; Pdx1=black bar with white stippling. Pdx1 is a gene that is expressed in predominantly in the endocrine pancreas (islets), and therefore establishes the adequacy of islet purification in these experiments. As the expression of p16$^{INK4a}$ and ARF are both significantly more enriched in the endocrine pancreas than Pdx1, this suggests Ink4a/Arf expression is highly specific to the islet.
Figure 9:
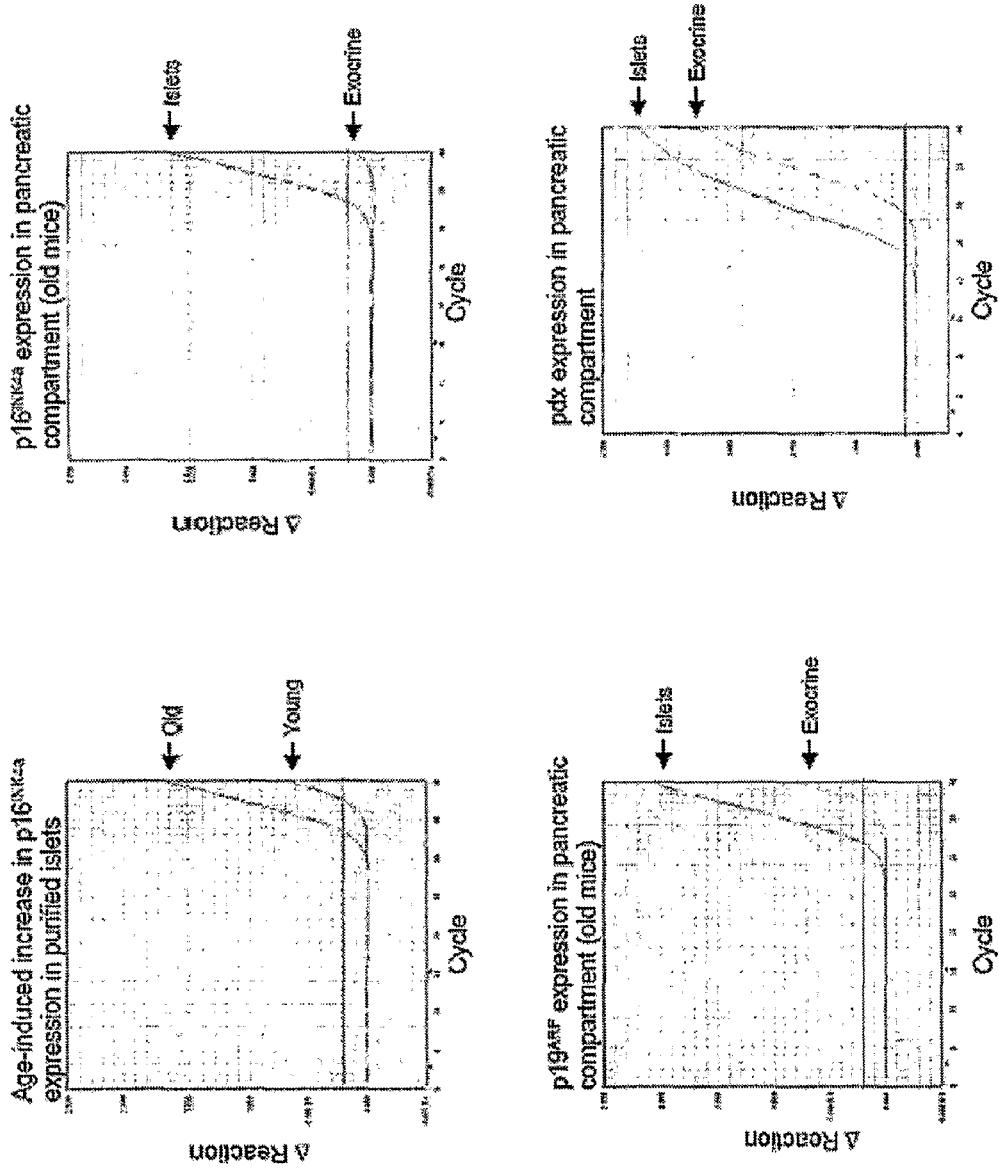
FIG. 9 presents TAQMAN® tracings of islet vs. total pancreas of the subjects represented in FIG. 8.

FIG. 9 shows TAQMAN® analysis tracings of islet vs. total pancreas. FIGS. 8 and 9 show markedly increased p16$^{INK4a}$ and ARF expression in the pancreatic islet (the tissue that makes insulin, and whose failure causes diabetes, a disease that affects 20 million Americans) but not the rest of the pancreas.

Example 6

Mice Lacking p16 Demonstrate Enhanced Islet Regeneration after Exposure to a Potent Islet Toxin FIGS. 10A-10D show that mice lacking p16$^{INK4a}$ demonstrate enhanced islet regeneration after exposure to a potent islet toxin (streptozotocin), indicating that p16$^{INK4a}$ expression limits the islets ability to regenerate in vivo.

To permit the study of the effect of p16$^{INK4a}$ expression on islet proliferation and replicative potential in young adult animals, a model of islet regeneration after sublethal streptozotocin (STZ) treatment was employed. STZ is a well-defined β-cell toxin that induces rapid islet necrosis and diabetes when given as a single dose to adult mice, and β-cell regeneration in rodents is well described after streptozotocin treatment. It was empirically determined that a dose of STZ produced fatal diabetes within 100 days of injection in a majority of wild-type C57Bl/6 mice. Pancreata were then harvested at the indicated time points post-STZ injection, and islet proliferation and morphology were analyzed.

Islet proliferation as assessed by Ki67 staining was significantly increased 48 hours after STZ treatment, and remained elevated for up to two weeks post-STZ. Simultaneously, islets were depleted of insulin+β-cells, and demonstrated significant necrosis at 4 days post-treatment, although median islet size did not nadir till 8 days post-STZ. At this time point, numerous, insulin+small islets associated with pancreatic ducts were evident, with increasing islet size and β-cell number at 14 and 30 days post-STZ. Mice surviving greater than 30 days post-STZ demonstrated a partial, but not complete, recovery of islet size and β-cell number. Coincident with islet recovery, all mice surviving 100 days post-STZ demonstrated near normoglycemia, increased insulin secretion, and weight gain in excess of pre-treatment weight. These data suggest that a single diabetogenic dose of streptozotocin induces fatal diabetes in the majority of young adult C57BI/6 mice, with prolonged survival post-STZ requiring regeneration of significant numbers of functional β-cells.

Importantly, prolonged survival post-STZ was an age-dependent phenotype. Greater than 25% of 5-9 week old mice survive more than 100 days post-STZ, while no mice older than 20 weeks demonstrated persistent survival post-STZ (p=0.026). This result does not likely reflect increased sensitivity to streptozotocin in the older cohort, as old adult mice have been previously shown to be less sensitive to the β-cell damaging effects of STZ. These data suggest that islet regeneration post-STZ is attenuated with aging.

In order to determine if $p16^{INK4a}$ expression contributes to this age-dependent decline in β-cell regeneration post-STZ, streptozotocin challenge was performed in littermate cohorts of adult animals of various ages. Mice aged 5 to 28 weeks of indicated genotypes were treated as described with a single IP injection of STZ, and followed serially for survival (FIGS. 10a-10c), weight (FIG. 10d) and serum glucose. No effect of $p16^{INK4a}$ deficiency on STZ toxicity was noted in 5 to 9 week old mice (FIG. 10a), but $p16^{INK4}$a deficiency afforded a resistance to STZ toxicity in older animals (9 to 15 weeks and 20 to 28 weeks). Animals of these ages exhibited a higher probability of return to normoglycemia; less weight loss; and more rapid recovery to pretreatment weight after STZ injection, and enhanced survival. The greatest survival differences were seen in the oldest mice. Therefore, an age-associated increase in $p16^{INK4a}$ expression appears to limit the recovery of islet function after STZ ablation.

Example 7

Examination of INK4a/ARF Expression in Human Hematopoetic Stem Cells and Lymphocytes A bone marrow sample is obtained from a human subject. Hematopoetic stem cells and lymphocytes are isolated and sorted from the bone marrow sample using standard techniques, including flow cytometry. Nucleic acids (e.g., RNA) are isolated and gene expression analysis is carried out as disclosed herein. A set of primers for $p16^{INK4a}$ expression only, a set of primers for ARF expression only, and a set of primers for expression of both transcripts are employed. Representative primer sets are disclosed herein for human ARF and human $p16^{INK4a}$. Additionally, a pair of human primers for both transcripts from exon 2, 3 is commercially available from Applied Biosystems of Foster City, Calif., United States of America, and this commercially available set is also disclosed herein. The commercially available pair of primers does not discriminate $p16^{INK4a}$ over ARF and so, specific primers for expression of each of these genes are disclosed herein. Lastly, the expression of a "housekeeping" gene (e.g., GAPD, beta-2-microglobulin) is simultaneously determined for the purposes of normalization using commercially available primer sets. Precise and quantitative levels of expression of INK4a, ARF, or both INK4a and ARF are evaluated and the level of expression is used to determine the molecular age of the tissues from the bone marrow. This information is used in clinical decision making about the patient's future care (e.g., toxicity from future chemotherapy).

Example 8

Evaluation of INK4a/ARF Expression in Radiation Port Tissue Biopsies from Human Subjects Tissue biopsies are taken from radiation ports in human subjects who have received radiation treatment for breast cancer and/or lung cancer. The biopsies are isolated in accordance with standard techniques. Nucleic acids are isolated from the biopsied tissue, and gene expression is analyzed in accordance with the presently disclosed subject matter. INK4a expression, ARF expression and/or both INK4a and ARF expression are analyzed. The molecular age of the tissue is determined. This particular tissue is of interest in that radiation is viewed as a DNA damaging agent and can ir-pact the molecular age of a tissue. This information is used in clinical decision making about the patient's future care.

Example 9

Evaluation of INK4a/ARF Expression in Liver to Predict Disease Onset

Liver biopsies are taken from patients with chronic hepatitis. The biopsies are isolated in accordance with standard techniques. Nucleic acids are isolated from the biopsied tissue, and gene expression is analyzed in accordance with the presently disclosed subject matter. INK4a expression, ARF expression and/or both INK4a and ARF expression are analyzed. The molecular age of the tissue is determined, which correlates with future regenerative capacity of the liver. This information is used to predict the future onset of end-stage liver disease (cirrhosis) with concomitant liver failure.

Example 10

Evaluation of INK4a/ARF Expression in Forensic Pathology

Epithelial cells from the perpetrator are left at a crime scene. Nucleic acids are isolated from the remnant cells, and gene expression is analyzed in accordance with the presently disclosed subject matter. Quantitative INK4a expression, ARF expression and/or both INK4a and ARF expression are analyzed, with simultaneous analysis of a "housekeeping" gene. The molecular age of the tissue is determined. This information allows an estimate of the chronologic age of the cell donor, facilitating the police in their search for the perpetrator.

Discussion of Examples 7-10

The above-presented examples provide for the extension of the presently disclosed subject matter to human subjects. Particularly, pairs of human primers directed to the $p16^{INK4a}$ gene only, to the ARF gene only, and to both the $p16^{INK4a}$ and ARF genes are disclosed herein. The analysis of expression of these genes in samples from human subjects is also disclosed. Thus, the presently disclosed subject matter provides for the assessment of quantitative real time expression of these genes in an accurate manner. The assessment of the expression of these genes in tissue samples from various animal species including humans is also provided. The ability to test these genes from almost any tissue source, including but not limited to paraffin embedded material, is also disclosed.

In some embodiments, a housekeeping (HK) gene is measured for the real-time assays. The evaluation of INK4a, ARF, and/or INK4a/ARF expression can employ the simultaneous measurement of a HK gene to control for RNA quality. The choice of HK can depends the application. That is, some HK genes work better than others depending on the tissue of interest. But the chosen HK genes are typically well-defined primers pairs that are commercially available (e.g., Applied Biosystems, Foster City, Calif., United States of America) and validated; and measure genes that are highly expressed.

REFERENCES

The references listed below, as well as all references cited in the specification, are incorporated herein by reference to the extent that they supplement, explain, provide a background for or teach methodology, techniques and/or compositions employed herein.

Bartke et al. (2001) *Nature* 414:412.
Bulavin et al. (2004) *Nat Genet.* 36:343-350.
Burnet (1974) *Intrinsic Mutagenesis: A Genetic Approach to Ageing*, Medical and Technical Publishing Co. Lancaster, England.
Cha & Thilly (1993) *PCR Methods Appl* 3:S18-29.
Dimri et al. (1995) *Proc Natl Acad Sci USA* 92:9363-9367. GENBANK® Accession Nos. MC08963, AAD48924, AAL76337, AF044336, AF115544, AF474975, L81167, NM_009877, NM_058195, NP_034007, NP_478102, and P42771.
Goldstein (1990) *Science* 249:1129-1133.
Goldstein et al. (1969) *Proc Natl Acad Sci USA* 64:155-160.
Ham & McKeehan (1979) *Meth Enzymol* 58:44-93.
Harley (1991) *Mutation Research* 256:271-282.
Harley et al. (1990) *Nature* 345:458-460.
Harman (1956) *J Gerontol* 11:298-300.
Harman (1961) *J Gerontol* 16:247-254.
Hayflick (1965) *Exp Cell Res* 37:614-636.
Hayflick (1992) *Exp Gerontol* 27:363-368
Hayflick & Moorehead (1961) *Exp Cell Res* 25:585-621.
Heid et al. (1996) *Genome Res* 6:986-994.
Jacobs et al. (1999) *Nature* 397:164-168.
Joyce (2002) *Methods Mol Biol* 193:83-92.
Lessard & Sauvageau (2003) *Nature* 423:255-260.
Leung et al. (2004) *Nature* 428:337-341.
Lewis et al. (2001) *Blood* 97:2604-2610.
Linz et al. (1990) *J Clin Chem Clin Biochem* 28:5-13.
Martin et al. (1970) *Lab Invest* 23:86-92.
Martin et al. (1974) *Am J Pathol* 74:137-154.
McPherson et al. (1995) *PCR 2: A Practical Approach*, IRL Press, New York, N.Y., United States of America.
Melk et al., (2003) *Kidney Int* 63:2134-2143.
Meng et al. (2003) *Cancer Res* 63:5414-5419.
Miller et al. (2002) *Mol Endocrinol* 16:2657-2666.
Molofsky et al. (2003) *Nature* 425:962-967.
Ohno (1979) *Mech Aging Dev* 11:179-183.
Olovnikov (1973) *J Theoretical Biology* 41:181-190.
Park et al. (2003) *Nature* 423:302-305.
Robertson & Walsh-Weller (1998) *Methods Mol Biol* 98:121-154.
Roux (1995) *PCR Methods Appl* 4:S185-194.
Sambrook & Russell (2001) *Molecular Cloning: A Laboratory Manual*, 3$^{rd}$ Edition, Cold Spring Harbor Laboratory Press, Cold Spring Harbor, N.Y., United States of America.
Schneider & Mitsui (1976) *Proc Natl Acad Sci USA* 73:3584-3588.
Sharpless et al. (2001) *Nature* 413:86-91.
Shay & Wright (1989) *Exp Cell Res* 184:109-118.
Shay et al. (1991) *Exp Cell Res* 196:33-39.
Shay et al. (1992) *Exp Gerontol* 27:477-492.
Sun et al. (2004) *Genes Dev* 8:1035-1046.
Turturro et al. (1999) *J Gerontol A Biol Sci Med Sci* 54:B492-B501. U.S. Patent Application Publication Nos. 20030099950, 20030226159, 20040014087, 20040033490, 20040048253, 20040054162, and 20040115629.
U.S. Pat. No. 6,066,457.
Vandesompele et al. (2002) *Genome Biol* 3:1-12.
Van Gelder et al. (1990) *Proc Natl Acad Sci USA* 87:1663-1667.
Wang et al. (2000) *Nat Biotechnol* 18:457-459.
Williams (1989) *Biotechniques* 7:762-769.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for predicting a tendency to therapy-induced toxicity in a subject, the method comprising:
   (a) providing a subject under consideration for a therapy;
   (b) providing a sample from the subject, wherein the sample comprises a cell or tissue having a molecular age;
   (c) determining the molecular age of the cell or tissue by:
      (i) quantifying a level of expression of $p16^{INK4a}$, ARF, or both $p16^{INK4a}$ and ARF in the sample;
      (ii) comparing the level of expression quantified with a standard, wherein the comparing comprises determining whether an increased level of expression of $p16^{INK4a}$, ARF, or both $p16^{INK4a}$ and ARF is present or absent in the sample relative to the standard; and
      (iii) determining an increased molecular age if an increased level is present or a lack of an increased molecular age if an increased level is absent; and
   (d) predicting an increased tendency to therapy-induced toxicity in the subject if an increased molecular age is present or a decreased tendency to therapy-induced toxicity in the subject if an increased molecular age is absent.

2. The method of claim 1, further comprising treating the subject with the therapy if a decreased tendency to therapy-induced toxicity is predicted or not treating the subject with the therapy if an increased tendency to therapy-induced toxicity is predicted.

3. The method of claim 1, further comprising treating the subject with the therapy and one or more additional supportive treatments if an increased tendency to therapy-induced toxicity is predicted.

4. A method for determining suitability of a cell or tissue for use in a donation, the method comprising:
   (a) providing a sample from the cell or tissue, wherein the cell or tissue has a molecular age;
   (b) determining the molecular age of the cell or tissue by:
      (i) quantifying a level of expression of $p16^{INK4a}$, ARF, or both $p16^{INK4a}$ and ARF in the sample;
      (ii) comparing the level of expression quantified with a standard, wherein the comparing comprises determining whether an increased level of expression of $p16^{INK4a}$, ARF, or both $p16^{INK4a}$ and ARF is present or absent in the sample relative to the standard; and
      (iii) determining the molecular age based on whether an increased level is present or absent; and
   (c) determining a suitability of the cell or tissue for use in a donation based on the molecular age.

5. The method of claim 2, wherein the cell or tissue donation is appropriate for a transplant selected from the group consisting of bone marrow transplant, solid organ transplant, and tissue graft transplant.

6. A method for determining the molecular age of a cell or tissue in a subject, the method comprising:
   a) providing a sample from the cell or tissue;
   b) quantifying a level of expression of $p16^{INK4a}$, ARF, or both $p16^{INK4a}$ and ARF in the sample; and
   c) determining the molecular age of the cell or tissue by comparing the level of expression of $p16^{INK4a}$, ARF, or both $p16^{INK4a}$ and ARF to a standard.

7. The method of claims 1, 4, or 6, wherein the sample comprises a cell or tissue selected from the group consisting of an adrenal gland cell, a bone marrow cell, a cecum cell, a brain cortex cell, a duodenum cell, a heart cell, a kidney cell, a liver cell, a lung cell, a lymph node cell, an ovary cell, a pancreas cell, a spleen cell, a testis cell, a blood cell, and a uterus cell.

8. The method of claims 1, 4, or 6, further comprising purifying a particular cell type from tissue.

9. The method of claim 5, wherein the particular cell type comprises a lymphocyte, a stem cell, a neural cell, and an islet cell.

10. The method of claims 1, 4 or 6, wherein the standard comprises a quantification of a level of expression of $p16^{INK4a}$, ARF, or both $p16^{INK4a}$ and ARF in a cell or tissue in a population of same species individuals as the subject.

11. The method of claims 1, 4, or 6, wherein the standard comprises a quantification of a level of expression of $p16^{INK4a}$, ARF, or both $p16^{INK4a}$ and ARF in a cell or tissue in the subject at an earlier time.

12. The method of claims 1, 4, or 6, wherein the standard comprises a quantification of a level of expression of $p16^{INK4a}$, ARF, or both $p16^{INK4a}$ and ARF in a second sample isolated from a different tissue of the subject.

13. The method of claim 9, wherein the at least one different tissue comprises a cell selected from the group consisting of an adrenal gland cell, a bone marrow cell, a cecum cell, a brain cortex cell, a duodenum cell, a heart cell, a kidney cell, a liver cell, a lung cell, a lymph node cell, an ovary cell, a pancreas cell, a spleen cell, a testis cell, a blood cell, and a uterus cell.

14. The method of claims 1, 4, or 6, wherein the subject is a human.

15. The method of claims 1, 4, or 6, wherein the quantifying employs quantitative real-time polymerase chain reaction analysis.

16. The method of claims 1, 4, or 6, wherein the comparing the level comprises determining an increased level of expression of $p16^{INK4a}$, ARF, or both $p16^{INK4a}$ and ARF, and the increased level of expression indicates increased molecular age of the tissue relative to the standard.

17. The method of claims 1, 4, or 6, wherein the comparing is to a level of expression of $p16^{INK4a}$, ARF, or both $p16^{INK4a}$ and ARF in the target cell type in a population of same species individuals as the subject.

18. The method of claims 1, 4, or 6, further comprising normalizing the level of expression quantified to a level of expression of a housekeeping gene.

* * * * *

SEQUENCE LISTING

```
<160> NUMBER OF SEQ ID NOS: 39

<210> SEQ ID NO 1
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 1 atg gag ccg gcg gcg ggg agc agc atg gag cct tcg gct gac tgg ctg      48
Met Glu Pro Ala Ala Gly Ser Ser Met Glu Pro Ser Ala Asp Trp Leu
1               5                   10                  15 gcc acg gcc gcg gcc cgg ggt cgg gta gag gag gtg cgg gcg ctg ctg      96
Ala Thr Ala Ala Ala Arg Gly Arg Val Glu Glu Val Arg Ala Leu Leu
            20                  25                  30 gag gcg ggg gcg ctg ccc aac gca ccg aat agt tac ggt cgg agg ccg     144
```

-continued

```
                Glu Ala Gly Ala Leu Pro Asn Ala Pro Asn Ser Tyr Gly Arg Arg Pro
                             35                  40                  45 atc cag gtg ggt aga agg tct gca gcg gga gca ggg gat ggc ggg cga       192
Ile Gln Val Gly Arg Arg Ser Ala Ala Gly Ala Gly Asp Gly Gly Arg
 50                  55                  60 ctc tgg agg acg aag ttt gca ggg gaa ttg gaa tca ggt agc gct tcg       240
Leu Trp Arg Thr Lys Phe Ala Gly Glu Leu Glu Ser Gly Ser Ala Ser
 65                  70                  75                  80 att ctc cgg aaa aag ggg agg ctt cct ggg gag ttt tca gaa ggg gtt       288
Ile Leu Arg Lys Lys Gly Arg Leu Pro Gly Glu Phe Ser Glu Gly Val
                 85                  90                  95 tgt aat cac aga cct cct cct ggc gac gcc ctg ggg gct tgg gaa acc       336
Cys Asn His Arg Pro Pro Pro Gly Asp Ala Leu Gly Ala Trp Glu Thr
            100                 105                 110 aag gaa gag gaa tga                                                    351
Lys Glu Glu Glu
        115

<210> SEQ ID NO 2
<211> LENGTH: 116
<212> TYPE: PRT
<213> ORGANISM: Homo sapiens

<400> SEQUENCE: 2

Met Glu Pro Ala Ala Gly Ser Ser Met Glu Pro Ser Ala Asp Trp Leu
 1               5                  10                  15

Ala Thr Ala Ala Ala Arg Gly Arg Val Glu Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Gly Arg Arg Ser Ala Ala Gly Ala Gly Asp Gly Gly Arg
 50                  55                  60

Leu Trp Arg Thr Lys Phe Ala Gly Glu Leu Glu Ser Gly Ser Ala Ser
 65                  70                  75                  80

Ile Leu Arg Lys Lys Gly Arg Leu Pro Gly Glu Phe Ser Glu Gly Val
                 85                  90                  95

Cys Asn His Arg Pro Pro Pro Gly Asp Ala Leu Gly Ala Trp Glu Thr
            100                 105                 110

Lys Glu Glu Glu
        115

<210> SEQ ID NO 3
<211> LENGTH: 522
<212> TYPE: DNA
<213> ORGANISM: Homo sapiens
<220> FEATURE:
<221> NAME/KEY: CDS
<222> LOCATION: (1)..(522)

<400> SEQUENCE: 3 atg ggc agg ggg cgg tgc gtg ggt ccc agt ctg cag tta agg ggg cag        48
Met Gly Arg Gly Arg Cys Val Gly Pro Ser Leu Gln Leu Arg Gly Gln
 1               5                  10                  15 gag tgg cgc tgc tca cct ctg gtg cca aag ggc ggc gca gcg gct gcc        96
Glu Trp Arg Cys Ser Pro Leu Val Pro Lys Gly Gly Ala Ala Ala Ala
                20                  25                  30 gag ctc ggc cct gga ggc ggc gag aac atg gtg cgc agg ttc ttg gtg       144
Glu Leu Gly Pro Gly Gly Gly Glu Asn Met Val Arg Arg Phe Leu Val
            35                  40                  45 acc ctc cgg att cgg cgc gcg tgc ggc ccg ccg cga gtg agg gtt ttc       192
Thr Leu Arg Ile Arg Arg Ala Cys Gly Pro Pro Arg Val Arg Val Phe
```

```
gtg gtt cac atc ccg cgg ctc acg ggg gag tgg gca gcg cca ggg gcg    240
Val Val His Ile Pro Arg Leu Thr Gly Glu Trp Ala Ala Pro Gly Ala
 65                  70                  75                  80 ccc gcc gct gtg gcc ctc gtg ctg atg cta ctg agg agc cag cgt cta    288
Pro Ala Ala Val Ala Leu Val Leu Met Leu Leu Arg Ser Gln Arg Leu
                 85                  90                  95 ggg cag cag ccg ctt cct aga aga cca ggt cat gat gat ggg cag cgc    336
Gly Gln Gln Pro Leu Pro Arg Arg Pro Gly His Asp Asp Gly Gln Arg
            100                 105                 110 ccg agt ggc gga gct gct gct gct cca cgg cgc gga gcc caa ctg cgc    384
Pro Ser Gly Gly Ala Ala Ala Ala Pro Arg Arg Gly Ala Gln Leu Arg
        115                 120                 125 cga ccc cgc cac tct cac ccg acc cgt gca cga cgc tgc ccg gga ggg    432
Arg Pro Arg His Ser His Pro Thr Arg Ala Arg Arg Cys Pro Gly Gly
    130                 135                 140 ctt cct gga cac gct ggt ggt gct gca ccg ggc cgg ggc gcg gct gga    480
Leu Pro Gly His Ala Gly Gly Ala Ala Pro Gly Arg Gly Ala Ala Gly
145                 150                 155                 160 cgt gcg cga tgc ctg ggg ccg tct gcc cgt gga cct ggc tga            522
Arg Ala Arg Cys Leu Gly Pro Ser Ala Arg Gly Pro Gly
                165                 170

<210> SEQ ID NO 4
<211> LENGTH: 173
<212> TYPE: PRT
<213> ORGANISM: Homo sapiens

<400> SEQUENCE: 4

Met Gly Arg Gly Arg Cys Val Gly Pro Ser Leu Gln Leu Arg Gly Gln
1               5                   10                  15

Glu Trp Arg Cys Ser Pro Leu Val Pro Lys Gly Gly Ala Ala Ala Ala
                20                  25                  30

Glu Leu Gly Pro Gly Gly Glu Asn Met Val Arg Arg Phe Leu Val
            35                  40                  45

Thr Leu Arg Ile Arg Arg Ala Cys Gly Pro Pro Arg Val Arg Val Phe
 50                  55                  60

Val Val His Ile Pro Arg Leu Thr Gly Glu Trp Ala Ala Pro Gly Ala
 65                  70                  75                  80

Pro Ala Ala Val Ala Leu Val Leu Met Leu Leu Arg Ser Gln Arg Leu
                 85                  90                  95

Gly Gln Gln Pro Leu Pro Arg Arg Pro Gly His Asp Asp Gly Gln Arg
            100                 105                 110

Pro Ser Gly Gly Ala Ala Ala Ala Pro Arg Arg Gly Ala Gln Leu Arg
        115                 120                 125

Arg Pro Arg His Ser His Pro Thr Arg Ala Arg Arg Cys Pro Gly Gly
    130                 135                 140

Leu Pro Gly His Ala Gly Gly Ala Ala Pro Gly Arg Gly Ala Ala Gly
145                 150                 155                 160

Arg Ala Arg Cys Leu Gly Pro Ser Ala Arg Gly Pro Gly
                165                 170

<210> SEQ ID NO 5
<211> LENGTH: 507
<212> TYPE: DNA
<213> ORGANISM: Mus sp.
<220> FEATURE:
<221> NAME/KEY: CDS
<222> LOCATION: (1)..(507)
```

```
<400> SEQUENCE: 5 atg gag tcc gct gca gac aga ctg gcc agg gcg gcg gcc cag ggc cgt      48
Met Glu Ser Ala Ala Asp Arg Leu Ala Arg Ala Ala Ala Gln Gly Arg
1               5                   10                  15 gtg cat gac gtg cgg gca ctg ctg gaa gcc ggg gtt tcg ccc aac gcc      96
Val His Asp Val Arg Ala Leu Leu Glu Ala Gly Val Ser Pro Asn Ala
            20                  25                  30 ccg aac tct ttc ggt cgt acc ccg att cag gtg atg atg atg ggc aac     144
Pro Asn Ser Phe Gly Arg Thr Pro Ile Gln Val Met Met Met Gly Asn
        35                  40                  45 gtt cac gta gca gct ctt ctg ctc aac tac ggt gca gat tcg aac tgc     192
Val His Val Ala Ala Leu Leu Leu Asn Tyr Gly Ala Asp Ser Asn Cys
    50                  55                  60 gag gac ccc act acc ttc tcc cgc ccg gtg cac gac gca gcg cgg gaa     240
Glu Asp Pro Thr Thr Phe Ser Arg Pro Val His Asp Ala Ala Arg Glu
65                  70                  75                  80 ggc ttc ctg gac acg ctg gtg gtg ctg cac ggg tca ggg gct cgg ctg     288
Gly Phe Leu Asp Thr Leu Val Val Leu His Gly Ser Gly Ala Arg Leu
                85                  90                  95 gat gtg cgc gat gcc tgg ggt cgc ctg ccg ctc gac ttg gcc caa gag     336
Asp Val Arg Asp Ala Trp Gly Arg Leu Pro Leu Asp Leu Ala Gln Glu
            100                 105                 110 cgg gga cat caa gac atc gtg cga tat ttg cgt tcc gct ggg tgc tct     384
Arg Gly His Gln Asp Ile Val Arg Tyr Leu Arg Ser Ala Gly Cys Ser
        115                 120                 125 ttg tgt tcc gct ggg tgg tct ttg tgt acc gct ggg aac gtc gcc cag     432
Leu Cys Ser Ala Gly Trp Ser Leu Cys Thr Ala Gly Asn Val Ala Gln
    130                 135                 140 acc gac ggg cat agc ttc agc tca agc acg ccc agg gcc ctg gaa ctt     480
Thr Asp Gly His Ser Phe Ser Ser Ser Thr Pro Arg Ala Leu Glu Leu
145                 150                 155                 160 cgc ggc caa tcc caa gag cag agc taa                                  507
Arg Gly Gln Ser Gln Glu Gln Ser
                165

<210> SEQ ID NO 6
<211> LENGTH: 168
<212> TYPE: PRT
<213> ORGANISM: Mus sp.

<400> SEQUENCE: 6

Met Glu Ser Ala Ala Asp Arg Leu Ala Arg Ala Ala Ala Gln Gly Arg
1               5                   10                  15

Val His Asp Val Arg Ala Leu Leu Glu Ala Gly Val Ser Pro Asn Ala
            20                  25                  30

Pro Asn Ser Phe Gly Arg Thr Pro Ile Gln Val Met Met Met Gly Asn
        35                  40                  45

Val His Val Ala Ala Leu Leu Leu Asn Tyr Gly Ala Asp Ser Asn Cys
    50                  55                  60

Glu Asp Pro Thr Thr Phe Ser Arg Pro Val His Asp Ala Ala Arg Glu
65                  70                  75                  80

Gly Phe Leu Asp Thr Leu Val Val Leu His Gly Ser Gly Ala Arg Leu
                85                  90                  95

Asp Val Arg Asp Ala Trp Gly Arg Leu Pro Leu Asp Leu Ala Gln Glu
            100                 105                 110

Arg Gly His Gln Asp Ile Val Arg Tyr Leu Arg Ser Ala Gly Cys Ser
        115                 120                 125

Leu Cys Ser Ala Gly Trp Ser Leu Cys Thr Ala Gly Asn Val Ala Gln
    130                 135                 140
```

Thr Asp Gly His Ser Phe Ser Ser Thr Pro Arg Ala Leu Glu Leu
145                 150                 155                 160

Arg Gly Gln Ser Gln Glu Gln Ser
                165

<210> SEQ ID NO 7
<211> LENGTH: 510
<212> TYPE: DNA
<213> ORGANISM: Mus sp.
<220> FEATURE:
<221> NAME/KEY: CDS
<222> LOCATION: (1)..(510)

<400> SEQUENCE: 7

```
atg ggt cgc agg ttc ttg gtc act gtg agg att cag cgc gcg ggc cgc      48
Met Gly Arg Arg Phe Leu Val Thr Val Arg Ile Gln Arg Ala Gly Arg
1               5                   10                  15 cca ctc caa gag agg gtt ttc ttg gtc aag ttc gtg cga tcc cgg aga      96
Pro Leu Gln Glu Arg Val Phe Leu Val Lys Phe Val Arg Ser Arg Arg
            20                  25                  30 ccc agg aca gcg agc tgc gct ctg gct ttc gtg aac atg ttg ttg agg     144
Pro Arg Thr Ala Ser Cys Ala Leu Ala Phe Val Asn Met Leu Leu Arg
        35                  40                  45 cta gag agg atc ttg aga aga ggg ccg cac cgg aat cct gga cca ggt     192
Leu Glu Arg Ile Leu Arg Arg Gly Pro His Arg Asn Pro Gly Pro Gly
    50                  55                  60 gat gat gat ggg caa cgt tca cgt agc agc tct tct gct caa cta cgg     240
Asp Asp Asp Gly Gln Arg Ser Arg Ser Ser Ser Ser Ala Gln Leu Arg
65                  70                  75                  80 tgc aga ttc gaa ctg cga gga ccc cac tac ctt ctc ccg ccc ggt gca     288
Cys Arg Phe Glu Leu Arg Gly Pro His Tyr Leu Leu Pro Pro Gly Ala
                85                  90                  95 cga cgc agc gcg gga agg ctt cct gga cac gct ggt ggt gct gca cgg     336
Arg Arg Ser Ala Gly Arg Leu Pro Gly His Ala Gly Gly Ala Ala Arg
            100                 105                 110 gtc agg ggc tcg gct gga tgt gcg cga tgc ctg ggg tcg cct gcc gct     384
Val Arg Gly Ser Ala Gly Cys Ala Arg Cys Leu Gly Ser Pro Ala Ala
        115                 120                 125 cga ctt ggc cca aga gcg ggg aca tca aga cat cgt gcg ata ttt gcg     432
Arg Leu Gly Pro Arg Ala Gly Thr Ser Arg His Arg Ala Ile Phe Ala
    130                 135                 140 ttc cgc tgg gtg ctc ttt gtg ttc cgc tgg gtg gtc ttt gtg tac cgc     480
Phe Arg Trp Val Leu Phe Val Phe Arg Trp Val Val Phe Val Tyr Arg
145                 150                 155                 160 tgg gaa cgt cgc cca gac cga cgg gca tag                             510
Trp Glu Arg Arg Pro Asp Arg Arg Ala
                165
```

<210> SEQ ID NO 8
<211> LENGTH: 169
<212> TYPE: PRT
<213> ORGANISM: Mus sp.

<400> SEQUENCE: 8

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
            20                  25                  30

Pro Arg Thr Ala Ser Cys Ala Leu Ala Phe Val Asn Met Leu Leu Arg
        35                  40                  45

Leu Glu Arg Ile Leu Arg Arg Gly Pro His Arg Asn Pro Gly Pro Gly

-continued

```
            50                  55                  60
Asp Asp Asp Gly Gln Arg Ser Arg Ser Ser Ser Ala Gln Leu Arg
65                  70                  75                  80

Cys Arg Phe Glu Leu Arg Gly Pro His Tyr Leu Leu Pro Gly Ala
                85                  90                  95

Arg Arg Ser Ala Gly Arg Leu Pro Gly His Ala Gly Ala Ala Arg
            100                 105                 110

Val Arg Gly Ser Ala Gly Cys Ala Arg Cys Leu Gly Ser Pro Ala Ala
            115                 120                 125

Arg Leu Gly Pro Arg Ala Gly Thr Ser Arg His Arg Ala Ile Phe Ala
        130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165
```

```
<210> SEQ ID NO 9
<211> LENGTH: 480
<212> TYPE: DNA
<213> ORGANISM: Rattus sp.
<220> FEATURE:
<221> NAME/KEY: CDS
<222> LOCATION: (1)..(480)

<400> SEQUENCE: 9 atg gag tcc tct gca gat aga cta gcc agg gca gcg gcc ctg ggc cgt      48
Met Glu Ser Ser Ala Asp Arg Leu Ala Arg Ala Ala Ala Leu Gly Arg
1               5                   10                  15 gag cac gag gtg cgg gca ctg ctg gaa gcc ggg gct tca cca aac gcc      96
Glu His Glu Val Arg Ala Leu Leu Glu Ala Gly Ala Ser Pro Asn Ala
                20                  25                  30 ccg aac act ttc ggt cgt acc ccg ata cag gtg atg atg atg ggc aac     144
Pro Asn Thr Phe Gly Arg Thr Pro Ile Gln Val Met Met Met Gly Asn
            35                  40                  45 gtc aaa gtg gca gct ctc ctg ctc tcc tat ggt gca gat tcg aac tgc     192
Val Lys Val Ala Ala Leu Leu Leu Ser Tyr Gly Ala Asp Ser Asn Cys
        50                  55                  60 gag gac ccc acc acc ctc tcc cga ccg gtg cac gac gca gcg cgg gag     240
Glu Asp Pro Thr Thr Leu Ser Arg Pro Val His Asp Ala Ala Arg Glu
65                  70                  75                  80 ggc ttc cta gac act ctg gta gta ctg cac cag gca ggg gcg cgg ctg     288
Gly Phe Leu Asp Thr Leu Val Val Leu His Gln Ala Gly Ala Arg Leu
                85                  90                  95 gat gtg cgc gat gcc tgg ggt cgc ctg ccg ctc gac ctg gcc cta gag     336
Asp Val Arg Asp Ala Trp Gly Arg Leu Pro Leu Asp Leu Ala Leu Glu
            100                 105                 110 cgg gga cat cac gac gtc gtg cgg tat ttg cgg tat cta ctc tcc tcc     384
Arg Gly His His Asp Val Val Arg Tyr Leu Arg Tyr Leu Leu Ser Ser
        115                 120                 125 gct ggg aac gtt tcc cgg gtc acc gac agg cat aac ttc tgc tca agc     432
Ala Gly Asn Val Ser Arg Val Thr Asp Arg His Asn Phe Cys Ser Ser
130                 135                 140 acg ccc agg tgc cta gga ctt cga ggc caa ccc cca aag cag cgc taa     480
Thr Pro Arg Cys Leu Gly Leu Arg Gly Gln Pro Pro Lys Gln Arg
145                 150                 155
```

```
<210> SEQ ID NO 10
<211> LENGTH: 159
<212> TYPE: PRT
<213> ORGANISM: Rattus sp.
```

<400> SEQUENCE: 10

| | | | | | | | | | | | | | | |
|---|---|---|---|---|---|---|---|---|---|---|---|---|---|---|
|Met|Glu|Ser|Ser|Ala|Asp|Arg|Leu|Ala|Arg|Ala|Ala|Leu|Gly|Arg|
|1| | | |5| | | | |10| | | | |15|

Glu His Glu Val Arg Ala Leu Leu Glu Ala Gly Ala Ser Pro Asn Ala
                20                  25                  30

Pro Asn Thr Phe Gly Arg Thr Pro Ile Gln Val Met Met Met Gly Asn
            35                  40                  45

Val Lys Val Ala Ala Leu Leu Leu Ser Tyr Gly Ala Asp Ser Asn Cys
 50                  55                  60

Glu Asp Pro Thr Thr Leu Ser Arg Pro Val His Asp Ala Ala Arg Glu
65                  70                  75                  80

Gly Phe Leu Asp Thr Leu Val Val Leu His Gln Ala Gly Ala Arg Leu
                85                  90                  95

Asp Val Arg Asp Ala Trp Gly Arg Leu Pro Leu Asp Leu Ala Leu Glu
            100                 105                 110

Arg Gly His His Asp Val Val Arg Tyr Leu Arg Tyr Leu Leu Ser Ser
        115                 120                 125

Ala Gly Asn Val Ser Arg Val Thr Asp Arg His Asn Phe Cys Ser Ser
130                 135                 140

Thr Pro Arg Cys Leu Gly Leu Arg Gly Gln Pro Pro Lys Gln Arg
145                 150                 155

```
<210> SEQ ID NO 11
<211> LENGTH: 483
<212> TYPE: DNA
<213> ORGANISM: Rattus sp.
<220> FEATURE:
<221> NAME/KEY: CDS
<222> LOCATION: (1)..(483)
```

<400> SEQUENCE: 11

| | | | | | | |
|---|---|---|---|---|---|---|
|atg ggt cgc agg ttc gtg gtc act gtg agg att cgg cgc aca ggg cgc|||||||48|
|Met Gly Arg Arg Phe Val Val Thr Val Arg Ile Arg Arg Thr Gly Arg|||||||
|1                   5                   10                  15|||||||
|tca ccc caa gtg agg gtt ttc ttg gtg cag ttc ctg gga tcc tcg cga|||||||96|
|Ser Pro Gln Val Arg Val Phe Leu Val Gln Phe Leu Gly Ser Ser Arg|||||||
|                20                  25                  30|||||||
|ccc agg tca gcg aac ggc aca cga ggt ttc gtg gcc ttg gtg ttg agg|||||||144|
|Pro Arg Ser Ala Asn Gly Thr Arg Gly Phe Val Ala Leu Val Leu Arg|||||||
|            35                  40                  45|||||||
|cca gag agg atc gcg cgg aga ggg ccg cag cca cat cct gga cca ggt|||||||192|
|Pro Glu Arg Ile Ala Arg Arg Gly Pro Gln Pro His Pro Gly Pro Gly|||||||
| 50                  55                  60|||||||
|gat gat gat ggg caa cgt caa agt ggc agc tct cct gct ctc cta tgg|||||||240|
|Asp Asp Asp Gly Gln Arg Gln Ser Gly Ser Ser Pro Ala Leu Leu Trp|||||||
|65                  70                  75                  80|||||||
|tgc aga ttc gaa ctg cga gga ccc cac cac cct ctc ccg acc ggt gca|||||||288|
|Cys Arg Phe Glu Leu Arg Gly Pro His His Pro Leu Pro Thr Gly Ala|||||||
|                85                  90                  95|||||||
|cga cgc agc gcg gga ggg ctt cct aga cac tct ggt agt act gca cca|||||||336|
|Arg Arg Ser Ala Gly Gly Leu Pro Arg His Ser Gly Ser Thr Ala Pro|||||||
|            100                 105                 110|||||||
|ggc agg ggc gcg gct gga tgt gcg cga tgc ctg ggg tcg cct gcc gct|||||||384|
|Gly Arg Gly Ala Ala Gly Cys Ala Arg Cys Leu Gly Ser Pro Ala Ala|||||||
|        115                 120                 125|||||||
|cga cct ggc cct aga gcg ggg aca tca cga cgt cgt gcg gta ttt gcg|||||||432|
|Arg Pro Gly Pro Arg Ala Gly Thr Ser Arg Arg Arg Ala Val Phe Ala|||||||
|130                 135                 140|||||||
|gta tct act ctc ctc cgc tgg gaa cgt ttc ccg ggt cac cga cag gca|||||||480|

```
Val Ser Thr Leu Leu Arg Trp Glu Arg Phe Pro Gly His Arg Gln Ala
145                 150                 155                 160 taa                                                                        483

<210> SEQ ID NO 12
<211> LENGTH: 160
<212> TYPE: PRT
<213> ORGANISM: Rattus sp.

<400> SEQUENCE: 12

Met Gly Arg Arg Phe Val Val Thr Val Arg Ile Arg Arg Thr Gly Arg
1               5                   10                  15

Ser Pro Gln Val Arg Val Phe Leu Val Gln Phe Leu Gly Ser Ser Arg
                20                  25                  30

Pro Arg Ser Ala Asn Gly Thr Arg Gly Phe Val Ala Leu Val Leu Arg
            35                  40                  45

Pro Glu Arg Ile Ala Arg Arg Gly Pro Gln Pro His Pro Gly Pro Gly
        50                  55                  60

Asp Asp Asp Gly Gln Arg Gln Ser Gly Ser Ser Pro Ala Leu Leu Trp
65                  70                  75                  80

Cys Arg Phe Glu Leu Arg Gly Pro His His Pro Leu Pro Thr Gly Ala
                85                  90                  95

Arg Arg Ser Ala Gly Gly Leu Pro Arg His Ser Gly Ser Thr Ala Pro
                100                 105                 110

Gly Arg Gly Ala Ala Gly Cys Ala Arg Cys Leu Gly Ser Pro Ala Ala
            115                 120                 125

Arg Pro Gly Pro Arg Ala Gly Thr Ser Arg Arg Ala Val Phe Ala
        130                 135                 140

Val Ser Thr Leu Leu Arg Trp Glu Arg Phe Pro Gly His Arg Gln Ala
145                 150                 155                 160

<210> SEQ ID NO 13
<211> LENGTH: 16
<212> TYPE: DNA
<213> ORGANISM: Mus sp.

<400> SEQUENCE: 13
cccaacgccc cgaact                                                           16

<210> SEQ ID NO 14
<211> LENGTH: 21
<212> TYPE: DNA
<213> ORGANISM: Mus sp.

<400> SEQUENCE: 14
gcagaagagc tgctacgtga a                                                     21

<210> SEQ ID NO 15
<211> LENGTH: 24
<212> TYPE: DNA
<213> ORGANISM: Mus sp.

<400> SEQUENCE: 15
ttcggtcgta ccccgattca ggtg                                                  24

<210> SEQ ID NO 16
<211> LENGTH: 19
<212> TYPE: DNA
<213> ORGANISM: Mus sp.

<400> SEQUENCE: 16
```

```
cggtcgtacc ccgattcag                                              19

<210> SEQ ID NO 17
<211> LENGTH: 22
<212> TYPE: DNA
<213> ORGANISM: Mus sp.

<400> SEQUENCE: 17
gcaccgtagt tgagcagaag ag                                          22

<210> SEQ ID NO 18
<211> LENGTH: 17
<212> TYPE: DNA
<213> ORGANISM: Mus sp.

<400> SEQUENCE: 18
aacgttgccc atcatca                                                17

<210> SEQ ID NO 19
<211> LENGTH: 23
<212> TYPE: DNA
<213> ORGANISM: Mus sp.

<400> SEQUENCE: 19
tgaggctaga gaggatcttg aga                                         23

<210> SEQ ID NO 20
<211> LENGTH: 21
<212> TYPE: DNA
<213> ORGANISM: Mus sp.

<400> SEQUENCE: 20
gcagaagagc tgctacgtga a                                           21

<210> SEQ ID NO 21
<211> LENGTH: 20
<212> TYPE: DNA
<213> ORGANISM: Mus sp.

<400> SEQUENCE: 21
ccgcaccgga atcctggacc                                             20

<210> SEQ ID NO 22
<211> LENGTH: 25
<212> TYPE: DNA
<213> ORGANISM: Mus sp.

<400> SEQUENCE: 22
tgaggctaga gaggatcttg agaag                                       25

<210> SEQ ID NO 23
<211> LENGTH: 22
<212> TYPE: DNA
<213> ORGANISM: Mus sp.

<400> SEQUENCE: 23
gtgaacgttg cccatcatca tc                                          22

<210> SEQ ID NO 24
<211> LENGTH: 16
<212> TYPE: DNA
<213> ORGANISM: Mus sp.

<400> SEQUENCE: 24
```

```
acctggtcca ggattc                                                     16

<210> SEQ ID NO 25
<211> LENGTH: 23
<212> TYPE: DNA
<213> ORGANISM: Mus sp.

<400> SEQUENCE: 25
agaagagatt tttatgcagc tca                                             23

<210> SEQ ID NO 26
<211> LENGTH: 20
<212> TYPE: DNA
<213> ORGANISM: Mus sp.

<400> SEQUENCE: 26
caacttctcc tcggtcttca                                                 20

<210> SEQ ID NO 27
<211> LENGTH: 23
<212> TYPE: DNA
<213> ORGANISM: Mus sp.

<400> SEQUENCE: 27
agctgatgct gccaatggct cca                                             23

<210> SEQ ID NO 28
<211> LENGTH: 17
<212> TYPE: DNA
<213> ORGANISM: Rattus sp.

<400> SEQUENCE: 28
accaaacgcc ccgaaca                                                    17

<210> SEQ ID NO 29
<211> LENGTH: 20
<212> TYPE: DNA
<213> ORGANISM: Rattus sp.

<400> SEQUENCE: 29
gagagctgcc actttgacgt                                                 20

<210> SEQ ID NO 30
<211> LENGTH: 24
<212> TYPE: DNA
<213> ORGANISM: Rattus sp.

<400> SEQUENCE: 30
tcggtcgtac cccgatacag gtga                                            24

<210> SEQ ID NO 31
<211> LENGTH: 17
<212> TYPE: DNA
<213> ORGANISM: Rattus sp.

<400> SEQUENCE: 31
gagggccgca gccacat                                                    17

<210> SEQ ID NO 32
<211> LENGTH: 23
<212> TYPE: DNA
<213> ORGANISM: Rattus sp.

<400> SEQUENCE: 32
```

```
caccatagga gagcaggaga gct                                    23

<210> SEQ ID NO 33
<211> LENGTH: 24
<212> TYPE: DNA
<213> ORGANISM: Rattus sp.

<400> SEQUENCE: 33
cgttgcccat catcatcacc tggt                                   24

<210> SEQ ID NO 34
<211> LENGTH: 21
<212> TYPE: DNA
<213> ORGANISM: Homo sapiens

<400> SEQUENCE: 34
ccaacgcacc gaatagttac g                                      21

<210> SEQ ID NO 35
<211> LENGTH: 18
<212> TYPE: DNA
<213> ORGANISM: Homo sapiens

<400> SEQUENCE: 35
gcgctgccca tcatcatg                                          18

<210> SEQ ID NO 36
<211> LENGTH: 18
<212> TYPE: DNA
<213> ORGANISM: Homo sapiens

<400> SEQUENCE: 36
cctggatcgg cctccgac                                          18

<210> SEQ ID NO 37
<211> LENGTH: 19
<212> TYPE: DNA
<213> ORGANISM: Homo sapiens

<400> SEQUENCE: 37
ctgaggagcc agcgtctag                                         19

<210> SEQ ID NO 38
<211> LENGTH: 25
<212> TYPE: DNA
<213> ORGANISM: Homo sapiens

<400> SEQUENCE: 38
cccatcatca tgacctggtc ttcta                                  25

<210> SEQ ID NO 39
<211> LENGTH: 14
<212> TYPE: DNA
<213> ORGANISM: Homo sapiens

<400> SEQUENCE: 39
cagcagccgc ttcc                                              14
```